United States Patent
Bojarski et al.

(10) Patent No.: US 9,675,471 B2
(45) Date of Patent: Jun. 13, 2017

(54) DEVICES, TECHNIQUES AND METHODS FOR ASSESSING JOINT SPACING, BALANCING SOFT TISSUES AND OBTAINING DESIRED KINEMATICS FOR JOINT IMPLANT COMPONENTS

(71) Applicant: CONFORMIS, INC., Bedford, MA (US)

(72) Inventors: Raymond A Bojarski, Attleboro, MA (US); Wolfgang Fitz, Sherborn, MA (US)

(73) Assignee: ConforMIS, Inc., Billerica, MA (US)

( * ) Notice: Subject to any disclaimer, the term of this patent is extended or adjusted under 35 U.S.C. 154(b) by 476 days.

(21) Appl. No.: 13/915,609

(22) Filed: Jun. 11, 2013

(65) Prior Publication Data

US 2013/0331850 A1    Dec. 12, 2013

Related U.S. Application Data

(60) Provisional application No. 61/657,993, filed on Jun. 11, 2012.

(51) Int. Cl.
*A61F 2/46* (2006.01)
*A61F 2/40* (2006.01)
(Continued)

(52) U.S. Cl.
CPC ............ *A61F 2/4657* (2013.01); *A61B 90/06* (2016.02); *A61F 2/40* (2013.01); *A61F 2/4684* (2013.01); *A61B 2090/061* (2016.02); *A61F 2/38* (2013.01); *A61F 2/389* (2013.01); *A61F 2002/30153* (2013.01); *A61F 2002/30617* (2013.01); *A61F 2002/4661* (2013.01)

(58) Field of Classification Search
CPC ............ A61F 2/4657; A61F 2002/4661; A61F 2/4684; A61F 2/32; A61F 2/38; A61F 2/40; A61B 90/06; A61B 2090/061
See application file for complete search history.

(56) References Cited

U.S. PATENT DOCUMENTS

| | | | |
|---|---|---|---|
| 3,314,420 A | 4/1967 | Smith et al. | 128/92 |
| 3,605,123 A | 9/1971 | Hahn | 3/1 |

(Continued)

FOREIGN PATENT DOCUMENTS

| | | | |
|---|---|---|---|
| CN | 101288597 A | 10/2008 | A61B 17/56 |
| DE | 2306552 | 8/1974 | A61F 1/00 |

(Continued)

OTHER PUBLICATIONS

Andersson et al., "MacIntosh Arthroplasty in Rheumatoid Arthritis," Acta. Orthrop. Scand. 45(2):245-259 (1974).

(Continued)

*Primary Examiner* — Larry E Waggle, Jr.
(74) *Attorney, Agent, or Firm* — Sunstein Kann Murphy & Timbers LLP

(57) ABSTRACT

Improved assessment probes and measuring tools, systems, procedures and methods to facilitate the selection and/or implantation of prosthetic joint components, and assist a surgeon or medical practitioner with the proper assessment, balancing and/or restoration of natural and/or desired joint kinematics during a joint replacement procedure.

5 Claims, 14 Drawing Sheets

(51) Int. Cl.
*A61B 90/00* (2016.01)
*A61F 2/38* (2006.01)
*A61F 2/30* (2006.01)

(56) References Cited

U.S. PATENT DOCUMENTS

| | | | |
|---|---|---|---|
| 3,798,679 A | 3/1974 | Ewald | 3/1 |
| 3,808,606 A | 5/1974 | Tronzo | 3/1 |
| 3,843,975 A | 10/1974 | Tronzo | 3/1 |
| 3,855,638 A | 12/1974 | Pilliar | 3/1 |
| 3,869,731 A | 3/1975 | Waugh et al. | 3/1 |
| 3,938,198 A | 2/1976 | Kahn et al. | 3/1.912 |
| 3,987,499 A | 10/1976 | Scharbach et al. | 3/1.91 |
| 4,052,753 A | 10/1977 | Dedo | 3/1 |
| 4,055,862 A | 11/1977 | Farling | 3/1.91 |
| 4,085,466 A | 4/1978 | Goodfellow et al. | 3/1.91 |
| 4,098,626 A | 7/1978 | Graham et al. | 149/19.4 |
| 4,203,444 A | 5/1980 | Bonnell et al. | 128/276 |
| 4,211,228 A * | 7/1980 | Cloutier | A61F 2/389 606/102 |
| 4,213,816 A | 7/1980 | Morris | 156/245 |
| 4,340,978 A | 7/1982 | Buechel et al. | 3/1.911 |
| 4,368,040 A | 1/1983 | Weissman | 433/36 |
| 4,436,684 A | 3/1984 | White | 264/138 |
| 4,474,177 A | 10/1984 | Whiteside | 128/303 R |
| 4,501,266 A | 2/1985 | McDaniel | 128/69 |
| 4,502,161 A | 3/1985 | Wall | 3/1.91 |
| 4,502,483 A | 3/1985 | Lacey | 128/303 R |
| 4,586,496 A | 5/1986 | Keller | 128/92 E |
| 4,594,380 A | 6/1986 | Chapin et al. | 524/144 |
| 4,601,290 A | 7/1986 | Effron et al. | 128/305 |
| 4,609,551 A | 9/1986 | Caplan et al. | 424/95 |
| 4,627,853 A | 12/1986 | Campbell et al. | 623/16 |
| 4,646,729 A | 3/1987 | Kenna et al. | 128/92 VW |
| 4,715,860 A | 12/1987 | Amstutz et al. | 623/22 |
| 4,721,104 A | 1/1988 | Kaufman et al. | 128/92 |
| 4,759,350 A | 7/1988 | Dunn et al. | 128/92 VW |
| 4,769,040 A | 9/1988 | Wevers | 623/20 |
| 4,841,975 A | 6/1989 | Woolson | 128/653 |
| 4,846,835 A | 7/1989 | Grande | 623/11 |
| 4,865,607 A | 9/1989 | Witzel et al. | 623/20 |
| 4,880,429 A | 11/1989 | Stone | 623/18 |
| 4,886,258 A | 12/1989 | Scott | 269/328 |
| 4,936,862 A | 6/1990 | Walker et al. | 623/23 |
| 4,979,949 A | 12/1990 | Matsen, III et al. | 606/53 |
| 5,002,547 A | 3/1991 | Poggie et al. | 606/88 |
| 5,041,138 A | 8/1991 | Vacanti et al. | 623/16 |
| 5,053,039 A | 10/1991 | Hofmann et al. | 606/87 |
| 5,059,216 A | 10/1991 | Winters | 623/20 |
| 5,067,964 A | 11/1991 | Richmond et al. | 623/18 |
| 5,098,383 A | 3/1992 | Hemmy et al. | 604/10 |
| 5,107,824 A | 4/1992 | Rogers et al. | 602/16 |
| 5,122,144 A | 6/1992 | Bert et al. | 606/88 |
| 5,129,908 A | 7/1992 | Peterson | 606/88 |
| 5,133,759 A | 7/1992 | Turner | 623/20 |
| 5,152,796 A | 10/1992 | Slamin | 623/20 |
| 5,154,717 A | 10/1992 | Matsen, III et al. | 606/53 |
| 5,162,430 A | 11/1992 | Rhee et al. | 525/54.1 |
| 5,171,244 A | 12/1992 | Caspari et al. | 606/88 |
| 5,171,322 A | 12/1992 | Kenny | 623/18 |
| 5,197,985 A | 3/1993 | Caplan et al. | 623/16 |
| 5,206,023 A | 4/1993 | Hunziker | 424/423 |
| 5,226,914 A | 7/1993 | Caplan et al. | 623/16 |
| 5,234,433 A | 8/1993 | Bert et al. | 606/88 |
| 5,246,530 A | 9/1993 | Bugle et al. | 156/643 |
| 5,250,050 A | 10/1993 | Poggie et al. | 606/79 |
| 5,258,032 A | 11/1993 | Bertin | 623/20 |
| 5,270,300 A | 12/1993 | Hunziker | 514/12 |
| 5,288,797 A | 2/1994 | Khalil et al. | 524/872 |
| 5,303,148 A | 4/1994 | Mattson et al. | 364/413.01 |
| 5,306,311 A | 4/1994 | Stone et al. | 623/18 |
| 5,314,482 A | 5/1994 | Goodfellow et al. | 623/20 |
| 5,320,102 A | 6/1994 | Paul et al. | 128/653.2 |
| 5,344,459 A | 9/1994 | Swartz | 623/18 |
| 5,360,446 A | 11/1994 | Kennedy | 623/16 |
| 5,365,996 A | 11/1994 | Crook | 164/45 |
| 5,368,858 A | 11/1994 | Hunziker | 424/423 |
| 5,380,332 A | 1/1995 | Ferrante | 606/79 |
| 5,387,216 A | 2/1995 | Thornhill et al. | 606/88 |
| 5,403,319 A | 4/1995 | Matsen, III et al. | 606/88 |
| 5,413,605 A | 5/1995 | Ashby et al. | 623/20 |
| 5,437,676 A | 8/1995 | Bouraly et al. | 606/88 |
| 5,468,787 A | 11/1995 | Braden et al. | 523/113 |
| 5,474,559 A | 12/1995 | Bertin et al. | 606/89 |
| 5,478,739 A | 12/1995 | Slivka et al. | 435/240.23 |
| 5,486,180 A | 1/1996 | Dietz et al. | 606/87 |
| 5,501,687 A | 3/1996 | Willert et al. | 606/94 |
| 5,503,162 A | 4/1996 | Athanasiou et al. | 128/774 |
| 5,520,695 A | 5/1996 | Luckman | 606/88 |
| 5,523,843 A | 6/1996 | Yamane et al. | 356/363 |
| 5,540,696 A | 7/1996 | Booth, Jr. et al. | 606/88 |
| 5,542,947 A | 8/1996 | Treacy | 606/88 |
| 5,554,190 A | 9/1996 | Draenert | 623/16 |
| 5,556,432 A | 9/1996 | Kubein-Meesenburg et al. | 623/20 |
| 5,571,205 A | 11/1996 | James | 623/24 |
| 5,575,793 A | 11/1996 | Carls et al. | 606/80 |
| 5,578,037 A | 11/1996 | Sanders et al. | 606/80 |
| 5,593,450 A | 1/1997 | Scott et al. | 623/20 |
| 5,597,379 A | 1/1997 | Haines et al. | 606/80 |
| 5,601,563 A | 2/1997 | Burke et al. | 606/86 |
| 5,613,970 A | 3/1997 | Houston et al. | 606/88 |
| 5,616,146 A | 4/1997 | Murray | 606/80 |
| 5,630,820 A | 5/1997 | Todd | 606/90 |
| 5,632,745 A | 5/1997 | Schwartz | 606/75 |
| 5,649,929 A | 7/1997 | Callaway | 606/88 |
| 5,658,291 A | 8/1997 | Techiera | 606/80 |
| 5,671,741 A | 9/1997 | Lang et al. | 128/653.2 |
| 5,681,316 A | 10/1997 | DeOrio et al. | 606/88 |
| 5,681,354 A | 10/1997 | Eckhoff | 623/20 |
| 5,682,886 A | 11/1997 | Delp et al. | 128/653.1 |
| 5,683,466 A | 11/1997 | Vitale | 623/18 |
| 5,684,562 A | 11/1997 | Fujieda | 351/212 |
| 5,688,282 A | 11/1997 | Baron et al. | 606/90 |
| 5,728,162 A | 3/1998 | Eckhoff | 623/20 |
| 5,735,277 A | 4/1998 | Schuster | 128/653.1 |
| 5,749,874 A | 5/1998 | Schwartz | 606/75 |
| 5,749,876 A | 5/1998 | Duvillier et al. | 606/88 |
| 5,766,259 A | 6/1998 | Sammarco | 623/21 |
| 5,768,134 A | 6/1998 | Swaelens et al. | 364/468.28 |
| 5,769,899 A | 6/1998 | Schwartz et al. | 623/18 |
| 5,776,137 A | 7/1998 | Katz | 606/88 |
| 5,786,217 A | 7/1998 | Tubo et al. | 435/402 |
| 5,795,353 A | 8/1998 | Felt | 623/18 |
| 5,800,438 A | 9/1998 | Tuke et al. | 606/90 |
| 5,827,289 A | 10/1998 | Reiley et al. | 606/86 |
| 5,830,216 A | 11/1998 | Insall et al. | 606/88 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,860,981 A | 1/1999 | Bertin et al. | 606/89 |
| 5,871,018 A | 2/1999 | Delp et al. | 128/898 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,297 A | 3/1999 | Matsen, III | 606/87 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,934 A | 5/1999 | Grande et al. | 435/325 |
| 5,911,723 A | 6/1999 | Ashby et al. | 606/88 |
| 5,916,220 A | 6/1999 | Masini | 606/88 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 5,995,738 A | 11/1999 | DiGioia, III et al. | 395/500.32 |
| 6,001,895 A | 12/1999 | Harvey et al. | 523/113 |
| 6,002,859 A | 12/1999 | DiGioia, III et al. | 395/500.32 |

(56) References Cited

U.S. PATENT DOCUMENTS

| | | | |
|---|---|---|---|
| 6,007,537 A | 12/1999 | Burkinshaw et al. | 606/66 |
| 6,010,509 A | 1/2000 | Delgado et al. | 606/88 |
| 6,013,103 A | 1/2000 | Kaufman et al. | 623/20 |
| 6,039,764 A | 3/2000 | Pottenger et al. | 623/20 |
| 6,046,379 A | 4/2000 | Stone et al. | 623/11 |
| 6,056,754 A | 5/2000 | Haines et al. | 606/80 |
| 6,056,756 A | 5/2000 | Eng et al. | 606/87 |
| 6,057,927 A | 5/2000 | Lévesque et al. | 356/432 T |
| 6,077,270 A | 6/2000 | Katz | 606/88 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,096,043 A | 8/2000 | Techiera et al. | 606/88 |
| 6,102,916 A | 8/2000 | Masini | 606/88 |
| 6,106,529 A | 8/2000 | Techiera | 606/88 |
| 6,110,209 A | 8/2000 | Stone | 623/16.11 |
| 6,120,541 A | 9/2000 | Johnson | 623/14.12 |
| 6,126,690 A | 10/2000 | Ateshian et al. | 623/18 |
| 6,139,578 A | 10/2000 | Lee et al. | 623/16.11 |
| 6,156,069 A | 12/2000 | Amstutz | 623/22.11 |
| 6,161,080 A | 12/2000 | Aouni-Ateshian et al. | 703/11 |
| 6,187,010 B1 | 2/2001 | Masini | 606/86 |
| 6,200,606 B1 | 3/2001 | Peterson et al. | 424/574 |
| 6,203,546 B1 | 3/2001 | MacMahon | 606/87 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,052 B1 | 4/2001 | Burkinshaw | 623/20.34 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,251,143 B1 | 6/2001 | Schwartz et al. | 623/23.72 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,296,646 B1 | 10/2001 | Williamson | 606/90 |
| 6,299,905 B1 | 10/2001 | Peterson et al. | 424/486 |
| 6,322,588 B1 | 11/2001 | Ogle et al. | 623/1.46 |
| 6,328,765 B1 | 12/2001 | Hardwick et al. | 623/23.72 |
| 6,344,043 B1 | 2/2002 | Pappas | 606/96 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,459,948 B1 | 10/2002 | Ateshian et al. | 700/117 |
| 6,468,314 B2 | 10/2002 | Schwartz et al. | 623/23.72 |
| 6,478,799 B1 | 11/2002 | Williamson | 606/90 |
| 6,479,996 B1 | 11/2002 | Hoogeveen et al. | 324/309 |
| 6,510,334 B1 | 1/2003 | Schuster et al. | 600/407 |
| 6,520,964 B2 | 2/2003 | Tallarida et al. | 396/567 |
| 6,554,838 B2 | 4/2003 | McGovern et al. | 606/87 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |
| 6,589,281 B2 | 7/2003 | Hyde, Jr. | 623/18.11 |
| 6,620,168 B1 | 9/2003 | Lombardo et al. | 606/88 |
| 6,626,945 B2 | 9/2003 | Simon et al. | 623/17.19 |
| 6,626,948 B2 | 9/2003 | Storer et al. | 623/23.14 |
| 6,632,225 B2 | 10/2003 | Sanford et al. | 606/87 |
| 6,632,235 B2 | 10/2003 | Weikel et al. | 606/192 |
| 6,652,587 B2 | 11/2003 | Felt et al. | 623/20.16 |
| 6,673,077 B1* | 1/2004 | Katz | A61B 17/154 606/102 |
| 6,673,116 B2 | 1/2004 | Reiley | 623/21.18 |
| 6,679,917 B2 | 1/2004 | Ek | 623/20.14 |
| 6,702,821 B2 | 3/2004 | Bonutti | 606/88 |
| 6,712,856 B1 | 3/2004 | Carignan et al. | 623/20.35 |
| 6,770,078 B2 | 8/2004 | Bonutti | 606/88 |
| 6,772,026 B2 | 8/2004 | Bradbury et al. | 700/98 |
| 6,905,514 B2 | 6/2005 | Carignan et al. | 623/20.35 |
| 6,916,341 B2 | 7/2005 | Rolston | 623/20.3 |
| 6,928,742 B2 | 8/2005 | Broers et al. | 33/512 |
| 6,932,842 B1 | 8/2005 | Litschko et al. | 623/16.11 |
| 6,969,393 B2 | 11/2005 | Pinczewski et al. | 606/88 |
| 6,978,188 B1 | 12/2005 | Christensen | 700/118 |
| 6,984,249 B2 | 1/2006 | Keller | 623/20.24 |
| 7,008,430 B2 | 3/2006 | Dong et al. | 606/80 |
| 7,060,074 B2 | 6/2006 | Rosa et al. | 606/88 |
| 7,104,996 B2 | 9/2006 | Bonutti | 606/86 |
| 7,104,997 B2 | 9/2006 | Lionberger et al. | 606/88 |
| 7,115,131 B2 | 10/2006 | Engh et al. | 606/79 |
| 7,117,027 B2 | 10/2006 | Zheng et al. | 600/426 |
| 7,141,053 B2 | 11/2006 | Rosa et al. | 606/86 |
| 7,184,814 B2 | 2/2007 | Lang et al. | 600/416 |
| 7,239,908 B1 | 7/2007 | Alexander et al. | 600/427 |
| 7,245,697 B2 | 7/2007 | Lang | 378/54 |
| 7,282,054 B2 | 10/2007 | Steffensmeier et al. | 606/96 |
| 7,292,674 B2 | 11/2007 | Lang | 378/54 |
| 7,379,529 B2 | 5/2008 | Lang | 378/54 |
| 7,442,196 B2 | 10/2008 | Fisher et al. | 606/88 |
| 7,467,892 B2 | 12/2008 | Lang et al. | 378/207 |
| 7,468,075 B2 | 12/2008 | Lang et al. | 623/16.11 |
| 7,534,263 B2 | 5/2009 | Burdulis, Jr. et al. | 623/14.12 |
| 7,603,192 B2 | 10/2009 | Martin et al. | 700/98 |
| 7,615,054 B1 | 11/2009 | Bonutti | 606/88 |
| 7,618,451 B2 | 11/2009 | Berez et al. | 623/14.12 |
| 7,695,477 B2 | 4/2010 | Creger et al. | 606/87 |
| 7,747,305 B2 | 6/2010 | Dean et al. | 600/407 |
| 7,806,896 B1 | 10/2010 | Bonutti | 606/86 R |
| 7,881,768 B2 | 2/2011 | Lang et al. | 600/407 |
| 7,981,158 B2 | 7/2011 | Fitz et al. | 623/17.16 |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | 606/87 |
| 8,066,708 B2 | 11/2011 | Lang et al. | 606/88 |
| 8,070,752 B2 | 12/2011 | Metzger et al. | 606/88 |
| 8,083,745 B2 | 12/2011 | Lang et al. | 606/87 |
| 8,092,462 B2 | 1/2012 | Pinczewski et al. | 606/88 |
| 8,105,330 B2 | 1/2012 | Fitz et al. | 606/88 |
| 8,109,942 B2 | 2/2012 | Carson | 606/130 |
| 8,112,142 B2 | 2/2012 | Alexander et al. | 600/407 |
| 8,122,582 B2 | 2/2012 | Burdulis, Jr. et al. | 29/527.1 |
| 8,123,753 B2 | 2/2012 | Poncet | 606/87 |
| RE43,282 E | 3/2012 | Alexander et al. | 600/427 |
| 8,160,345 B2 | 4/2012 | Pavlovskaia et al. | 382/131 |
| 8,167,888 B2 | 5/2012 | Steffensmeier | 606/88 |
| 8,221,430 B2 | 7/2012 | Park et al. | 606/88 |
| 8,234,097 B2 | 7/2012 | Steines et al. | 703/1 |
| 8,257,360 B2 | 9/2012 | Richard et al. | 606/88 |
| 8,265,730 B2 | 9/2012 | Alexander et al. | 600/410 |
| 8,282,646 B2 | 10/2012 | Schoenefeld et al. | 606/88 |
| 8,306,601 B2 | 11/2012 | Lang et al. | 600/407 |
| 8,311,306 B2 | 11/2012 | Pavlovskaia et al. | 382/131 |
| 8,333,723 B2 | 12/2012 | Hunter et al. | 602/13 |
| 8,337,501 B2 | 12/2012 | Fitz et al. | 606/86 R |
| 8,337,503 B2 | 12/2012 | Lian | 606/87 |
| 8,337,507 B2 | 12/2012 | Lang et al. | 606/102 |
| 8,343,218 B2 | 1/2013 | Lang et al. | 623/16.11 |
| 8,352,056 B2 | 1/2013 | Lee et al. | 700/97 |
| 8,357,111 B2 | 1/2013 | Caillouette et al. | 602/26 |
| 8,357,166 B2 | 1/2013 | Aram et al. | 606/88 |
| 8,361,076 B2 | 1/2013 | Roose et al. | 606/88 |
| 8,366,771 B2 | 2/2013 | Burdulis, Jr. et al. | 623/14.12 |
| 8,369,926 B2 | 2/2013 | Lang et al. | 600/407 |
| 8,377,066 B2 | 2/2013 | Katrana et al. | 606/86 |
| 8,377,068 B2 | 2/2013 | Aker et al. | 606/87 |
| 8,377,073 B2 | 2/2013 | Wasielewski | 606/102 |
| 8,377,129 B2 | 2/2013 | Fitz et al. | 623/14.12 |
| 8,380,471 B2 | 2/2013 | Iannotti et al. | 703/6 |
| 8,398,646 B2 | 3/2013 | Metzger et al. | 606/88 |

(56) References Cited

U.S. PATENT DOCUMENTS

| | | | |
|---|---|---|---|
| 8,407,067 B2 | 3/2013 | Uthgenannt et al. ............. 705/2 |
| 8,419,740 B2 | 4/2013 | Aram et al. ..................... 606/88 |
| 8,425,524 B2 | 4/2013 | Aker et al. ..................... 606/88 |
| 8,439,926 B2 | 5/2013 | Bojarski et al. ............... 606/88 |
| 8,457,930 B2 | 6/2013 | Schroeder ........................ 703/1 |
| 8,460,304 B2 | 6/2013 | Fitz et al. ..................... 606/88 |
| 8,473,305 B2 | 6/2013 | Belcher et al. .................. 705/2 |
| 8,480,754 B2 | 7/2013 | Bojarski et al. ............ 623/20.35 |
| 8,486,150 B2 | 7/2013 | White et al. ................ 623/20.21 |
| 8,500,740 B2 | 8/2013 | Bojarski et al. ............ 606/86 R |
| 8,529,568 B2 | 9/2013 | Bouadi ........................... 606/84 |
| 8,529,630 B2 | 9/2013 | Bojarski et al. ............ 623/20.14 |
| 8,532,807 B2 | 9/2013 | Metzger ......................... 700/98 |
| 8,545,569 B2 | 10/2013 | Fitz et al. ................ 623/20.14 |
| 8,551,099 B2 | 10/2013 | Lang et al. ................ 606/86 R |
| 8,551,102 B2 | 10/2013 | Fitz et al. ..................... 606/88 |
| 8,551,103 B2 | 10/2013 | Fitz et al. ..................... 606/88 |
| 8,551,169 B2 | 10/2013 | Fitz et al. ................ 623/14.12 |
| 8,556,906 B2 | 10/2013 | Fitz et al. ..................... 606/87 |
| 8,556,907 B2 | 10/2013 | Fitz et al. ..................... 606/87 |
| 8,556,971 B2 | 10/2013 | Lang ........................ 623/14.12 |
| 8,556,983 B2 | 10/2013 | Bojarski et al. ............ 623/20.35 |
| 8,561,278 B2 | 10/2013 | Fitz et al. ................ 29/407.09 |
| 8,562,611 B2 | 10/2013 | Fitz et al. ..................... 606/80 |
| 8,562,618 B2 | 10/2013 | Fitz et al. ..................... 606/88 |
| 8,568,479 B2 | 10/2013 | Fitz et al. ................ 623/14.12 |
| 8,568,480 B2 | 10/2013 | Fitz et al. ................ 623/14.12 |
| 8,585,708 B2 | 11/2013 | Fitz et al. ..................... 606/88 |
| 8,617,172 B2 | 12/2013 | Fitz et al. ..................... 606/88 |
| 8,617,175 B2 | 12/2013 | Park et al. ..................... 606/89 |
| 8,617,242 B2 | 12/2013 | Philipp ..................... 623/16.11 |
| 8,623,026 B2 | 1/2014 | Wong et al. |
| 8,634,617 B2 | 1/2014 | Tsougarakis et al. ........ 382/128 |
| 8,638,998 B2 | 1/2014 | Steines et al. ............... 382/128 |
| 8,641,716 B2 | 2/2014 | Fitz et al. ..................... 606/80 |
| 8,657,827 B2 | 2/2014 | Fitz et al. ..................... 606/87 |
| 8,690,945 B2 | 4/2014 | Fitz et al. |
| 8,709,089 B2 | 4/2014 | Lang et al. ................ 623/18.11 |
| 8,768,028 B2 | 7/2014 | Lang et al. .................. 382/131 |
| 8,801,720 B2 | 8/2014 | Park et al. ..................... 606/88 |
| 8,951,259 B2 | 2/2015 | Fitz et al. ..................... 606/88 |
| 8,951,260 B2 | 2/2015 | Lang et al. .................... 606/88 |
| 8,998,915 B2 | 4/2015 | Fitz et al. |
| 9,023,050 B2 | 5/2015 | Lang et al. .................... 606/82 |
| 9,055,953 B2 | 6/2015 | Lang et al. .................. 606/102 |
| 9,066,728 B2 | 6/2015 | Burdulis, Jr. et al. ..... 623/20.32 |
| 9,072,531 B2 | 7/2015 | Fitz et al. ................ 606/86 R |
| 9,084,617 B2 | 7/2015 | Lang et al. |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. .................... 606/79 |
| 9,125,672 B2 | 9/2015 | Fitz et al. ..................... 606/88 |
| 9,125,673 B2 | 9/2015 | Fitz et al. ..................... 606/87 |
| 9,186,161 B2 | 11/2015 | Lang et al. .................... 606/80 |
| 9,216,025 B2 | 12/2015 | Fitz et al. |
| 9,220,516 B2 | 12/2015 | Lang et al. .................... 606/79 |
| 9,220,517 B2 | 12/2015 | Lang et al. .................... 606/87 |
| 9,241,724 B2 | 1/2016 | Lang et al. .................... 606/79 |
| 9,241,725 B2 | 1/2016 | Lang et al. .................... 606/79 |
| 9,295,481 B2 | 3/2016 | Fitz et al. ..................... 606/79 |
| 9,295,482 B2 | 3/2016 | Fitz et al. |
| 9,308,005 B2 | 4/2016 | Fitz et al. ..................... 606/79 |
| 9,308,053 B2 | 4/2016 | Bojarski et al. |
| 9,314,256 B2 | 4/2016 | Fitz et al. |
| 9,326,780 B2 | 5/2016 | Wong et al. .................... 606/85 |
| 9,333,085 B2 | 5/2016 | Fitz et al. ................ 623/16.11 |
| 9,358,018 B2 | 6/2016 | Fitz et al. |
| 9,375,222 B2 | 6/2016 | Fitz et al. ................... 606/102 |
| 9,381,025 B2 | 7/2016 | Fitz et al. ..................... 606/79 |
| 9,408,615 B2 | 8/2016 | Fitz et al. ..................... 606/87 |
| 9,486,226 B2 | 11/2016 | Chao |
| 2001/0001120 A1 | 5/2001 | Masini ......................... 606/86 |
| 2001/0010023 A1 | 7/2001 | Schwartz et al. .......... 623/23.72 |
| 2001/0039455 A1 | 11/2001 | Simon et al. ............... 623/23.51 |
| 2002/0013626 A1 | 1/2002 | Geistlich et al. .......... 623/23.57 |
| 2002/0029038 A1 | 3/2002 | Haines .......................... 606/54 |
| 2002/0045940 A1 | 4/2002 | Giannetti et al. .......... 623/11.11 |
| 2002/0059049 A1 | 5/2002 | Bradbury et al. ............. 703/11 |
| 2002/0068979 A1 | 6/2002 | Brown et al. ............... 623/20.3 |
| 2002/0072821 A1 | 6/2002 | Baker ........................... 700/98 |
| 2002/0079601 A1 | 6/2002 | Russell et al. ............. 264/40.1 |
| 2002/0082703 A1 | 6/2002 | Repicci ..................... 623/20.29 |
| 2002/0087274 A1 | 7/2002 | Alexander et al. ............ 702/19 |
| 2002/0106625 A1 | 8/2002 | Hung et al. .................. 435/1.1 |
| 2002/0115647 A1 | 8/2002 | Halvorsen et al. ........... 514/171 |
| 2002/0120274 A1 | 8/2002 | Overaker et al. .............. 606/72 |
| 2002/0120281 A1 | 8/2002 | Overaker .................... 606/151 |
| 2002/0127264 A1 | 9/2002 | Felt et al. .................... 424/423 |
| 2002/0133230 A1 | 9/2002 | Repicci ..................... 623/14.12 |
| 2002/0143402 A1 | 10/2002 | Steinberg ................ 623/22.16 |
| 2002/0151986 A1 | 10/2002 | Asculai et al. .............. 424/484 |
| 2002/0156150 A1 | 10/2002 | Williams et al. ............. 523/113 |
| 2002/0173852 A1 | 11/2002 | Felt et al. .................. 623/20.32 |
| 2002/0183850 A1 | 12/2002 | Felt et al. .................. 623/20.16 |
| 2003/0028196 A1 | 2/2003 | Bonutti ......................... 606/87 |
| 2003/0055500 A1 | 3/2003 | Fell et al. .................. 623/14.12 |
| 2003/0055501 A1 | 3/2003 | Fell et al. .................. 623/14.12 |
| 2003/0055502 A1 | 3/2003 | Lang et al. ................ 623/16.11 |
| 2003/0060882 A1 | 3/2003 | Fell et al. .................. 623/14.12 |
| 2003/0060883 A1 | 3/2003 | Fell et al. .................. 623/14.12 |
| 2003/0060884 A1 | 3/2003 | Fell et al. .................. 623/14.12 |
| 2003/0060885 A1 | 3/2003 | Fell et al. .................. 623/14.12 |
| 2003/0069591 A1 | 4/2003 | Carson et al. ............... 606/130 |
| 2003/0100907 A1 | 5/2003 | Rosa et al. ................... 606/86 |
| 2003/0100953 A1 | 5/2003 | Rosa et al. .................. 623/20.3 |
| 2003/0120347 A1 | 6/2003 | Steinberg ................ 623/22.17 |
| 2003/0158558 A1 | 8/2003 | Horn ............................ 606/87 |
| 2003/0158606 A1 | 8/2003 | Coon et al. ............... 623/20.15 |
| 2003/0163137 A1 | 8/2003 | Smucker et al. ............... 606/87 |
| 2003/0173695 A1 | 9/2003 | Monkhouse et al. ........ 264/40.1 |
| 2003/0216669 A1 | 11/2003 | Lang et al. .................. 600/587 |
| 2003/0225457 A1 | 12/2003 | Justin et al. .............. 623/20.14 |
| 2003/0236521 A1 | 12/2003 | Brown et al. ................. 606/80 |
| 2004/0098133 A1 | 5/2004 | Carignan et al. .......... 623/20.35 |
| 2004/0102852 A1 | 5/2004 | Johnson et al. ........... 623/20.15 |
| 2004/0102866 A1 | 5/2004 | Harris et al. ............. G06F 19/00 |
| 2004/0117015 A1 | 6/2004 | Biscup ....................... 623/16.11 |
| 2004/0122521 A1 | 6/2004 | Lee et al. .................. 623/20.15 |
| 2004/0133276 A1 | 7/2004 | Lang et al. ................ 623/14.12 |
| 2004/0138754 A1 | 7/2004 | Lang et al. ................ 623/20.14 |
| 2004/0147927 A1 | 7/2004 | Tsougarakis et al. .......... 606/53 |
| 2004/0153079 A1 | 8/2004 | Tsougarakis et al. .......... 606/77 |
| 2004/0153162 A1 | 8/2004 | Sanford et al. ............. 623/20.3 |
| 2004/0153164 A1 | 8/2004 | Sanford et al. ........... 623/20.29 |
| 2004/0167390 A1 | 8/2004 | Alexander et al. ........... 600/410 |
| 2004/0167630 A1 | 8/2004 | Rolston ..................... 623/20.14 |
| 2004/0193280 A1 | 9/2004 | Webster et al. ............ 623/20.33 |
| 2004/0204644 A1 | 10/2004 | Tsougarakis et al. ........ 600/410 |
| 2004/0204760 A1 | 10/2004 | Fitz et al. ................ 623/14.12 |
| 2004/0236424 A1* | 11/2004 | Berez ................... A61B 5/1076 623/14.12 |
| 2004/0249386 A1 | 12/2004 | Faoro ............................ 606/88 |
| 2005/0015153 A1 | 1/2005 | Goble et al. ............... 623/23.46 |
| 2005/0021039 A1 | 1/2005 | Cusick et al. .................. 606/88 |
| 2005/0043807 A1 | 2/2005 | Wood ........................ 623/20.14 |
| 2005/0055028 A1 | 3/2005 | Haines ........................... 606/79 |
| 2005/0085920 A1 | 4/2005 | Williamson ............... 623/20.14 |
| 2005/0107883 A1 | 5/2005 | Goodfried et al. ........ 623/20.15 |
| 2005/0107884 A1 | 5/2005 | Johnson et al. ........... 623/20.15 |
| 2005/0107886 A1 | 5/2005 | Crabtree et al. ........... 623/20.24 |
| 2005/0119664 A1 | 6/2005 | Carignan et al. ............... 606/96 |
| 2005/0143745 A1 | 6/2005 | Hodorek et al. ............... 606/87 |
| 2005/0148843 A1 | 7/2005 | Roose ........................... 600/407 |
| 2005/0171545 A1 | 8/2005 | Walsh et al. ................... 606/72 |
| 2005/0171612 A1 | 8/2005 | Rolston ..................... 623/20.19 |
| 2005/0192588 A1 | 9/2005 | Garcia ............................ 606/88 |
| 2005/0197814 A1 | 9/2005 | Aram et al. .................. 703/11 |
| 2005/0216305 A1 | 9/2005 | Funderud ....................... 705/2 |
| 2005/0234461 A1 | 10/2005 | Burdulis, Jr. et al. .......... 606/79 |
| 2005/0267584 A1 | 12/2005 | Burdulis et al. ........... 623/20.19 |
| 2005/0278034 A1 | 12/2005 | Johnson et al. ........... 623/20.15 |
| 2006/0052795 A1 | 3/2006 | White ......................... 606/102 |
| 2006/0069318 A1 | 3/2006 | Keavney et al. ............. 600/300 |

(56) References Cited

U.S. PATENT DOCUMENTS

| | | | |
|---|---|---|---|
| 2006/0094951 A1 | 5/2006 | Dean et al. | 600/407 |
| 2006/0111722 A1 | 5/2006 | Bouadi | 606/79 |
| 2006/0111726 A1 | 5/2006 | Felt et al. | 606/86 |
| 2006/0122616 A1 | 6/2006 | Bennett et al. | 606/87 |
| 2006/0149283 A1 | 7/2006 | May et al. | 606/96 |
| 2006/0200162 A1 | 9/2006 | Farling et al. | 606/88 |
| 2006/0235421 A1 | 10/2006 | Rosa et al. | 606/88 |
| 2007/0015995 A1 | 1/2007 | Lang | 600/407 |
| 2007/0073305 A1 | 3/2007 | Lionberger et al. | 606/87 |
| 2007/0118141 A1 | 5/2007 | Marchyn et al. | 606/88 |
| 2007/0198022 A1 | 8/2007 | Lang et al. | 606/88 |
| 2007/0203430 A1 | 8/2007 | Lang et al. | 600/587 |
| 2007/0226986 A1 | 10/2007 | Park et al. | 29/592 |
| 2007/0233141 A1 | 10/2007 | Park et al. | 606/88 |
| 2007/0233151 A1 | 10/2007 | Chudik | 606/96 |
| 2007/0233156 A1 | 10/2007 | Metzger | 606/130 |
| 2007/0239165 A1 | 10/2007 | Amirouche | 606/86 |
| 2007/0276224 A1 | 11/2007 | Lang et al. | 600/410 |
| 2007/0276501 A1 | 11/2007 | Betz et al. | 623/17.16 |
| 2007/0282451 A1 | 12/2007 | Metzger et al. | 623/20.28 |
| 2007/0288030 A1 | 12/2007 | Metzger et al. | 606/87 |
| 2007/0288032 A1* | 12/2007 | Metzger | A61B 17/025 606/99 |
| 2007/0293868 A1 | 12/2007 | Delfosse et al. | 606/88 |
| 2008/0004709 A1 | 1/2008 | O'Neill et al. | 623/20.35 |
| 2008/0015433 A1 | 1/2008 | Alexander et al. | 600/427 |
| 2008/0021566 A1 | 1/2008 | Peters et al. | 623/20.16 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1 | 3/2008 | Hajaj et al. | 623/20.14 |
| 2008/0114370 A1 | 5/2008 | Schoenefeld | 606/96 |
| 2008/0140212 A1 | 6/2008 | Metzger et al. | 623/20.31 |
| 2008/0147072 A1 | 6/2008 | Park et al. | 606/87 |
| 2008/0170659 A1 | 7/2008 | Lang et al. | 378/56 |
| 2008/0195216 A1 | 8/2008 | Philipp | 623/18.11 |
| 2008/0215059 A1 | 9/2008 | Carignan et al. | 606/96 |
| 2008/0219412 A1 | 9/2008 | Lang | 378/207 |
| 2008/0243127 A1 | 10/2008 | Lang et al. | 606/87 |
| 2008/0257363 A1 | 10/2008 | Schoenefeld et al. | 128/897 |
| 2008/0262624 A1 | 10/2008 | White et al. | 623/20.32 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Fitz et al. | 623/17.16 |
| 2008/0281426 A1 | 11/2008 | Fitz et al. | 623/17.16 |
| 2008/0319448 A1 | 12/2008 | Lavallee et al. | 606/102 |
| 2009/0024131 A1 | 1/2009 | Metzger et al. | 606/88 |
| 2009/0076371 A1 | 3/2009 | Lang et al. | 600/407 |
| 2009/0087276 A1 | 4/2009 | Rose | 409/79 |
| 2009/0088753 A1 | 4/2009 | Aram et al. | 606/79 |
| 2009/0088758 A1 | 4/2009 | Bennett | 606/82 |
| 2009/0099567 A1 | 4/2009 | Zajac | 606/79 |
| 2009/0110498 A1 | 4/2009 | Park | 408/1 R |
| 2009/0131941 A1 | 5/2009 | Park et al. | 606/87 |
| 2009/0131942 A1 | 5/2009 | Aker et al. | 606/86 |
| 2009/0138020 A1 | 5/2009 | Park et al. | 606/88 |
| 2009/0151736 A1 | 6/2009 | Belcher et al. | 128/898 |
| 2009/0163922 A1 | 6/2009 | Meridew et al. | 606/88 |
| 2009/0222014 A1 | 9/2009 | Bojarski et al. | 606/88 |
| 2009/0226068 A1 | 9/2009 | Fitz et al. | 382/131 |
| 2009/0254093 A1 | 10/2009 | White et al. | 606/89 |
| 2009/0270868 A1 | 10/2009 | Park et al. | 606/87 |
| 2009/0307893 A1 | 12/2009 | Burdulis, Jr. et al. | 29/527.1 |
| 2009/0326666 A1 | 12/2009 | Wyss et al. | 623/20.29 |
| 2010/0042105 A1 | 2/2010 | Park et al. | 606/87 |
| 2010/0049195 A1 | 2/2010 | Park et al. | 606/87 |
| 2010/0082035 A1 | 4/2010 | Keefer | 606/97 |
| 2010/0087829 A1 | 4/2010 | Metzger et al. | 606/96 |
| 2010/0152741 A1 | 6/2010 | Park et al. | 606/87 |
| 2010/0160917 A1 | 6/2010 | Fitz et al. | 606/88 |
| 2010/0168754 A1 | 7/2010 | Fitz et al. | 606/88 |
| 2010/0256479 A1 | 10/2010 | Park et al. | 600/410 |
| 2010/0274534 A1 | 10/2010 | Steines et al. | 703/1 |
| 2010/0281678 A1 | 11/2010 | Burdulis, Jr. et al. | 29/592 |
| 2010/0292963 A1 | 11/2010 | Schroeder | 703/1 |
| 2010/0298894 A1 | 11/2010 | Bojarski et al. | 606/86 R |
| 2010/0303313 A1 | 12/2010 | Lang et al. | 382/128 |
| 2010/0305573 A1 | 12/2010 | Fitz et al. | 606/87 |
| 2010/0305574 A1 | 12/2010 | Fitz et al. | 606/88 |
| 2010/0305575 A1* | 12/2010 | Wilkinson | A61B 17/155 606/88 |
| 2010/0331991 A1 | 12/2010 | Wilkinson et al. | 623/20.32 |
| 2010/0332194 A1 | 12/2010 | McGuan et al. | 703/1 |
| 2011/0029093 A1 | 2/2011 | Bojarski et al. | 623/20.35 |
| 2011/0040387 A1 | 2/2011 | Ries et al. | 623/20.27 |
| 2011/0046735 A1 | 2/2011 | Metzger et al. | 623/14.12 |
| 2011/0054478 A1 | 3/2011 | Vanasse et al. | 606/87 |
| 2011/0066193 A1 | 3/2011 | Lang et al. | 606/86 R |
| 2011/0071533 A1 | 3/2011 | Metzger et al. | 606/88 |
| 2011/0071581 A1 | 3/2011 | Lang et al. | 606/86 R |
| 2011/0092804 A1 | 4/2011 | Schoenefeld et al. | 600/416 |
| 2011/0093108 A1 | 4/2011 | Ashby et al. | 700/103 |
| 2011/0125009 A1 | 5/2011 | Lang et al. | 600/425 |
| 2011/0166578 A1 | 7/2011 | Stone et al. | 606/88 |
| 2011/0190899 A1 | 8/2011 | Pierce et al. | 623/20.32 |
| 2011/0213368 A1 | 9/2011 | Fitz et al. | 606/80 |
| 2011/0213373 A1 | 9/2011 | Fitz et al. | 606/87 |
| 2011/0213374 A1 | 9/2011 | Fitz et al. | 606/87 |
| 2011/0213377 A1 | 9/2011 | Lang et al. | 606/89 |
| 2011/0213427 A1 | 9/2011 | Fitz et al. | 606/86 R |
| 2011/0213428 A1 | 9/2011 | Fitz et al. | 606/86 R |
| 2011/0213429 A1 | 9/2011 | Lang et al. | 606/86 R |
| 2011/0213430 A1 | 9/2011 | Lang et al. | 606/86 R |
| 2011/0213431 A1 | 9/2011 | Fitz et al. | 606/86 R |
| 2011/0218539 A1 | 9/2011 | Fitz et al. | 606/87 |
| 2011/0218542 A1 | 9/2011 | Lian | 606/88 |
| 2011/0218545 A1 | 9/2011 | Catanzarite et al. | 606/96 |
| 2011/0218584 A1 | 9/2011 | Fitz et al. | 606/86 R |
| 2011/0230888 A1 | 9/2011 | Lang et al. | 606/87 |
| 2011/0238073 A1 | 9/2011 | Lang et al. | 606/89 |
| 2011/0295329 A1 | 12/2011 | Fitz et al. | 606/86 R |
| 2011/0313423 A1 | 12/2011 | Lang et al. | 606/87 |
| 2011/0319897 A1 | 12/2011 | Lang et al. | 606/79 |
| 2011/0319900 A1 | 12/2011 | Lang et al. | 606/87 |
| 2012/0029520 A1 | 2/2012 | Lang et al. | 606/89 |
| 2012/0041446 A1 | 2/2012 | Wong et al. | 606/96 |
| 2012/0066892 A1 | 3/2012 | Lang et al. | 29/592 |
| 2012/0071881 A1 | 3/2012 | Lang et al. | 606/87 |
| 2012/0071882 A1 | 3/2012 | Lang et al. | 606/88 |
| 2012/0071883 A1 | 3/2012 | Lang et al. | 606/88 |
| 2012/0072185 A1 | 3/2012 | Lang et al. | 703/1 |
| 2012/0078598 A1 | 3/2012 | McDaniel | 703/6 |
| 2012/0101503 A1 | 4/2012 | Lang et al. | 606/87 |
| 2012/0123422 A1 | 5/2012 | Agnihotri et al. | 606/89 |
| 2012/0141034 A1 | 6/2012 | Iannotti et al. | 382/199 |
| 2012/0143197 A1 | 6/2012 | Lang et al. | 606/87 |
| 2012/0151730 A1 | 6/2012 | Fitz et al. | 29/407.01 |
| 2012/0158001 A1 | 6/2012 | Burdulis, Jr. et al. | 606/88 |
| 2012/0197260 A1 | 8/2012 | Fitz et al. | 606/86 |
| 2012/0209394 A1 | 8/2012 | Bojarski et al. | 623/20.32 |
| 2012/0239045 A1 | 9/2012 | Li | 606/88 |
| 2012/0265496 A1 | 10/2012 | Mahfouz | 703/1 |
| 2012/0276509 A1 | 11/2012 | Iannotti et al. | 434/267 |
| 2012/0289966 A1 | 11/2012 | Fitz et al. | 606/88 |
| 2012/0296337 A1 | 11/2012 | Fitz et al. | 606/80 |
| 2012/0310364 A1 | 12/2012 | Li et al. | 623/23.55 |
| 2012/0316564 A1 | 12/2012 | Serbousek et al. | 606/80 |
| 2012/0323246 A1 | 12/2012 | Catanzarite et al. | 606/88 |
| 2013/0006250 A1 | 1/2013 | Metzger et al. | 606/87 |
| 2013/0006251 A1 | 1/2013 | Aram et al. | 606/88 |
| 2013/0018378 A1 | 1/2013 | Hananouchi et al. | 606/87 |
| 2013/0018379 A1 | 1/2013 | Fitz et al. | 606/87 |
| 2013/0018380 A1 | 1/2013 | Fitz et al. | 623/14.12 |
| 2013/0018464 A1 | 1/2013 | Fitz et al. | 606/88 |
| 2013/0023884 A1 | 1/2013 | Fitz et al. | 623/20.14 |
| 2013/0024000 A1 | 1/2013 | Bojarski et al. | 623/20.14 |
| 2013/0030419 A1 | 1/2013 | Fitz et al. | 606/1 |
| 2013/0030441 A1 | 1/2013 | Fitz et al. | 606/87 |
| 2013/0035766 A1 | 2/2013 | Meridew | 623/22.21 |
| 2013/0066319 A1 | 3/2013 | Aram et al. | 606/60 |
| 2013/0066321 A1 | 3/2013 | Mannss et al. | 606/88 |
| 2013/0079781 A1 | 3/2013 | Fitz et al. | 606/80 |
| 2013/0079876 A1 | 3/2013 | Fitz et al. | 623/14.12 |
| 2013/0081247 A1 | 4/2013 | Fitz et al. | 29/407.09 |

(56) References Cited

U.S. PATENT DOCUMENTS

| | | | |
|---|---|---|---|
| 2013/0096562 A1 | 4/2013 | Fitz et al. | 606/88 |
| 2013/0110116 A1 | 5/2013 | Kehres et al. | 606/96 |
| 2013/0119579 A1 | 5/2013 | Iannotti et al. | 264/256 |
| 2013/0123792 A1 | 5/2013 | Fitz et al. | 606/96 |
| 2013/0138111 A1 | 5/2013 | Aram et al. | 606/88 |
| 2013/0184713 A1 | 7/2013 | Bojarski et al. | 606/88 |
| 2013/0184764 A1 | 7/2013 | Stone et al. | 606/280 |
| 2013/0199259 A1 | 8/2013 | Smith | 72/362 |
| 2013/0211409 A1 | 8/2013 | Burdulis, Jr. et al. | 606/88 |
| 2013/0253522 A1 | 9/2013 | Bojarski et al. | 606/88 |
| 2013/0289570 A1 | 10/2013 | Chao | 606/88 |
| 2013/0296874 A1 | 11/2013 | Chao | 606/88 |
| 2013/0297031 A1 | 11/2013 | Hafez | 623/20.14 |
| 2013/0317511 A1 | 11/2013 | Bojarski et al. | 606/102 |
| 2013/0331850 A1 | 12/2013 | Bojarski et al. | 606/102 |
| 2014/0018813 A1 | 1/2014 | McKinnon et al. | 606/88 |
| 2014/0025348 A1 | 1/2014 | Abiven et al. | 703/1 |
| 2014/0031826 A1 | 1/2014 | Bojarski et al. | 606/88 |
| 2014/0058396 A1 | 2/2014 | Fitz et al. | 606/87 |
| 2014/0058397 A1 | 2/2014 | Fitz et al. | 606/88 |
| 2014/0066935 A1 | 3/2014 | Fitz et al. | 606/87 |
| 2014/0066936 A1 | 3/2014 | Fitz et al. | 606/87 |
| 2014/0074441 A1 | 3/2014 | Fitz et al. | 703/1 |
| 2014/0107715 A1 | 4/2014 | Heilman et al. | 606/86 R |
| 2014/0180295 A1 | 6/2014 | Buza et al. | 606/87 |
| 2014/0324205 A1 | 10/2014 | Park et al. | 700/98 |
| 2015/0150644 A1 | 6/2015 | Lang et al. | |
| 2016/0045317 A1 | 2/2016 | Lang et al. | |
| 2016/0074124 A1 | 3/2016 | Fitz et al. | |

FOREIGN PATENT DOCUMENTS

| | | | | |
|---|---|---|---|---|
| DE | 3516743 | 11/1986 | | A61F 2/36 |
| DE | 44 34 539 | 4/1996 | | A61F 2/38 |
| DE | 20303498 | 8/2003 | | A61B 17/15 |
| EP | 0337901 | 10/1989 | | A61B 17/14 |
| EP | 0528080 | 2/1993 | | A61F 2/30 |
| EP | 0 704 193 | 4/1996 | | A61F 2/30 |
| EP | 0732092 A2 | 9/1996 | | A61F 2/38 |
| EP | 0626156 | 7/1997 | | A61F 2/38 |
| EP | 0908836 | 4/1999 | | G06F 19/00 |
| EP | 0613380 | 12/1999 | | A61L 27/00 |
| EP | 0993807 | 4/2000 | | A61B 17/17 |
| EP | 1074229 | 2/2001 | | A61F 2/38 |
| EP | 1077253 | 2/2001 | | C12N 5/00 |
| EP | 1120087 | 8/2001 | | A61B 17/06 |
| EP | 1129675 | 9/2001 | | A61F 2/30 |
| EP | 1132061 | 9/2001 | | A61F 2/28 |
| EP | 0732091 | 12/2001 | | A61F 2/38 |
| EP | 0896825 | 7/2002 | | A61L 27/00 |
| EP | 0814731 | 8/2002 | | A61F 2/30 |
| EP | 1234552 | 8/2002 | | A61F 2/00 |
| EP | 1234555 | 8/2002 | | A61F 2/30 |
| EP | 0809987 | 10/2002 | | A61F 2/38 |
| EP | 0833620 | 10/2002 | | A61K 9/22 |
| EP | 0530804 | 6/2004 | | A61L 25/00 |
| FR | 2819714 | 7/2002 | | A61F 2/44 |
| FR | 2918554 | 1/2009 | | A61B 17/17 |
| GB | 1451283 | 9/1976 | | A61F 1/24 |
| GB | 2291355 | 1/1996 | | A61F 2/38 |
| GB | 2348373 | 10/2000 | | A61F 2/38 |
| JP | 1-249049 | 10/1989 | | A61F 2/38 |
| JP | 8-173465 | 7/1996 | | A61F 2/38 |
| JP | 9-206322 | 8/1997 | | A61F 2/38 |
| JP | 2002-102236 | 4/2002 | | A61B 17/16 |
| WO | WO 87/02882 | 5/1987 | | A61F 2/38 |
| WO | WO 90/09769 | 9/1990 | | A61F 2/28 |
| WO | WO 93/04710 | 3/1993 | | A61L 25/00 |
| WO | WO 93/09819 | 5/1993 | | A61L 27/00 |
| WO | WO 93/25157 | 12/1993 | | A61B 17/57 |
| WO | WO 94/00056 A1 | 1/1994 | | A61B 17/14 |
| WO | WO 95/27450 | 10/1995 | | A61F 2/38 |
| WO | WO 95/28688 | 10/1995 | | G06T 15/00 |
| WO | WO 95/30390 | 11/1995 | | A61F 2/38 |
| WO | WO 95/32623 | 12/1995 | | A01N 1/02 |
| WO | WO 96/24302 | 8/1996 | | A61B 17/90 |
| WO | WO 97/25942 | 7/1997 | | A61F 2/32 |
| WO | WO 97/26847 | 7/1997 | | A61F 2/44 |
| WO | WO 97/27885 | 8/1997 | | A61L 27/00 |
| WO | WO 97/38676 | 10/1997 | | A61K 9/10 |
| WO | WO 98/12994 | 4/1998 | | A61F 2/28 |
| WO | WO 98/20816 | 5/1998 | | A61F 2/38 |
| WO | WO 98/30617 | 7/1998 | | C08G 63/12 |
| WO | WO 98/32384 | 7/1998 | | A61B 17/58 |
| WO | WO 99/02654 | 1/1999 | | C12N 5/00 |
| WO | WO 99/08598 | 2/1999 | | A61B 8/00 |
| WO | WO 99/08728 | 2/1999 | | A61L 27/00 |
| WO | WO 99/32045 A1 | 7/1999 | | A61C 13/00 |
| WO | WO 99/40864 | 8/1999 | | A61B 17/56 |
| WO | WO 99/42061 | 8/1999 | | A61F 2/38 |
| WO | WO 99/47186 | 9/1999 | | A61L 27/00 |
| WO | WO 99/51719 | 10/1999 | | C12M 3/00 |
| WO | WO 99/56674 | 11/1999 | | A61F 2/36 |
| WO | WO 00/09179 | 2/2000 | | A61L 25/00 |
| WO | WO 00/15153 | 3/2000 | | A61F 2/38 |
| WO | WO 00/19911 | 4/2000 | | A61B 17/02 |
| WO | WO 00/35346 | 6/2000 | | A61B 5/11 |
| WO | WO 00/47103 A2 | 8/2000 | | |
| WO | WO 00/48550 | 8/2000 | | |
| WO | WO 00/59411 | 10/2000 | | A61F 2/38 |
| WO | WO 00/68749 A1 | 11/2000 | | G05B 19/4099 |
| WO | WO 00/74554 | 12/2000 | | |
| WO | WO 01/10356 | 2/2001 | | A61F 2/46 |
| WO | WO 01/17463 | 3/2001 | | A61F 2/30 |
| WO | WO 01/19254 | 3/2001 | | A61B 17/00 |
| WO | WO 01/35968 | 5/2001 | | A61K 35/00 |
| WO | WO 01/45764 | 6/2001 | | A61L 27/36 |
| WO | WO 01/66021 | 9/2001 | | A61B 17/14 |
| WO | WO 01/68800 | 9/2001 | | C12M 3/00 |
| WO | WO 01/70142 | 9/2001 | | A61F 2/38 |
| WO | WO 01/77988 A2 | 10/2001 | | G06F 19/00 |
| WO | WO 01/91672 | 12/2001 | | A61F 2/36 |
| WO | WO 02/00270 | 1/2002 | | A61L 27/14 |
| WO | WO 02/00275 | 1/2002 | | A61L 31/14 |
| WO | WO 02/02021 A2 | 1/2002 | | A61B 17/56 |
| WO | WO 02/02158 | 1/2002 | | A61L 27/14 |
| WO | WO 02/22013 | 3/2002 | | A61B 5/055 |
| WO | WO 02/22014 | 3/2002 | | A61B 5/055 |
| WO | WO 02/23483 | 3/2002 | | G06T 11/00 |
| WO | WO 02/34310 | 5/2002 | | A61L 31/04 |
| WO | WO 02/36147 | 5/2002 | | A61K 31/04 |
| WO | WO 02/061688 | 8/2002 | | G06T 17/00 |
| WO | WO 02/096268 | 12/2002 | | |
| WO | WO 03/007788 | 1/2003 | | |
| WO | WO 03/037192 | 5/2003 | | A61B 17/15 |
| WO | WO 03/047470 | 6/2003 | | A61F 2/34 |
| WO | WO 03/051210 | 6/2003 | | A61B 17/58 |
| WO | WO 03/055400 | 7/2003 | | A61B 17/74 |
| WO | WO 2004/043305 | 5/2004 | | A61F 2/30 |
| WO | WO 2004/049981 | 6/2004 | | A61F 2/46 |
| WO | WO 2005/051239 | 6/2005 | | A61F 2/08 |
| WO | WO 2005/051240 | 6/2005 | | A61F 2/08 |
| WO | WO 2006/060795 | 6/2006 | | A61B 17/17 |
| WO | WO 2006/127283 | 11/2006 | | A61B 17/17 |
| WO | WO 2007/041375 | 4/2007 | | A61F 2/38 |
| WO | WO 2007/092841 | 8/2007 | | A61B 17/15 |
| WO | WO 2008/021494 | 2/2008 | | G06F 19/00 |
| WO | WO 2008/112996 | 9/2008 | | A61B 17/15 |
| WO | WO 2008/117028 | 10/2008 | | A61B 17/15 |
| WO | WO 2008/157412 | 12/2008 | | A61B 17/17 |
| WO | WO 2009/001083 | 12/2008 | | A61B 17/15 |
| WO | WO 2009/009660 | 1/2009 | | A61F 2/30 |
| WO | WO 2009/106366 | 9/2009 | | A61B 17/15 |
| WO | WO 2009/106816 | 9/2009 | | A61B 19/00 |
| WO | WO 2009/111639 | 9/2009 | | A61B 17/58 |
| WO | WO 2010/099353 A1 | 9/2010 | | A61F 2/30 |
| WO | WO 2010/121147 | 10/2010 | | A61B 17/90 |
| WO | WO 2010/148103 | 12/2010 | | A61B 17/17 |
| WO | WO 2011/059641 | 5/2011 | | A61B 17/15 |
| WO | WO 2011/101474 | 8/2011 | | G06F 19/00 |
| WO | WO 2011/130421 | 10/2011 | | A61B 17/56 |
| WO | WO 2012/021241 | 2/2012 | | A61B 17/88 |
| WO | WO 2012/021846 | 2/2012 | | A61B 17/90 |
| WO | WO 2012/021894 | 2/2012 | | A61F 2/46 |

(56) References Cited

FOREIGN PATENT DOCUMENTS

| WO | WO 2012/021895 | 2/2012 | ............... A61F 2/46 |
|---|---|---|---|
| WO | WO 2012/027150 | 3/2012 | ............. G06F 19/00 |
| WO | WO 2012/051542 | 4/2012 | ............. A61B 17/16 |
| WO | WO 2012/112694 | 8/2012 | ............... A61B 6/00 |
| WO | WO 2012/112698 | 8/2012 | ............... A61F 2/30 |
| WO | WO 2012/112701 | 8/2012 | ............... A61F 2/30 |
| WO | WO 2012/112702 | 8/2012 | ............... A61F 2/30 |
| WO | WO 2012/173929 | 12/2012 | ............. A61B 17/15 |
| WO | WO 2013/055617 | 4/2013 | ............. A61B 17/15 |
| WO | WO 2013/062850 | 5/2013 | ............... A61F 2/30 |
| WO | WO 2013/119865 | 8/2013 | ............. A61B 17/90 |
| WO | WO 2013/173926 | 11/2013 | ............. A61B 17/17 |
| WO | WO 2014/070889 | 5/2014 | ............. A61B 17/17 |
| WO | WO 2014/145267 A1 | 9/2014 | ............... A61F 2/02 |

OTHER PUBLICATIONS

Argenson et al., "Is There a Place for Patellofemoral Arthroplasty?," Clinical Orthopaedics and Related Research No. 321, pp. 162-167 (1995).

Birnbaum et al., "Computer-Assisted Orthopedic Surgery With Individual Templates and Comparison to Conventional Operation Method", Spine, vol. 26, No. 4, pp. 365-369, Feb. 2001.

Blum et al., "Knee Arthroplasty in Patients with Rheumatoid Arthritis," ANN. Rheum. Dis. 33 (1): 1-11 (1974).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).

Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).

Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).

Cameron, et al., "Review of a Failed Knee Replacement and Some Observations on the Design of a Knee Resurfacing Prosthesis," Arch. Orthop Trauma Surg. 97(2):87-89 (1980).

CAOS, "MIS meets CAOS Spring 2005 Symposium Schedule", *CAOS Spring 2005 Symposium*, pp. 1-9, May 19, 2005.

Carr et al., "Surface Interpolation with Radial Basis Functions for Medical Imaging," IEEE Transactions on Medical Imaging, IEEE, Inc. New York, vol. 16, pp. 96-107 (Feb. 1997).

Chelule et al., "Patient-Specific Template to Preserve Bone Stock in Total Knee Replacement: Preliminary Results", *15th Annual ISTA Symposium*, Sep. 2002, 1 page.

Chelule et al., "Computer Aided Design of Personalized Jigs in Total Knee Replacement", 3rd Annual Meeting of CAOS Int'l Proc., Spain, Jun. 18, 21, 2003, pp. 58-59.

Clary et al., "Experience with the MacIntosh Knee Prosthesis," South Med. J. 65(3):265-272 (1972).

Cohen et al., "Computer-Aided Planning of Patellofemoral Joint OA Surgery: Developing Physical Models from Patient MRI", MICCAI, Oct. 11-13, 1998, 13 pages.

Cohen et al., "Knee Cartilage Topography Thickness and Contact Areas From MRI: In-Vitro Calibration and In-Vivo Measurements", Osteoarthritis and Cartilage vol. 7, No. 1, pp. 95-109 (1999).

Conaty, et al., "Surgery of the Hip and Knee in Patients with Rheumatoid Arthritis," J. Bone Joint Surg. Am. 55(2):301-314 (1973).

De Winter et al., "The Richards Type II Patellofemoral Arthroplasty", Acta Orthop Scand 2001; 72 (5): 487-490.

Delp et al., "A Graphics-Based Software System to Develop and Analyze Models of Musculoskeletal Structures," Comput. Biol. Med., vol. 25, No. 1, pp. 21-34, 1995.

Farrar et al., "Computed Tomography Scan Scout Film for Measurement of Femoral Axis in Knee Arthroplasty," J. Arthroplasty, vol. 14, No. 8, pp. 1030-1031, 1999.

Froemel et al., "Computer Assisted Template Based Navigation for Total Knee Replacement", Documents presented at CAOS on Jun. 17, 2001, 4 pages.

Ghelman et al., "Kinematics of the Knee After Prosthetic Replacements", Clin. Orthop. May 1975: (108): 149-157.

Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).

Hafez et al., "Computer-assisted Total Knee Arthroplasty Using Patient-specific Templating," *Clinical Orthopaedics and Related Research*, No. 444, pp. 184-192 (Mar. 2006).

Hafez et al., "Computer Assisted Total Knee Replacement: Could a Two-Piece Custom Template Replace the Complex Conventional Instrumentations?", 4th Annual Meeting of CAOS Int'l Proc., Chicago, Jun. 16-19, 2004, pp. 63-64.

Hafez et al., "Computer-Assisted Total Hip Arthroplasty: The Present and the Future", Future Rheumatol., vol. 1, pp. 121-131, 2006.

Hastings et al., "Double Hemiarthroplasty of the Knee in Rheumatoid Arthritis," A Survey of Fifty Consecutive Cases, J. Bone Joint Surg. Br. 55(1):112-118 (1973).

Henderson et al., "Experience with the Use of the Macintosh Prosthesis in Knees of Patients with Pheumatoid Arthritis," South. Med. J. 62(11):1311-1315 (1969).

Jessop et al., "Follow-up of the MacIntosh Arthroplasty of the Knee Joint," Rheumatol Phys. Med. 11(5):217-224 (1972).

Kates, et al., "Experiences of Arthroplasty of the Rheumatoid Knee Using MacIntosh Prostheses," Ann. Rheum. Dis. 28(3):328 (1969).

Kay et al., The Macintosh Tibial Plateau Hemiprosthesis for the Rheumatoid Knee, J. Bone Joint Surg. Br. 54(2):256-262 (1972).

Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).

Kim et al., "Measurement of Femoral Neck Anteversion in 3D. Part 1: 3D Imaging Method," Med. and. Viol. Eng. and Computing, vol. 38, No. 6, pp. 603-609, 2000.

Kshirsagar et al., "Measurement of Localized Cartilage Volume and Thickness of Human Knee Joints by Computer Analysis of Three-Dimensional Magnetic Resonance Images", Invest Radiol. May 1998, 33(5): 289-299 T. 111, V. 111.

Lam et al., "X-Ray Diagnosis: A Physician's Approach", Editor Lam, 1998, Springer-Verlag publishers, Title page and Table of Contents pages only (ISBN 9813083247).

Lam et al., "Varus/Valgus Alignment of the Femoral Component in Total Knee Arthroplasty," The Knee, vol. 10, pp. 237-241, 2003.

Leenslag et al., "A Porous Composite for Reconstruction of Meniscus Lesions," Biological and Biomechanical Perform. of Biomaterials, Elsevier Science Publishers Amsterdam pp. 147-152 (1986).

Lu et al., "In vitro degradation of porous poly(L-lactic acid) foams", Biomaterials, 21(15):1595-1605, Aug. 2000.

Macdonald et al., "Inaccuracy of Acetabular Reaming Under Surgical Conditions", Journ. of Arthro., vol. 14, No. 6, pp. 730-737, 1999.

MacIntosh, "Arthroplasty of the Knee in Rheumatoid Arthritis," Proceedings and Reports of Councils and Assotions, J. Bone & Joint Surg., vol. 48B No. (1): 179 (Feb. 1966).

MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).

MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).

(56) References Cited

OTHER PUBLICATIONS

MacIntosh, "Hemiarthroplasty of the Knee Using a Space Occupying Prosthesis for Painful Varus and Valgus Deformities," J. Bone Joint Surg. Am. Dec. 1958:40-A:1431.
Mahaisavariya et al., "Morphological Study of the Proximal Femur: A New Method of Geometrical Assessment Using 3 Dimensional Reverse Engineering," Med. Eng. and Phys., vol. 24, pp. 617-622, 2002.
Marler et al., "Soft-Tissue Augmentation with Injectable Alginate and Syngeneic Fibroblasts", Plastic & Reconstructive Surgery, 105(6):2049-2058, May 2000.
Matsen, III et al. "Robotic Assistance in Orthopaedic Surgery: A Proof of Principle Using Distal Femoral Arthroplasty", Clinical Ortho. and Related Research, 296:178-186 (1993).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Müller-Wittig et al., "A Computer-Assisted Planning System for Total Knee Replacement", CG Topics, pp. 17-19, Jun. 2000.
Nelson et al., "Arthroplasty and Arthrodesis of the Knee Joint," Orthop. Clin. North Am. 2 (1): 245-64 (1971).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Portheine et al., In German: "Potentials of CT-based Planning and Template-based Procedure in Hip and Knee Surgery", Orth. Prac., vol. 36, pp. 786-791, 2000.
Portheine et al., English Translation with Certification: "Potentials of CT-based Planning and Template-based Procedure in Hip and Knee Surgery", Orth. Prac., vol. 36, pp. 786-791, 2000.
Portheine, In German: "Model-Based Operation Planning in Orthopedic Surgery", Thesis, RWTH Aachen University, Apr. 22, 2004, 90 pages.
Portheine, English Translation with Certification: "Model-Based Operation Planning in Orthopedic Surgery", Thesis, RWTH Aachen University, Apr. 22, 2004, 170 pages.
Portheine et al., In German: "Computer-Assisted Total Knee Endoprosthetics with Planning-Specific Treatement Templates", Biomed. Tech., vol. 46, Supp. vol. 1, Jan. 2001.
Portheine et al., English Translation with Certification: "Computer-Assisted Total Knee Endoprosthetics with Planning-Specific Treatement Templates", Biomed. Tech., vol. 46, Supp. vol. 1, Jan. 2001.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher et al., "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and A spects of Clinical Applications." In Nolte LP, Ganz, R. (eds). CAOS —Computer Assisted Orthopaedic Surgery. Bern, Hans Huber (In Press) 1998.
Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al., "Computer Assisted Matching of Planning and Execution in Orthopedic Surgery", IEEE, EMBS, San Diego, 1993, pp. 946-947.
Radermacher, "Computer Assisted Matching of Planning and Execution in Orthopedic Surgery", Slide Presentation, San Diego, Nov. 29, 1993, 22 pages.
Radermacher et al., "Computer Integrated Advanced Orthopedics (CIAO)", $2^{nd}$ European Conference on Eng. and Med., presented Apr. 26, 1993, 12 pages.
Radermacher et al., "Surgical Therapy Technology", Helmholtz-Institut Aachen Research Report, 1993-1994, pp. 189-219.
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Radermacher, "Image Guided Orthopedic Surgery with Individual Templates", Helmhotz-Institute for Biomed. Eng., 2 pages, 1997.
Radermacher et al., In German: "Computer-assisted operative interventions in orthopedics—are there prospects for endoprosthetics as well?", Prac. Ortho., vol. 27, pp. 149-164, 1997.
Radermacher et al., English Translation with Certification: "Computer-assisted operative interventions in orthopedics—are there prospects for endoprosthetics as well?", Prac. Ortho., vol. 27, pp. 1-17, 1997.
Radermacher et al., "Computer Based Decision Support for the Planning of Contact Faces for Manual Registration with Individual Templates", Helmholtz-Institute for Biomed. Eng., 7 pages, 1997-98.
Radermacher, In German: "Computer-Based Decision Support in the Selection and Evaluation of Contact Surfaces for Manual Referencing", Lecture presented at Helmholtz Meeting '98 and OSS '98, 7 pages.
Radermacher, English Translation with Certification: "Computer-Based Decision Support in the Selection and Evaluation of Contact Surfaces for Manual Referencing", Lecture presented at Helmholtz Meeting '98 and OSS '98, 8 pages.
Radermacher et al., In German: "Computer-Assisted Planning and Operation in Orthopedics", Orth. Prac. $36^{th}$ year, pp. 731-737, Dec. 2000.
Radermacher et al., English Translation with Certification: "Computer-Assisted Planning and Operation in Orthopedics", Orth. Prac. $36^{th}$ year, pp. 731-737, Dec. 2000.
Radermacher, "Template Based Navigation—An Efficient Technique for Hip and Knee Surgery", CAOS First Asian Meet, India, Mar. 27-28, 2004, pp. 44-50.
Ranawat et al., "MacIntosh Hemiarthroplasty in Rheumatoid Knee," Acta Orthop Belg., 39 (1): 1-11 (1973).

(56) References Cited

OTHER PUBLICATIONS

Rau et al., "Small and Neat", Medical Tech. Int'l, pp. 65, 67 and 69, 1993-94.
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Schkommadau et al., "Clinical Application of Individual Templates for Pedicle Screw Placement in Comparison to Computer Navigation", Poster presented at CAOS, Feb. 18, 2000, 1 page.
Schkommadau et al., In German: "Clinical Experience With the Individual Template Technique", Orth. Prac., vol. 37, No. 1, pp. 19-22, 2001.
Schkommadau et al., English Translation with Certification: "Clinical Experience With the Individual Template Technique", Orth. Prac., vol. 37, No. 1, pp. 19-22, 2001.
Schorn et al., "MacIntosh Arthroplasty in Rheumatoid Arthritis," Rheumatol Rehabil. Aug. 1978:17(3):155-163.
Seel et al., "Three-Dimensional Planning and Virtual Radiographs in Revision Total Hip Arthroplasty for Instability", Clinical Orthopaedics and Related Research, No. 442, pp. 35-38, Jan. 2006.
Slone et al., "Body CT: A Practical Approach", Editor Slone, 1999 McGraw-Hill publishers, Title page and Table of Contents pgs. Only (ISBN 007058219).
Staudte et al., In German: "Computer-Assisted Operation Planning and Technique in Orthopedics", North Rhine-Westphalia Acad. for Sciences, Lecture N. 444, ISSN 0944-8799, 2000, 17 pages.
Staudte et al., English Translation with Certification: "Computer-Assisted Operation Planning and Technique in Orthopedics", North Rhine-Westphalia Acad. for Sciences, Lecture N. 444, ISSN 0944-8799, 2000, 34 pages.
Stauffer et al., "The MacIntosh Prosthesis. Prospective Clinical and Gait Evaluation," Arch. Surg. 110(6):717-720 (1975).
Stout et al., "X-Ray Structure Determination: A Practical Guide", 2nd Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Testi et al., "Border Tracing Algorithm Implementation for the Femoral Geometry Reconstruction," Comp. Meth. and Programs in Biomed., vol. 65, pp. 175-182, 2001.
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).
Tsai et al., "Accurate Surface Voxelization for Manipulating Volumetric Surfaces and Solids with Application in Simulating Musculoskeletal Surgery", Inst. of Information and Computer Engineering, pp. 234-243, 2001.
Vande Berg et al., "Assessment of Knee Cartilage in Cadavers With Dual-Detector Spiral CT Arthrography and MR Imaging", Radiology, Feb. 2002: 222(2): 430-435.
Wiese et al., "Biomaterial properties and biocompatibility in cell culture of a novel self-inflating hydrogel tissue expander", J. Biomedical Materials Research Part A, 54(2):179-188, Nov. 2000.
Wordsworth et al., "MacIntosh Arthroplasty for the Rheumatoid Knee: A 10-year Follow Up," Ann. Rheum. Dis. 44(11):738-741 (1985).
Yusof et al., "Preparation and characterization of chitin beads as a wound dressing precursor", J. Biomedical Materials Research Part A, 54(1):59-68, Oct. 2000.
Bromberg & Sunstein LLP, Amendment dated Sep. 22, 2008, pertaining to U.S. Appl. No. 09/882,363, 15 pages.
Bromberg & Sunstein LLP, Amendment dated Aug. 12, 2008, pertaining to U.S. Appl. No. 11/002,573, 25 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Amendment dated Jun. 28, 2010 pertaining to U.S. Appl. No. 11/410,515, 16 pages.
Bromberg & Sunstein LLP, Amendment dated Jun. 30, 2009, pertaining to U.S. Appl. No. 11/410,515, 18 pages.
European Patent Office, European Search Report—Application No. 09716738.1 dated Feb. 6, 2012, 10 pages.
European Patent Office, European Search Report—Application No. 12170854.9-1526, dated Oct. 9, 2012, 6 pages.
European Patent Office, European Search Report—Application No. EP 03790194, dated Jul. 13, 2006, 5 pages.
European Patent Office, Extended European Search Report—Application No. 10181149.5-1526 dated Apr. 19, 2012, 9 pages.
European Patent Office, Extended European Search Report—Application No. 10181198.2-1526 dated Apr. 19, 2012, 9 pages.
European Patent Office, Extended European Search Report—Application No. 10765271.1-2310, dated Dec. 19, 2012, 6 pages.
European Patent Office, Extended European Search Report—European Application No. 10181743.5-2310, dated Mar. 11, 2011, 6 pages.
European Patent Office, Extended European Search Report—Application No. 13164557.4-1659 dated Nov. 25, 2013, 8 pages.
European Patent Office, Extended European Search Report—Application No. 13167237.0-1659 dated Nov. 25, 2013, 8 pages.
European Patent Office, Extended European Search Report—Application No. 13167246.1-1659 dated Nov. 25, 2013, 8 pages.
European Patent Office, Extended European Search Report—Application No. 13167257.8-1659 dated Nov. 25, 2013, 8 pages.
European Patent Office, Supplementary European Search Report Application No. 04812187.5, dated Sep. 27, 2007, 3 pages.
International Searching Authority, International Preliminary Report on Patentability—International Application No. PCT/US2005/044008, dated Jun. 14, 2007, together with the Written Opinion of the International Searching Authority, 8 pages.
International Searching Authority, International Search Report—International Application No. PCT/US03/38158, dated Feb. 23, 2005, 7 pages.
International Searching Authority, International Search Report—International Application No. PCT/US04/39616, dated Mar. 28, 2005, together with the Written Opinion of the International Searching Authority, 6 pages.
International Searching Authority, International Search Report—International Application No. PCT/US10/31415, dated Jun. 29, 2010, together with the Written Opinion of the International Searching Authority, 9 pages.
International Searching Authority, International Search Report—International Application No. PCT/US2005/044008, dated Mar. 30, 2006, together with the Written Opinion of the International Searching Authority, 12 pages.
International Searching Authority, International Search Report—International Application No. PCT/US2006/045172, dated Apr. 19, 2007, 12 pages.

(56) References Cited

OTHER PUBLICATIONS

International Searching Authority, International Search Report—International Application No. PCT/US2007/061681, dated Sep. 7, 2007, together with the Written Opinion of the International Searching Authority, 12 pages.
International Searching Authority, International Search Report—International Application No. PCT/US2008/057045, dated Jul. 15, 2008, together with the Written Opinion of the International Searching Authority, 13 pages.
International Searching Authority, International Search Report—International Application No. PCT/US2008/066994, dated Feb. 19, 2009, together with the Written Opinion of the International Searching Authority, 16 pages.
International Searching Authority, International Search Report—International Application No. PCT/US2009/036189, dated Jul. 13, 2009, together with the Written Opinion of the International Searching Authority, 11 pages.
International Searching Authority, Invitation to Pay Additional Fees, and Where Applicable, Protest Fee—International Application No. PCT/US2008/066994, dated Oct. 21, 2008, 5 pages.
International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/025274 dated Oct. 25, 2012, together with the Written Opinion of the International Searching Authority, 12 pages.
International Searching Authority, International Search Report—International Application No. PCT/US2012/025277 dated Oct. 25, 2012, together with the Written Opinion of the International Searching Authority, 12 pages.
International Searching Authority, International Search Report—International Application No. PCT/US2012/025280 dated Oct. 25, 2012, together with the Written Opinion of the International Searching Authority, 11 pages.
International Searching Authority, International Search Report—International Application No. PCT/US2013/025216 dated May 30, 2013, 5 pages.
United States Patent and Trademark Office, Notice of Allowance dated Aug. 5, 2011, pertaining to U.S. Appl. No. 10/764,010, 14 pages.
United States Patent and Trademark Office, Notice of Allowance dated Dec. 16, 2010, pertaining to U.S. Appl. No. 10/764,010, 11 pages.
United States Patent and Trademark Office, Notice of Allowance dated Nov. 24, 2010, pertaining to U.S. Appl. No. 11/739,326, 8 pages.
United States Patent and Trademark Office, Office Action dated Apr. 20, 2010, pertaining to U.S. Appl. No. 11/739,326, 13 pages.
United States Patent and Trademark Office, Office Action dated Apr. 20, 2011, pertaining to U.S. Appl. No. 12/135,612, 13 pages.
United States Patent and Trademark Office, Office Action dated Aug. 2, 2010 pertaining to U.S. Appl. No. 11/769,434, 83 pages.
United States Patent and Trademark Office, Office Action dated Dec. 28, 2009, pertaining to U.S. Appl. No. 11/410,515, 43 pages.
United States Patent and Trademark Office, Office Action dated Dec. 30, 2008, pertaining to U.S. Appl. No. 11/410,515, 32 pages.
United States Patent and Trademark Office, Office Action dated Feb. 13, 2014, pertaining to U.S. Appl. No. 13/306,501, 25 pages.
United States Patent and Trademark Office, Office Action dated Feb. 28, 2011, pertaining to U.S. Appl. No. 12/048,764, 12 pages.
United States Patent and Trademark Office, Office Action dated Jan. 13, 2012 pertaining to U.S. Appl. No. 12/776,840, 10 pages.
United States Patent and Trademark Office, Office action dated Jan. 26, 2010, pertaining to U.S. Appl. No. 11/671,745, 48 pages.
United States Patent and Trademark Office, Office Action dated Jan. 26, 2012, pertaining to U.S. Appl. No. 12/139,324, 14 pages.
United States Patent and Trademark Office, Office Action dated Jan. 29, 2009, pertaining to U.S. Appl. No. 10/724,010, 9 pages.
United States Patent and Trademark Office, Office Action dated Jan. 6, 2009, pertaining to U.S. Appl. No. 09/882,363, 9 pages.
United States Patent and Trademark Office, Office Action dated Jan. 9, 2009, pertaining to U.S. Appl. No. 10/764,010 11 pages.
United States Patent and Trademark Office, Office Action dated Jun. 23, 2011 pertaining to U.S. Appl. No. 11/410,515, 13 pages.
United States Patent and Trademark Office, Office Action dated Jun. 5, 2012, pertaining to U.S. Appl. No. 12/776,984, 7 pages.
United States Patent and Trademark Office, Office Action dated May 17, 2010, pertaining to U.S. Appl. No. 10/764,010, 12 pages.
United States Patent and Trademark Office, Office Action dated May 31, 2012, pertaining to U.S. Appl. No. 12/398,753, 7 pages.
United States Patent and Trademark Office, Office Action dated May 5, 2008, pertaining to U.S. Appl. No. 10/724,010, 13 pages.
United States Patent and Trademark Office, Office Action dated May 9, 2008, pertaining to U.S. Appl. No. 11/002,573, 17 pages.
United States Patent and Trademark Office, Office Action dated Nov. 26, 2007, pertaining to U.S. Appl. No. 11/002,573, 15 pages.
United States Patent and Trademark Office, Office Action dated Oct. 20, 2010, pertaining to U.S. Appl. No. 12/135,719, 10 pages.
United States Patent and Trademark Office, Office Action dated Oct. 23, 2009, pertaining to U.S. Appl. No. 10/764,010 (US Pat. No. US 2004/0167390), 13 pages.
United States Patent and Trademark Office, Office Action dated Oct. 6, 2010 pertaining to U.S. Appl. No. 11/410,515, 20 pages.
United States Patent and Trademark Office, Office Action dated Sep. 26, 2011 pertaining to U.S. Appl. No. 12/048,764, 9 pages.
United States Patent and Trademark Office, Office Action pertaining to U.S. Appl. No. 13/405,843 dated Dec. 10, 2013, 9 pages.
Sunstein Kann Murphy & Timbers LLP, Preliminary Amendment dated Aug. 12, 2011, pertaining to U.S. Appl. No. 13/017,886, 13 pages.
Bromberg & Sunstein LLP, Preliminary Amendment dated Aug. 22, 2006, pertaining to U.S. Appl. No. 11/410,515, 10 pages.
Sunstein Kann Murphy & Timbers LLP, Preliminary Amendment dated Jul. 31, 2009 pertaining to U.S. Appl. No. 11/769,434, 44 pages.
Sunstein Kann Murphy & Timbers LLP, Preliminary Amendment dated Jul. 31, 2009, pertaining to U.S. Appl. No. 11/739,326, 19 pages.
Bromberg & Sunstein LLP, Request for Continued Examination dated Jul. 6, 2009, pertaining to U.S. Appl. No. 09/882,363, 16 pages.
Bromberg & Sunstein LLP, Request for Continued Examination and Response dated Nov. 4, 2008, pertaining to U.S. Appl. No. 10/724,010, 15 pages.
Bromberg & Sunstein LLP, Request for Continued Examination and Response dated Feb. 27, 2008, pertaining to U.S. Appl. No. 11/002,573, 19 pages.
Bromberg & Sunstein LLP, Response to Office Action dated Jan. 9, 2009, pertaining to U.S. Appl. No. 10/764,010, 25 pages.
Sunstein Kann Murphy & Timbers LLP, Response to Office Action dated Apr. 20, 2010, pertaining to U.S. Appl. No. 11/739,326, 22 pages.
Sunstein Kann Murphy & Timbers LLP, Response to Office Action dated Aug. 26, 2010, pertaining to U.S. Appl. No. 12/361,213, 22 pages.
Bromberg & Sunstein LLP, Response to Office Action dated Jan. 29, 2009, pertaining to U.S. Appl. No. 10/724,010, 16 pages.
Sunstein Kann Murphy & Timbers LLP, Response to Office Action dated May 17, 2010, pertaining to U.S. Appl. No. 10/764,010, 21 pages.
Sunstein Kann Murphy & Timbers LLP, Supplemental Amendment dated Sep. 18, 2009, pertaining to U.S. Appl. No. 09/882,363, 11 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
Lombardi, Jr. et al., "Patient-Specific Approach in Total Knee Arthroplasty," Orthopedics, vol. 31, Issue 9, 8 pages, Sep. 2008.

(56) References Cited

OTHER PUBLICATIONS

International Searching Authority, International Search Report—International Application No. PCT/US2014/030001 dated Aug. 27, 2014, together with the Written Opinion of the International Searching Authority, 10 pages.
Proskauer Rose LLP, Counsel for ConforMIS, Inc., Proskauer Rose LLP, Counsel for ConforMIS, Inc., United States District Court of Massachusetts, Civil Action No. 16-10420—Document No. 1—Plaintiff's Complaint for Patent Infringement—ConforMIS, Inc., without exhibits, 14 pages, 2016.
U.S. Appl. No. 13/305,634, filed Nov. 28, 2011.
U.S. Appl. No. 13/305,636, filed Nov. 28, 2011.
U.S. Appl. No. 13/306,501, filed Nov. 29, 2011.
U.S. Appl. No. 13/306,509, filed Nov. 29, 2011.
U.S. Appl. No. 13/294,617, filed Nov. 11, 2011.
U.S. Appl. No. 13/405,826, filed Feb. 27, 2012.
U.S. Appl. No. 13/565,840, filed Aug. 3, 2012.
U.S. Appl. No. 13/718,717, filed Dec. 18, 2012.
U.S. Appl. No. 13/754,133, filed Jan. 30, 2013.
U.S. Appl. No. 13/835,863, filed Mar. 15, 2013.
U.S. Appl. No. 14/390,835, filed Oct. 6, 2014.
U.S. Appl. No. 13/865,958, filed Apr. 18, 2013.
U.S. Appl. No. 13/872,017, filed Apr. 26, 2013.
U.S. Appl. No. 13/892,547, filed May 13, 2013.
U.S. Appl. No. 13/935,446, filed Jul. 3, 2013.
U.S. Appl. No. 13/954,090, filed Jul. 30, 2013.
U.S. Appl. No. 14/021,595, filed Sep. 9, 2013.
U.S. Appl. No. 14/040,890, filed Sep. 30, 2013.
U.S. Appl. No. 14/148,067, filed Jan. 6, 2014.
U.S. Appl. No. 14/775,190, filed Mar. 15, 2014.
U.S. Appl. No. 14/308,070, filed Jun. 18, 2014.
U.S. Appl. No. 14/615,906, filed Feb. 6, 2015.
U.S. Appl. No. 14/791,672, filed Jul. 6, 2015.
Delp et al., "Computer Assisted Knee Replacement", Clinical Orthopaedics, pp. 49-56, Sep. 1998.
Proskauer Rose LLP et al., Counsel for ConforMIS, Inc., United States District Court of Massachusetts, Civil Action No. 13-12312—Document No. 1—Plaintiff's Complaint for Patent Infringement—ConforMIS, Inc., 406 pages, 2013.
Duane Morris LLP et al., Counsel for Wright Medical Technology, Inc. et al., United States District Court of Massachusetts, Civil Action No. 13-12312—Document No. 18—Defendant's Answer, Affirmative Defenses and Counterclaims to Plaintiff's Complaint—Wright Medical Technology, Inc. et al., 17 pages, 2013.
Duane Morris LLP et al., Counsel for Wright Medical Technology, Inc. et al., United States District Court of Massachusetts, Civil Action No. 13-12312—Document No. 55—Defendants' Preliminary Invalidity and Non-Infringement Disclosures—Wright Medical Technology, Inc. et al. 22 pages, 2014.
International Searching Authority, International Search Report—International Application No. PCT/US2015/012203, dated May 4, 2015, together with the Written Opinion of the International Searching Authority, 12 pages.
U.S. Appl. No. 10/681,750, filed Oct. 7, 2003.
U.S. Appl. No. 14/072,751, filed Nov. 5, 2013.
U.S. Appl. No. 14/148,511, filed Jan. 6, 2014.
Arima, MD et al., "Femoral Rotational Alignment, Based on the Anteroposterior Axis, in Total Knee Arthroplasty in a Valgus Knee," The Journal of Bone and Joint Surgery, Incorporated, vol. 77-A, No. 9, pp. 1331-1334, Sep. 1995.
Chao, PhD et al., "Computer-Aided Preoperative Planning in Knee Osteotomy," The Iowa Orthopaedic Journal, vol. 15, pp. 4-18, 1995.
Hofmann, MD et al., "Effect of the Tibial Cut on Subsidence Following Total Knee Arthroplasty," Clinical Orthopaedics and Related Research, No. 269, pp. 63-69, Aug. 1991.
Menkes, MD et al., "Are osteophytes good or bad?," Osteoarthritis and Cartilage, OsteoArthritis Research Society International, vol. 12, pp. S53-S54, 2004.
Moseley, MD et al., "A Controlled Trial of Arthroscopic Surgery for Osteoarthritis of the Knee," The New England Journal of Medicine, vol. 347, No. 2, pp. 81-88, Jul. 11, 2002.
Perry et al., "Spontaneous recovery of the joint space in degenerative hip disease," Annals of the Rheumatic Diseases, vol. 31, pp. 440-448, May 2, 1972.
Pottenger et al., "The Effect of Marginal Osteophytes on Reduction of Varus-Valgus Instability in Osteoarthritic Knees," Arthritis and Rheumatism, vol. 33, No. 6, pp. 853-858, Jun. 1990.
Whiteside, MD et al., "The Effect of Posterior Tibial Slope on Knee Stability After Ortholoc Total Knee Arthroplasty," The Journal of Arthroplasty, pp. S51-S57, Oct. 1988 Supplement.
Yau et al., "Residual Posterior Femoral Condyle Osteophyte Affects the Flexion Range after Total Knee Replacement." International Orthopaedics (SICOT), vol. 29, pp. 375-379, May 12, 2005.
Knobbe, Martens, Olson & Bear LLP, Counsel for Smith & Nephew, Inc., United States District Court of Massachusetts, Civil Action No. 1:16-cv-10420-IT—Document No. 59—Smith & Nephew, Inc.'s Preliminary Invalidity Disclosures, without exhibits, 36 pages, Sep. 16, 2016.
Knobbe, Martens, Olson & Bear, LLP Counsel for Smith & Nephew, Inc., United States Patent and Trademark Office, Before the Patent Trial and Appeal Board—Case No. IPR2016-01874, Petition for Inter Partes Review of U.S. Pat. No. 9,055,953, 102 pages, Sep. 21, 2016.
Jay D. Mabrey, M.D., Exhibit No. 1002 to Petition for Inter Partes Review of U.S. Pat. No. 9,055,953—Declaration of Jay D. Mabrey, M.D., 132 pages, Sep. 16, 2016.
Maintz et al., Exhibit No. 1015 to Petition for Inter Partes Review of U.S. Pat. No. 9,055,953—"A Survey of Medical Image Registration," Med. Car. Image Analysis, vol. 2, No. 1, pp. 1-37, Oct. 16, 1997.
Exhibit No. 1017 to Petition for Inter Partes Review of U.S. Pat. No. 9,055,953—Excerpts of Patent Prosecution History pertaining to U.S. Appl. No. 12/777,809, 578 pages.
Jay D. Mabrey, M.D., Exhibit No. 1019 to Petition for Inter Partes Review of U.S. Pat. No. 9,055,953—Curriculum Vitae of Jay D. Mabrey, M.D., 27 pages, Aug. 2, 2016.
Exhibit No. 1021 to Petition for Inter Partes Review of U.S. Pat. No. 9,055,953—U.S. Appl. No. 60/293,488, filed May 25, 2001, 15 pages.
Exhibit No. 1022 to Petition for Inter Partes Review of U.S. Pat. No. 9,055,953—U.S. Appl. No. 60/363,527, filed Mar. 12, 2002, 13 pages.
Exhibit No. 1024 to Petition for Inter Partes Review of U.S. Pat. No. 9,055,953—Excerpts from ConforMIS, Inc.'s Preliminary Invalidity NonInfringement Disclosures, Civil Action No. 1:16-cv-10420-IT—Document No. 60, 101 pages, Sep. 16, 2016.
U.S. Appl. No. 13/010,312, filed Jan. 20, 2011.
U.S. Appl. No. 13/013,195, filed Jan. 25, 2011.
U.S. Appl. No. 13/013,265, filed Jan. 25, 2011.
U.S. Appl. No. 13/013,288, filed Jan. 25, 2011.
U.S. Appl. No. 13/013,354, filed Jan. 25, 2011.
U.S. Appl. No. 13/013,383, filed Jan. 25, 2011.
U.S. Appl. No. 13/013,418, filed Jan. 25, 2011.
U.S. Appl. No. 13/013,435, filed Jan. 25, 2011.
U.S. Appl. No. 13/013,446, filed Jan. 25, 2011.
U.S. Appl. No. 13/013,461, filed Jan. 25, 2011.
U.S. Appl. No. 13/014,448, filed Jan. 26, 2011.
U.S. Appl. No. 13/014,457, filed Jan. 26, 2011.
U.S. Appl. No. 13/014,466, filed Jan. 26, 2011.
U.S. Appl. No. 13/014,474, filed Jan. 26, 2011.
U.S. Appl. No. 13/163,121, filed Jun. 17, 2011.

* cited by examiner

DEVICES, TECHNIQUES AND METHODS FOR ASSESSING JOINT SPACING, BALANCING SOFT TISSUES AND OBTAINING DESIRED KINEMATICS FOR JOINT IMPLANT COMPONENTS

RELATED APPLICATIONS

This application claims the benefit of U.S. Ser. No. 61/657,993 to Bojarski et al., entitled "Devices, Techniques And Methods For Assessing Joint Spacing, Balancing Soft Tissues And Obtaining Desired Kinematics For Joint Implant Components," filed Jun. 11, 2012, the disclosure of which is incorporated herein by reference in its entirety.

TECHNICAL FIELD

The disclosure relates generally to improved surgical tools, methods and surgical procedures that assist with the repair and/or replacement of anatomical structures such as joints and joint implant components. More specifically, various systems, tools and methods described herein facilitate the selection and/or implantation of prosthetic joint components, and assist a surgeon or medical practitioner with the proper balancing and restoration of natural and/or desired joint kinematics during a joint replacement procedure.

BACKGROUND

The natural anatomical joint structures of an individual may undergo degenerative changes due to a variety of reasons, including injury, osteoarthritis, rheumatoid arthritis, or post-traumatic arthritis. When such damage or degenerative changes become far advanced and/or irreversible, it may ultimately become necessary to replace all or a portion of the native joint structures with prosthetic joint components. Joint replacement is a well-tolerated surgical procedure that can help relieve pain and restore function in injured and/or severely diseased joints, and a wide variety of prosthetic joints are well known in the art, with different types and shapes of joint replacement components commercially available to treat a wide variety of joint conditions.

Historically, joint implant components were provided in a limited number of sizes and/or shapes, typically allowing for a one-size-fits-all or few-sizes-fit-all approach (i.e., multi-component and/or modular systems). More recently, the surgical community has come to embrace the concept of "patient-specific" and/or "patient-adapted" joint implant components (and associated surgical tools and procedural steps), in which one or more joint implant components is particularized in various manners for an individual patient. These newer techniques and implants typically utilize pre-operative anatomical image data of the patient (as well as computerized modeling and/or manipulation of such data, etc.), which is utilized to select and/or design appropriate features of an implant component that accommodate relevant features of the patient's actual anatomy. Such systems can include the selection of pre-manufactured implants or "blanks" to be modified in some manner (to accommodate various anatomical needs and/or limitations of the patient) as well as allowing for the design and manufacture of a unique implant that matches some or all of the patient's individual anatomy.

Regardless of the type of implant components utilized, there comes a point during every joint replacement/resurfacing procedure where the surgeon will desirably test or "balance" the joint, typically evaluating the tension and/or laxity of surrounding soft tissues and/or ligaments, as well as checking for proper motion and/or operation of the joint with the implant components (or possibly "trial components") implanted into the patient. Proper balancing of soft tissue and ligament tension/laxity is important during such procedures as a surgical repair resulting in excessive laxity can lead to an unstable joint, while excessive soft tissue and ligament tension can limit functionality of the joint replacement as well as lead to significant patient pain. Moreover, a joint replacement having poor kinematics can similarly significantly impact joint function and cause patient pain, as well as affect implant long term durability and/or performance.

In many surgical procedures, a portion of the procedure for balancing a joint (and associated implant components) is accomplished by introducing a series of inserts or spacers into an articulating surface (or other location) between bones and/or implant components of a joint, with each spacer having a differing thickness and/or shape to distract the relevant adjacent structures. Once an individual spacer is introduced, the surgeon can then assess the tension and/or laxity of the relevant soft tissue structures, and decide whether the current spacer creates a desired spacing of the joint, or whether a different size/shape of spacer is desirous. The surgeon can remove and replace the spacer as desired (choosing differing thicknesses and/or shapes), until a desired spacing and/or alignment of the various bones, implants, trials and/or other joint structures/components has been obtained. The surgeon can then desirably utilize information regarding the size and/or shape of the relevant chosen spacer(s) to verify and/or modify desired joint function in a variety of known manners. For joints having multiple articulations, multiple spacers for each articulation can be employed. In at least one example, the use of such spacers during a surgical procedure can guide the surgeon in choosing a desirable thickness of a polyethylene insert for insertion into a tibial tray of a knee implant component.

Implant balancing techniques are generally required during the implantation of a one-size-fits-all or few-sizes-fit-all approach, but even where a custom device, tools and/or the surgical procedure have been created or selected using patient-specific image data for an individual patient, it is often still desirable to conduct a balancing and assessment procedure on the relevant joint structures during the patient-specific and/or patient-adapted implantation procedure. Because access to the relevant joint structures typically involves cutting and/or distraction of various soft tissues surrounding the joint, as well as preparation of various anatomical support structures, the forces and relationships between the various tissue structures can be significantly altered by such surgical acts during the surgical procedure, which can have significant consequences on the kinematics of the knee that were unanticipated prior to the actual procedure. Moreover, because the joint is typically in a significantly damaged or diseased condition (thus necessitating the surgical intervention), and soft tissues including cartilage and/or ligaments can be difficult to visualize and/or differentiate, it may not be possible to precisely determine the kinematics and/or balancing of the knee solely from image data obtained prior to implantation of the implant components and/or trials. In addition, the use of balancing and measuring techniques can inform the surgeon of unanticipated complications (i.e., an incorrect surgical cut has been performed and/or an implant size and/or shape is incorrect), which can allow the surgeon an opportunity to modify the surgical procedure in some manner in an attempt to produce acceptable results.

Currently, measurement and/or assessment systems do not readily and conveniently facilitate a surgeon's balancing of the joint and/or joint implant components during the surgical procedure. Current inserts, spacers and/or other measurement tools utilized during joint balancing procedures typically involve a significant number of individual tools of differing sizes and/or shapes, with each spacer constituting a separate surgical instrument. Aside from occupying a significant amount of "real estate" in the sterile field, the use of multiple measuring tools of this type generally require multiple tool exchanges between the surgeon and back-table personnel, which can increase the opportunity for dropped tools, loss of sterility and/or interfere with the surgeon's concentration during the procedure. These difficulties can be further exacerbated as the surgeon attempts to manipulate the joint and/or release various soft tissue attachment points, as the surgeon will subsequently desire to measure and/or verify the changed balance of the joint, again mandating additional tool exchanges. In many cases, the multiple options presented by such tools and tool exchanges can be confusing for many surgeons, especially in situations where obvious visual landmarks may no longer be present (such as during revision procedures), making alignment and restoration of the joint line even more difficult.

DETAILED DESCRIPTION

Figure 1:
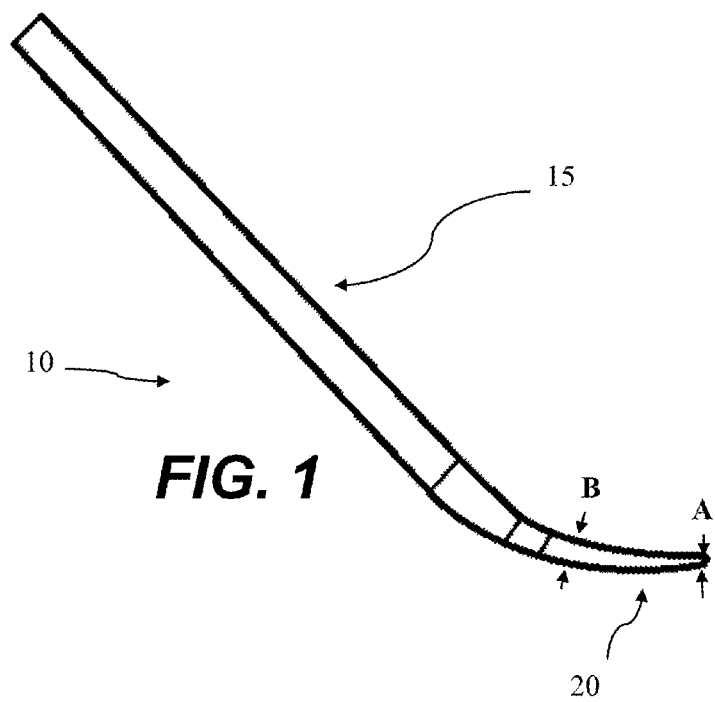
FIG. 1 depicts a side view of one embodiment of an assessment probe or measuring tool or wedge for balancing, alignment and optimization of joint kinematics during a joint replacement procedure.

The following description of various preferred embodiments are merely exemplary in nature and are in no way intended to limit the disclosure, its various applications and/or uses. Although various embodiments are discussed specifically for performing a surgical procedure on a knee joint of the human anatomy, it will be understood that the systems, devices, procedures and instruments described herein may be augmented and used for various other procedures or in other anatomies, including joints such as the hip, ankle, foot, toe, shoulder, elbow, ankle, wrist, hand, and a spine or spinal joints. Therefore, although the following description is related to probes and tools used in a knee replacement procedure, it will be understood that the teachings herein are not so limited, and various alternative embodiments and/or aspects of the present disclosure may be used and/or applied to a variety of other joints. These and other objects, advantages, and features of this disclosure will be apparent from the following description of the preferred embodiments, considered along with the accompanying drawings.

Various embodiments disclosed herein are based on the identification of a need for devices, procedures and methods that better facilitate a surgeon's balancing, alignment and optimization of joint kinematics during a joint replacement procedure. Various embodiments described herein include systems and processes to assist in the evaluation of joint structures, including the appropriate placement of joint arthroplasty components and in the evaluation of those placements. Systems and methods for facilitating and performing soft tissue balancing in joint arthroplasty are also described.

Various embodiments include tools having patient-specific and/or patient-adapted features and/or information derived from patient image data that are relevant in the determination of proper alignment of joint structures, implant components and/or inserts during joint replacement/resurfacing procedures. Moreover, various embodiments include a reduced number of surgical tools and/or surgical tool exchanges while enabling a surgeon to determine a desired alignment, spacing and/or laxity of a joint structure during joint replacement/resurfacing procedures.

Various embodiments include improved measurement and alignment tools, assessment probes or "spacers" for use in joint replacement and/or resurfacing procedures, including procedures that utilize one-size-fits-all, many-sizes-fits all (modular), patient-specific, patient-adapted and/or patient engineered joint implant components. In various embodiments, a single assessment probe, measuring tool or small group of tools can be utilized by a surgeon to measure, balance and/or otherwise optimize the spacing and/or kinematics of a joint replacement/resurfacing implant while requiring fewer individual tools and/or tool exchanges than required using existing surgical measuring tool sets. These arrangements significantly reduce the complexity of the surgical procedure, reduce the amount of "real estate" required for tools in the sterile field, greatly increase the speed at which a given alignment and/or measurement can be performed, and significantly reduce the opportunity for dropping of tools, loss of sterility, confusion and/or damage to a given tool or tool set during tool exchanges with back-table personnel.

In various embodiments, assessment probes, spacers or other measuring tools are described that include a plurality of individual measuring structures of differing sizes and/or shapes on a single tool, each of which can be utilized individually to determine a desired spacing and/or alignment of anatomical and/or implant structures (or combinations thereof). Because a single tool can include a plurality of measuring surfaces, the surgeon need not remove the measuring tool from the surgical field adjacent the patient to exchange it for a differently sized/shaped tool, but can merely manipulate (i.e., rotate or "flip") the tool to employ a different measuring surface with the same anatomical structure.

In various additional embodiments, the individual measuring surfaces of a single assessment probe or measuring tool can include a measuring surface of varying thickness and/or shape, which desirably allows a single individual measuring surface to be employed to determine a plurality of measurements, as well as to determine fractional or partial measurements that may be significantly more accurate than those obtained using standard measuring tools or spacers. Not only can such arrangements further reduce the number of measuring tools required for an individual surgical procedure, but such tools can allow a surgeon to better approximate and/or estimate the desired spacing and/or balancing of the joint implant components, especially where a desired measurement may fall "between" or intermediate spacing or alignment values that can be obtained in the joint using various combinations of modular components.

The embodiments described herein can include features that correspond to patient-adapted articular implant components that are tailored to address the needs of individual, single patients. Such features can include dimensions, shapes or other characteristics that are particularized to an individual implant component and/or set of components, as well as features that are particularized to an individual patient's anatomy.

The advantages include, for example, better fit, more natural movement of the joint, faster procedures, less opportunity for error, reduction in the amount of bone removed during surgery and less invasive procedures. Such patient-adapted articular implants and associated measurement tools can be created from images of the patient's joint. Based on the images, patient-adapted implant components and associated assessment probes or measuring tools can be selected and/or designed to include features (e.g., surface contours, curvatures, widths, lengths, thicknesses, and other features) that match or otherwise accommodate existing features in the single, individual patient's joint as well as features that approximate an ideal and/or healthy feature that may not exist in the patient prior to a procedure. Moreover, by altering the design approach to address several implant design issues, several non-traditional design and/or implantation approaches have been identified that offer improvements over traditional implant designs and traditional surgical procedures.

Patient-adapted features of surgical tools can include patient-specific and/or patient-engineered. Patient-specific (or patient-matched) implant component and/or assessment probe/measuring tool features can include features adapted to match one or more of the patient's biological features, for example, one or more biological/anatomical structures, alignments, kinematics, and/or soft tissue features. Patient-engineered (or patient-derived) features of an implant component can be designed and/or manufactured (e.g., preoperatively designed and manufactured) based on patient-specific data to substantially enhance or improve one or more of the patient's anatomical and/or biological features.

The patient-adapted (e.g., patient-specific and/or patient-engineered) implant components and measuring tools described herein can be selected (e.g., from a library), designed (e.g., preoperatively designed including, optionally, manufacturing the components or tools), and/or selected and designed (e.g., by selecting a blank component or tool having certain blank features and then altering the blank features to be patient-adapted). Moreover, related methods, such as designs and strategies for resectioning a patient's biological structures also can be selected and/or designed. For example, an implant component bone-facing surface and a resectioning strategy for the corresponding bone-facing surface can be selected and/or designed together so that an implant component's bone-facing surface(s) match or otherwise conform to or accommodate the resected surface(s). In addition, one or more assessment probes or measuring tools optionally can be selected and/or designed to facilitate the resection cuts that are predetermined in accordance with resectioning strategy and implant component selection and/or design.

In certain embodiments, patient-adapted features of an implant component, measuring tools and/or related methods can be achieved by analyzing imaging test data and selecting and/or designing (e.g., preoperatively selecting from a library and/or designing) an implant component, a measuring tool, and/or a procedure having a feature that is matched and/or optimized for the particular patient's biology. The imaging test data can include data from the patient's joint, for example, data generated from an image of the joint such as x-ray imaging, cone beam CT, digital tomosynthesis, and ultrasound, a MRI or CT scan or a PET or SPECT scan, which can be processed to generate a varied or corrected version of the joint or of portions of the joint or of surfaces within the joint. Certain embodiments provide methods and/or devices to create a desired model of a joint or of portions or surfaces of a joint based, at least partially, on data derived from the existing joint. For example, the data can also be used to create a model that can be used to analyze the patient's joint and to devise and evaluate a course of corrective action. The data and/or model also can be used to design an implant component and/or measuring tool having one or more patient-specific features, such as a surface or curvature.

In various embodiments, one or more assessment probes and/or measuring tools can be designed and/or selected using patient-specific image data, with a variety of shapes and/or sizes of the measuring features on each tool particularized for an anticipated range or variety of measurements. Similarly, the assessment probes or measuring tools described herein can be designed and/or selected to reflect features of various associated implant components, with various measurements or other features corresponding to features of available modular implant component combinations (or different spacing and/or sizing available using various combinations of components).

In one aspect, embodiments described herein include assessment probes or measuring tools having at least one wedge-shaped measuring portion, each portion having an upper surface and a bottom surface, with a varying relative thickness therebetween. This relative thickness is desirably tapered or otherwise varies, including being increased at a location proximal to a handle or connection end of the measuring portion, and reduced at a location distal to the handle or connection end (or other arrangements, as desired). At least one of the upper and lower surfaces can include a plurality of indicia that identifies at least two thicknesses between the upper and lower surfaces of the tool, the two thicknesses being different thicknesses and positioned at different locations along the measuring portion. In use, the measuring portion can be inserted between a first and second structure, said structures being any combination of native and/or modified anatomical structures and/or implant components and/or associated surgical tools. The measuring portion can be advanced between the first and second structures, progressively distracting the structures until a desired distraction is achieved. Once the tool is in a desired location, the indicia on the upper and/or lower surfaces can be utilized to visually identify the amount of distraction occurring between the first and second structures. This distraction measurement can be used in a variety of ways to assist with planning, preparation, execution, implantation and/or modification of the joint implant components, as described in various disclosures herein as well as using techniques known in the art.

In various embodiments, assessment probes or measuring tools can include one or more surface(s): (1) designed to negatively-match and/or conform to one or more native bone and/or articular surfaces, (2) designed to negatively-match and/or conform to one or more modified surfaces that were modified to allow access to the joint or to remove/alter tissues that cannot be accurately imaged (i.e., articular cartilage), (3) designed to negatively-match and/or conform to one or more cut or prepared surfaces that were modified, for example based on pre-determined geometries or based on patient-specific geometries, and/or (4) designed to negatively-match and/or conform to one or more surface features of one or more implant components. In certain embodiments, a first surface portion can include at least a portion that substantially negatively-matches a feature of the patient's anatomy and an opposing second surface portion can include at least a portion that substantially negatively matches an opposing joint-facing surface of an implant component.

In various embodiments, surfaces of assessment probes or measuring tools may be designed and/or selected to accommodate one or more patient-specific surface features. For example, where the probe/tool desirably assess or measures a joint laxity between native anatomical surfaces, such as prior to the preparation of anatomical support structures for implant components, the corresponding upper and lower surfaces of the measuring portion may have portions designed to accommodate or compensate for the native anatomical structures. Various features of the measuring portion surfaces maybe designed to facilitate assessment and/or measurement of the joint in static and/or dynamic modes, which may include concavities, depressions and/or other features on one or both of the measuring portion surfaces. In one exemplary embodiment, a tool for measuring the laxity between a native femoral condyle and a native tibial condyle can include an upper surface having a curved surface with a greater radius of curvature than a corresponding radius of curvature of the native condyle, which desirably facilitates insertion of the tool between the femur and tibia and maintenance of a desired position during flexion/extension (or other positions) of the joint (by the surgeon) while allowing the surgeon to directly visualize thickness indicia on the upper surface of the measuring portion.

Various features of the embodiments disclosed herein can be patient-specific or patient engineered for each surgical patient, with one or more of each probe/tool including features that are tailored to an individual patient's joint morphology and/or various implant components intended for the patient. In at least one preferred embodiment, the system may be designed as a first assembly for measuring or evaluating opposing native anatomical structures prior to preparation of various anatomical support surfaces, a second assembly for measuring or evaluating opposing anatomical structures including a prepared anatomical surface (with or without an implant component or trial attached thereto) and an opposing unmodified native anatomical surface, and a third assembly for measuring and/or evaluating opposing implant components (or trials) in preparation for selection and insertion of an articulating insert or permanent spacer component (i.e., such as a polyethylene insert for a tibial tray implant). In various alternative embodiments, instruments designed and/or selected/modified may include surfaces and/or features that facilitate implantation of implant components in specific anatomical regions, including a knee, hip, ankle, foot, toe, shoulder, elbow, wrist, hand, and a spine or spinal joints.

In various joints, one or more implant components can include a metallic portion and a non-metallic portion (as well as various other combinations of metal, ceramics and/or polymers for the multiple portions), such as a metal backing plate or "tray" and a polyethylene ("poly") insert attaching thereto. The backing plate may be secured directly to a prepared anatomical surface, and the poly insert attached to the joint-facing inner portion of the plate, in a manner similar to a tibial tray and polyethylene insert(s) for a knee arthroplasty implant. In various embodiments, multiple poly inserts of varying thicknesses, shapes, curvatures and/or sizes, including differing central and/or rim geometries, orientations and/or surface configurations, can be included and accommodated by a single metallic tray, thereby allowing the physician to modify the ultimate performance of the implant (or portions thereof) during the surgical procedure.

Many surgical procedures require a wide array of instrumentation and other surgical items. Such items may include, but are not limited to: sleeves to serve as entry tools, working channels, drill guides and tissue protectors; scalpels; entry awls; guide pins; reamers; reducers; distractors; guide rods; endoscopes; arthroscopes; saws; drills; screwdrivers; awls; taps; osteotomes, wrenches, trial implants and cutting guides. In many surgical procedures, including orthopedic procedures, it may be desirable to employ patient-specific and/or patient-adapted image data and computerized modeling to optimize the design and/or selection/modification of one or more features of various instruments and implants to facilitate their use in surgical procedures. In some embodiments, an exemplary surgical instrument can be an assessment probe or measuring tool having one or more features designed and/or selected using patient-specific and/or patient-adapted image information and/or computerized models.

In at least one alternative embodiment, the various surgical tools and/or implant components described herein can include a computer-aided surgical navigation system with sensing capabilities (such as, for example, fiducial markers attached to instruments and/or anatomical locations) in a surgery on a joint, including a total joint arthroplasty. Systems and processes according to some embodiments could track various body parts such as bones, to which navigational sensors may be implanted, attached or associated physically, virtually or otherwise. Such systems and processes could employ position and/or orientation tracking sensors such as infrared sensors acting stereoscopically or other sensors acting in conjunction with navigational references to track positions of body parts, surgery-related items such as implements, instrumentation, trial prosthetics, prosthetic components, and virtual constructs or references such as rotational axes which have been calculated and stored based on designation of bone landmarks. Sensors, such as cameras, detectors, and other similar devices, could be mounted overhead with respect to body parts and surgery-related items to receive, sense, or otherwise detect positions and/or orientations of the body parts and surgery-related items. Processing capability such as any desired form of computer functionality, whether standalone, networked, or otherwise, could take into account the position and orientation information as to various items in the position sensing field (which may correspond generally or specifically to all or portions or more than all of the surgical field) based on sensed position and orientation of their associated navigational references, or based on stored position and/or orientation information. The processing functionality could correlate this position and orientation information for each object with stored information, such as a computerized fluoroscopic imaged file, a wire frame data file for rendering a representation of an instrument component, trial prosthesis or actual prosthesis, or a computer generated file relating to a reference, mechanical, rotational or other axis or other virtual construct or reference. Such information could be used to design and/or select/modify implant components and/or tools, as well as display position and orientation of these objects on a rendering functionality, such as a screen, monitor, or otherwise, in combination with image information or navigational information such as a reference, mechanical, rotational or other axis or other virtual construct or reference.

Figure 2:
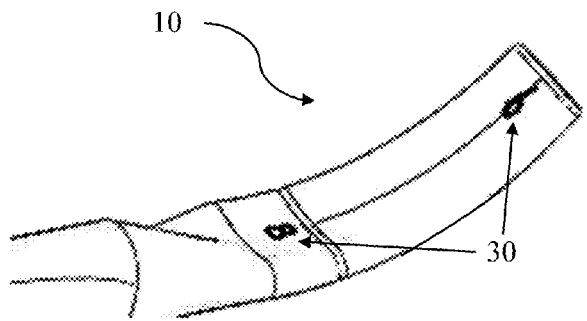
FIG. 2 depicts a partial perspective view of a measuring element of the probe/tool of FIG. 1.

FIGS. 1 and 2 depict side plan and partial perspective views, respectively, of one embodiment of an assessment probe or measuring tool or "spacer" 10 for measuring and/or evaluating a desired distraction between opposing anatomical structures (including native anatomy, prepared anatomy, implant components, surgical tools and/or any combinations thereof) of a patient. In various embodiments, this tool can comprise a curved (or flattened or other shaped) stem 20 having opposing first and second surfaces, and a progressively varying thickness (from a first thickness A to a second thickness B, as shown on FIG. 1). The stem may also have varying thickness along the medial to lateral axis to correct and/or distract for valgus deformities. Desirably, the stem 20 is attached or otherwise secured to a handle 15 or other connection feature, with the thickness of the stem progressively decreasing further away from the handle 15. As can be best seen on FIG. 2, a plurality of indicia or measurement marks 30 (or other indicators) on one or more of the surfaces are provided that desirably correspond to a localized thickness of the stem proximate the marks.

In use, the probe/tool 10 can be pushed into the joint, between opposing surfaces, and advanced (and progressively distract the relevant contact surfaces further apart) until a desired distraction between the surfaces occurs (potentially indicating a desired tension of surrounding tissues and/or other separation between the two surfaces). The relevant measurement mark corresponding to the thickness of the tool between the opposing surfaces can then be determined visually, by imaging, or possibly by tactile "feel," if desired, and the value used in a variety of ways to verify and/or modify the surgical procedure and/or implant components.

Figure 3:
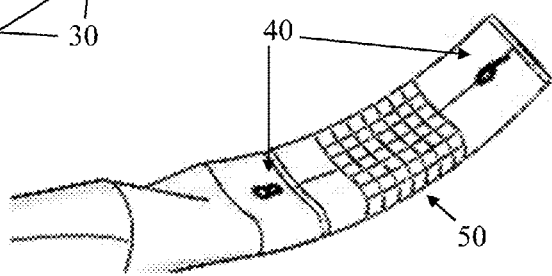
FIG. 3 depicts a partial perspective view of one alternate embodiment of a measuring element of the probe/tool of FIG. 1.

FIG. 3 depicts another embodiment of a surgical measuring tool incorporating indicia on one or more surfaces of the measuring tool. In this embodiment, the indicia include a separate or "intermediate region" 50 that extends between the numeric indicia 40. Desirably, this intermediate region can assist a surgeon with determining a more exacting value for a distraction measurement that is positioned between various numerical indicators—which could include an optimal or desired distraction zone or amount based on the pre-operative imaged and/or modeled anatomy. In this embodiment, the intermediate region can extend from a thickness of 6.75 mm (which can occur at the beginning portion of the region proximate the "6" indicator) to a thickness of 7.25 mm (the end portion of the region proximate the "8" indicator). When the measuring tool is in use, the various indicia that may be visible to the surgeon beyond the relevant anatomical or other structures can desirably be used to determine the approximate distraction between the relevant surfaces. For example, if a majority of the intermediate region is visible, the distraction will be approximately 6.75 mm, while if little or none of the intermediate region is visible, the distraction will more closely approximately 7.25 mm. The use of such intermediate indicators can expand the accurate use of the tools described herein to include various intermediate thicknesses (e.g., in increments of 0.5 mm, 0.25 mm, and/or 0.1 mm), as well as to allow the surgeon to better determine the "closeness" of the measurement to respective numerical indicia.

Figure 4:
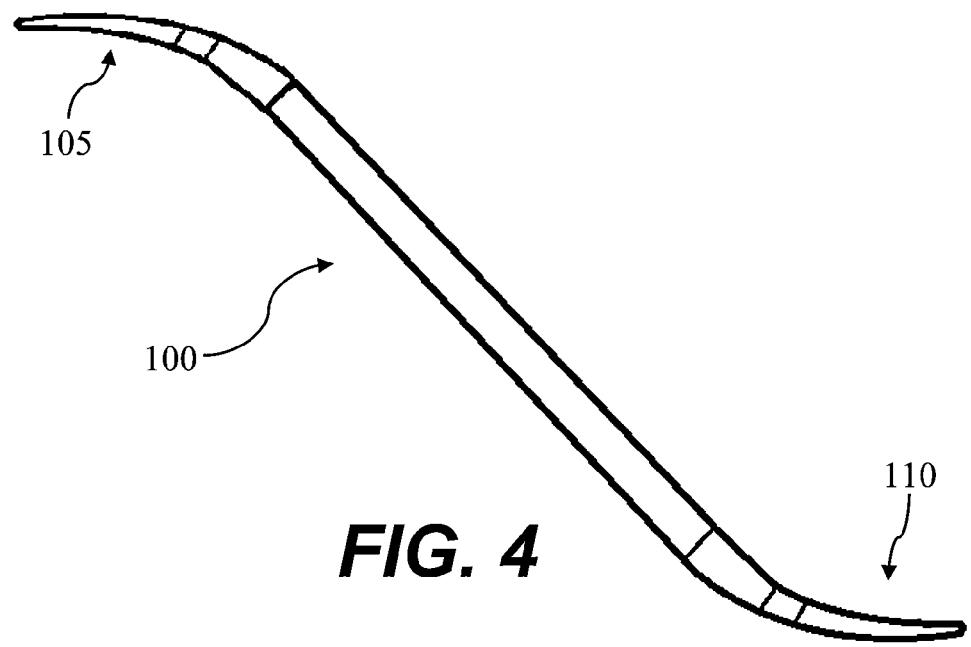
FIG. 4 depicts a side view of an alternative embodiment of an assessment probe/measuring tool or wedge for assessing, balancing, alignment and/or optimization of joint kinematics during a joint replacement procedure.

FIG. 4 depicts another embodiment of an assessment probe, measuring tool or "spacer" 100 for measuring and/or evaluating a desired distraction between opposing anatomical structures, with a pair of measuring surfaces 105 and 110 positioned on opposing ends of the tool. In this embodiment, each of the measuring surfaces 105 and 110 will desirable be useful in measuring a different range of distraction(s), which allows the surgeon to insert the tool and assess the joint and, if desired, remove, rotate and reinsert the tool to measure a different amount of distraction, if desired.

Figure 5:
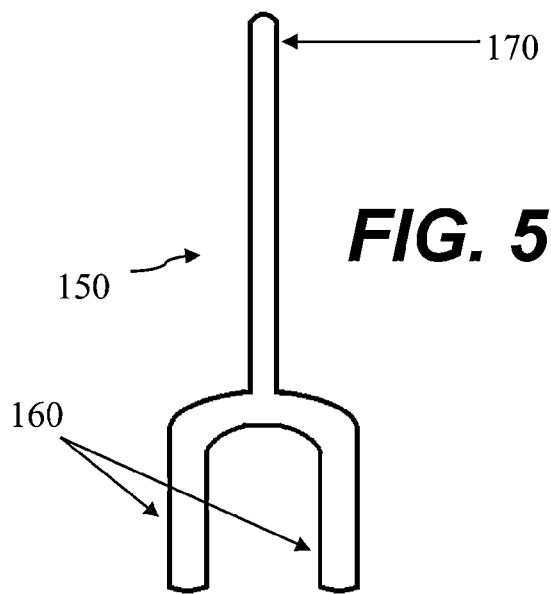
FIG. 5 depicts a side view of another alternative embodiment of an assessment probe/measuring tool or wedge for assessing, balancing, alignment and/or optimization of joint kinematics during a joint replacement procedure.

FIG. 5 depicts one alternative embodiment of an assessment probe or measuring tool 150 comprising a dual-prong or "forked" device, with individual measuring wedges 160 on each fork. In this embodiment, the individual forks could be advanced individually (by angling or rotating the tool side to side), allowing measurement using an individual fork (as previously described) or simultaneously where two articulations are being measured simultaneously (e.g., measuring and assessing the medial and lateral condyles of a femur/tibia simultaneously in a knee joint). Alternatively, the tool 150 could be particularly useful in measuring distraction of two portions of an implant (e.g., two sides of a humeral head in contact with the glenoid tray of a shoulder implant and/or two portions of a femoral head in contact with an acetabular cup in a hip implant). Where the measuring wedges are utilized simultaneously, the tool could be tilted or rotated to allow advancement or withdrawal of one side of the measuring tool while retaining the other side in a desired position. Such an arrangement may be particularly well suited for measurement of curved and/or spherical surfaces, such as the femoral or humeral head.

If desired, the embodiment of FIG. 5 could incorporate an additional measuring wedge 170 on a portion of the tool opposite the measuring wedges 160.

Figure 6:
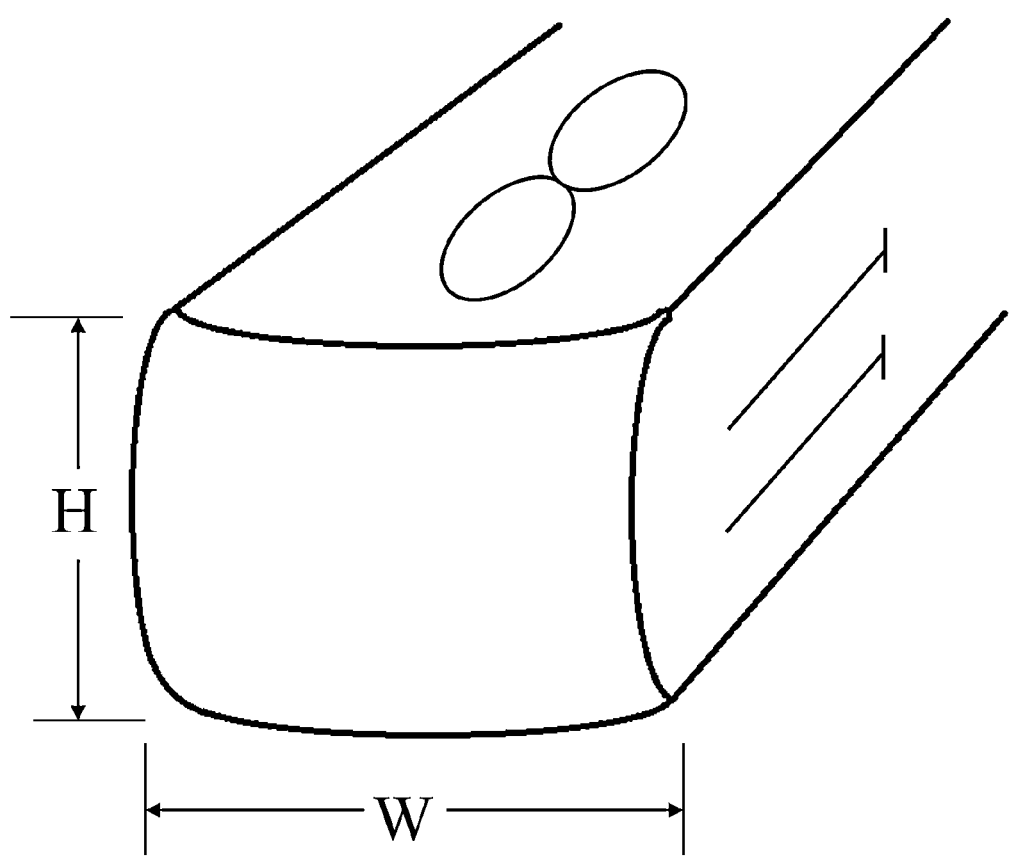
FIG. 6 depicts a partial perspective view of an alternate embodiment of a measuring element incorporating multiple measuring surfaces.

FIG. 6 depicts one alternate embodiment of the distal end of a measuring wedge, in which the wedge includes a plurality of measuring surfaces with differing thicknesses depending upon surface orientation. In this embodiment, the wedge has a first orientation "H," which can measure distractions of 8 mm or more, and a second orientation "W," which can measure distractions of 11 mm or more. In use, if a surgeon desires to employ a measuring tool of differing size, the surgeon need only withdraw the wedge from the anatomy, rotate the measuring surface 90 degrees, and reinsert the wedge to measure the differing distraction. If desired, the various wedges can include wedges of constant thickness and/or varying thickness.

Figure 7:
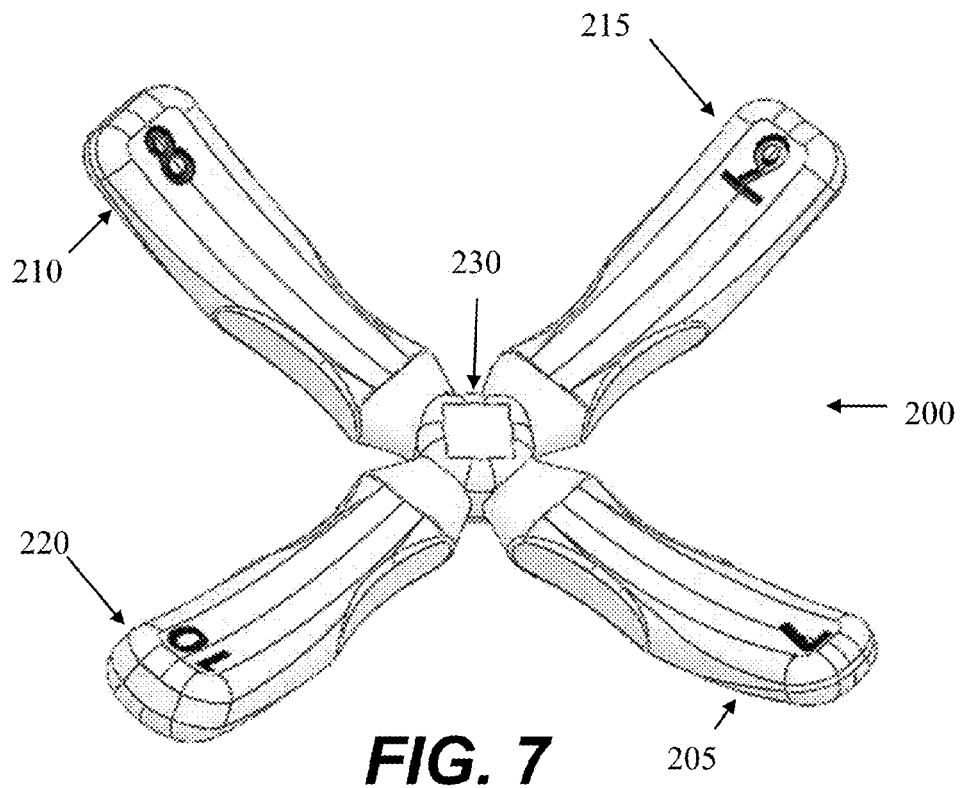
FIG. 7 depicts a perspective view of an alternative embodiment of an assessment probe/measuring tool or wedge for assessing, balancing, alignment and/or optimization of joint kinematics during a joint replacement procedure.
Figure 8:
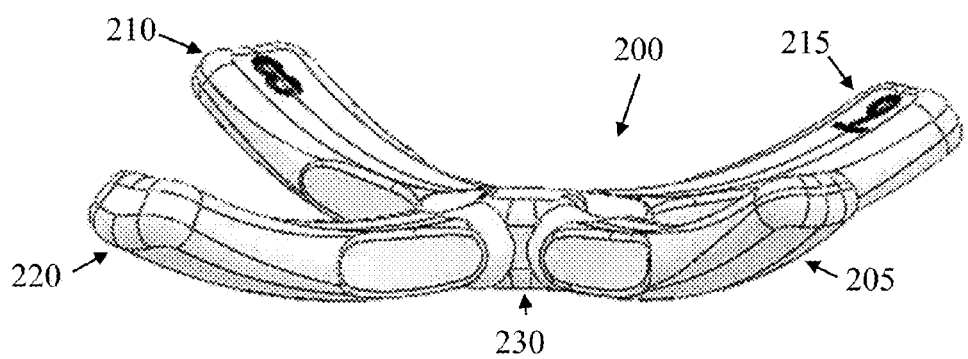
FIG. 8 depicts a side perspective view of the probe/tool of FIG. 7.

FIGS. 7 and 8 depict views of one alternative embodiment of an assessment probe or measuring tool 200 which includes a plurality of measuring surfaces or "prongs" 205, 210, 215 and 220, connected together at a common hub 230. In this embodiment, each of the prongs is of a relatively constant thickness (with each prong having a differing thickness than the other prongs), allowing a surgeon to insert a chosen prong between opposing surfaces to a desire depth, but the depth of insertion of a given prong will not significantly affect the amount of distraction between the opposing surfaces. In this embodiment, the measuring tool 200 is used in adjusting and optimizing alignment, tension, balance, and position during a knee implant surgery. The tool 200 may be one of a series of tools utilized to determine an optimal size and shape for a tibial tray insert for ultimate placement in the knee joint, or it may be the only measuring tool in the surgical kit for the entire procedure. Desirably each measuring portion 205, 210, 215 and 220 corresponds to one or more of a plurality of tibial inserts in the surgical kit, although various embodiments could include one or more "adjustable" spacers having detents or other mechanisms that facilitate adjustment and measurement of the of the joint space (with the medial and lateral sides independently adjustable, if desired). In particular, a first side of the spacer has a first height and/or alignment, and a second side of the spacer has a second height and/or alignment (allowing for medial/lateral distal femoral component bearing surface or cut asymmetry). The superior surfaces of the spacer desirably engage the cut surface of the femur and the inferior surfaces engage the cut surfaces of the tibia. In various embodiments, the various spacers can be patient-adapted to fit the particular patient, and may incorporate perimeter matching or other indicia to correspond to some or all of the perimeter of the cut and/or uncut bone surfaces (i.e., the outer perimeter of the jig matches the outer perimeter of the bone surfaces—cut and/or uncut). In certain embodiments, the spacers can include a resection surface to guide a subsequent surgical bone cut. Desirably, the thinnest insert that properly balances the knee will be chosen, reducing the chance for "overstuffing" of the knee joint.

Figure 9:
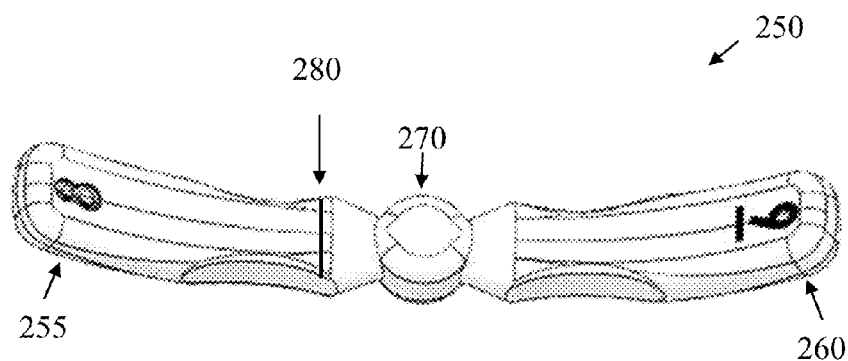
FIG. 9 depicts a perspective view of another alternative embodiment of an assessment probe/measuring tool or wedge for assessing, balancing, alignment and/or optimization of joint kinematics during a joint replacement procedure.
Figure 10:
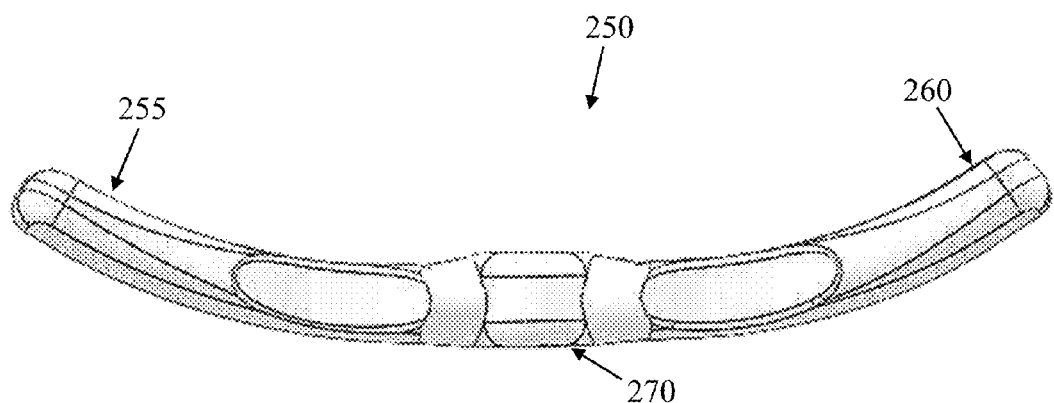
FIG. 10 depicts a side perspective view of the probe/tool of FIG. 9.

FIGS. 9 and 10 depict views of another alternative embodiment of an assessment probe or measuring tool 250 which includes a plurality of measuring surfaces or "prongs" 255 and 260, connected together at a common hub 270. In this embodiment, each of the prongs is of a relatively constant thickness (in a manner similar to the embodiment previously described), with each prong having a differing thickness than an opposing prong. This embodiment may be particularly well suited for minimally-sized incisions or other arrangements where the multi-pronged tool of FIGS. 7 and 8 may not fit within the surgical incision and/or may interfere with surrounding anatomical structures in an undesirable manner. In many cases, simply gaining access during the surgical repair of a joint can often be particularly challenging, as the joint is often completely surrounded by a joint capsule, and numerous soft and connective tissues are often positioned and/or secured on almost every side of the joint. Although many less-invasive access strategies for various joints exist, many procedures generally require relatively large incisions through soft tissue. Further, various procedures require that many muscle and muscle attachments (as well as other soft connective tissues) be cut to achieve access to selected portions of the anatomy. Although it may be selected or necessary to perform many procedures in this manner, it may also be desirable to achieve a surgical correction via a less invasive procedure. Where a complete exposure and/or substantial/complete joint dislocation is undesirable or contraindicated, such as where damage and/or the removal of such tissues can unacceptably destabilize the joint, the surgical access may be extremely limited (i.e., using less invasive and/or minimally invasive approaches), which can significantly reduce the ability of the surgeon to access and/or directly visualize various anatomical structures within the joint. Such inability to properly visualize and prepare the various anatomical structures, as well as the limited ability to visualize and/or position implant components implanted therein, can significantly reduce the effectiveness of even the most skilled surgeon and surgical repair.

In various embodiments, the measurements taken using the various tools described herein can correspond to a variety of options concerning surgical steps and/or implant components, including selecting one or more in a series of implant components and/or inserts (and/or combinations thereof).

Optimizing Soft-Tissue Tension, Ligament Tension, Balancing, Flexion and Extension Gap As part of a surgical procedure for implantation of a joint resurfacing and/or replacement implant, a surgeon will desirably have the ability to make adjustments in various implant positions and/or orientations such as rotation, bone cuts, cut height and selected component thickness, insert thickness or selected component shape or insert shape. In many cases, various types of adjustments can be made at almost any point in the surgical procedure, depending upon the surgeon's desires, training and/or experience. Such intraoperative adjustments desirably allow an optimal compromise to be found, for example, between biomechanical alignment and joint laxity or biomechanical alignment and joint function, e.g., in a knee joint flexion gap and extension gap. Moreover, even where the entirety of the surgery has been pre-planned using patient image data, and patient-specific implants, procedures and surgical tools have been custom created for an individual patient, the need and opportunity for the types of "adjustments" will often still exist. Thus, in many case, multiple approaches exist for optimizing soft-tissue tension, ligament tension, ligament balancing, and/or altering the flexion and/or extension gap(s).

In a typical joint replacement procedure, a surgeon will have pre-planned his or her surgical approach, and will have chosen an implant or group of implants that the surgeon has judged suitable and/or appropriate for the patient's surgical repair. Once the relevant joint structures have been exposed, however, it is often desirable to initially verify the condition of the joint and/or surrounding soft/connective tissues, to ensure that the chosen surgical repair is appropriate. In many cases, the tissues may perform differently than anticipated, which may impel the surgeon to modify or "adjust" his or her intended surgical procedure in some manner. In order to evaluate and/or quantify the amount and/or type of such adjustments desirable or necessary, however, surgeons will typically evaluate the joint structures in a variety of ways, including the use of distraction spacers and/or other measuring instruments to determine the true condition of the anatomical structures and associated connective tissues.

In various exemplary embodiments involving a knee joint replacement procedure, one or more of the following exemplary "adjustments" to the surgical procedure and/or implant components could be made during the surgical procedure to alter various features and/or performance of the resulting joint repair. Of course, any one option described in Table 1 could be optimized as desired, either alone or in combination with one or more other options identified in the table and/or known in the art for achieving different flexion and extension, abduction, or adduction, internal and external positions and different kinematic requirements.

TABLE 1

Exemplary approach options for optimizing soft-tissue tension, ligament tension, ligament balance, and/or flexion and extension gap(s) in a knee joint

| Option # | Description of Exemplary Option |
|---|---|
| 1 | Position of one or more femoral bone cuts |
| 2 | Orientation of one or more femoral bone cuts |
| 3 | Location of femoral component |
| 4 | Orientation of femoral component, including rotational alignment in axial, sagittal and coronal direction |
| 5 | Position of one or more tibial bone cuts |
| 6 | Orientation of one or more tibial bone cuts including sagittal slope, mediolateral orientation |
| 7 | Location of tibial component |
| 8 | Orientation of tibial component, including rotational alignment in axial, sagittal and coronal direction |
| 9 | Tibial component height |
| 10 | Medial tibial insert or component or composite height |
| 11 | Lateral tibial insert or component or composite height |
| 12 | Tibial component profile, e.g., convexity, concavity, trough, radii of curvature |
| 13 | Medial tibial insert or component or composite profile, e.g. convexity, concavity, trough, radii of curvature |
| 14 | Lateral tibial insert or component or composite profile, e.g. convexity, concavity, trough, radii of curvature |
| 15 | Select soft-tissue releases, e.g. partial or full releases of retinacula and/or ligaments, "pie-crusting" etc. |

Depending upon a surgeon's desires and experience, the surgeon can initially optimize the femoral and tibial resections in a knee joint replacement/resurfacing procedure. Optimization can be performed by measuring soft-tissue tension or ligament tension or balance for different flexion and extension angles or other joint positions before any bone has been resected, once a first bone resection on a first articular surface has been made and/or after a second bone resection on a first or second articular surface has been made, such as a femur and a tibia (knee), humerus and a glenoid (shoulder), and/or a femur and an acetabulum (hip).

The position and/or orientation between a first implant component and a second, opposing implant component or a first articular surface and a trial implant or a first trial implant and a second trial implant or an alignment guide and an instrument guide and/or any combinations thereof can be optimized with the use of, for example, interposed measuring tools such as spacers, wedges, screws and other mechanical or electrical methods known in the art. A surgeon may desire to influence joint laxity as well as joint alignment. This can be optimized for different flexion and extension, abduction, or adduction, internal and external rotation angles. For this purpose, spacers can be introduced at or between one or more steps in the implant procedure. One or more of the spacers can be attached or in contact with one or more instruments, trials or, optionally, patient-specific molds. The surgeon can intraoperatively evaluate the laxity or tightness of a joint using spacers with different thicknesses or one or more spacers with the same thickness. For example, spacers can be applied in a knee joint in the presence of one or more trials or instruments or patient-specific molds and the flexion gap can be evaluated with the knee joint in flexion. The knee joint can then be extended and the extension gap can be evaluated. Ultimately, the surgeon selects for a given joint an optimal combination of spacers and trial or instrument or patient-specific mold. A surgical cut guide can be applied to the trial or instrument or patient-specific mold with the spacers optionally interposed between the trial or instrument or patient-specific mold and the cut guide. In this manner, the exact position of the surgical cuts can be influenced and can be adjusted to achieve an optimal result. Someone skilled in the art will recognize other means for optimizing the position of the surgical cuts. For example, expandable or ratchet-like devices can be utilized that can be inserted into the joint or that can be attached or that can touch the trial or instrument or patient-specific mold. Hinge-like mechanisms are applicable. Similarly, jack-like mechanisms are useful. In principal, such instruments can be useful for fine tuning the position of a cut guide relative to a trial or instrument or patient-specific mold.

In knee replacement and/or resurfacing procedures, measuring tool and other surgical instruments can be used to optimize the implant and knee joint for different flexion and extension, abduction, or adduction, internal and external rotation angles. For this purpose, for example, measuring tool such as spacers can be introduced that are attached or that are in contact with one or more trials or instruments or patient-specific molds. Using such tools, the surgeon can intraoperatively evaluate the laxity or tightness of a joint using spacers with different thickness or one or more spacers with the same thickness. For example, spacers can be applied in a knee joint in the presence of one or more instruments or trials or molds and the flexion gap can be evaluated with the knee joint in flexion. Different thickness trials can be used. In various embodiments, the terms spacer or insert can be used interchangeably with the term trial.

In various embodiments, a surgeon may elect to insert different trials or spacers or instruments of different thicknesses in the medial and/or lateral joint space in a knee. This can be done before any bone has been resected, once a first bone resection on a first articular surface has been made and/or after a second bone resection on a first or second articular surface has been made, such as a femur and a tibia or a medial and a lateral condyle or a medial and a lateral tibia. The joint can be tested for soft-tissue tension, ligament tension, ligament balance and/or flexion or extension gap for different orientations or kinematic requirements using different medial and lateral trial or spacer thicknesses, e.g., at different flexion and extension angles. Surgical bone cuts can subsequently optionally be adapted or changed. Alternatively, different medial and lateral insert thickness or profiles or composite heights can be selected for the tibial component(s). For example, combinations of medial and lateral spacers or trials having thicknesses described in Table 2 can be inserted.

TABLE 2

Exemplary medial and lateral spacer, trial, and/or insert heights that can be used in combination

| Medial spacer, trial, and/or insert height | Lateral spacer, trial, and/or insert height | Notes |
|---|---|---|
| 6 mm | 6 mm | Same medial and lateral spacer, trial, and/or insert height |
| 7 mm | 7 mm | |
| 8 mm | 8 mm | |
| 9 mm | 9 mm | |
| 10 mm | 10 mm | |
| 11 mm | 11 mm | |
| 12 mm | 12 mm | |
| 13 mm | 13 mm | |
| 14 mm | 14 mm | |
| 15 mm | 15 mm | |
| 16 mm | 16 mm | |
| 6 mm | 7 mm | Different medial and lateral spacer, trial, and/or insert (6 mm medial spacer, trial, and/or insert height with various lateral spacer, trial, and/or insert heights) |
| 6 mm | 8 mm | |
| 6 mm | 9 mm | |
| 6 mm | 10 mm | |
| 6 mm | 11 mm | |
| 6 mm | 12 mm | |
| 6 mm | 13 mm | |
| 6 mm | 14 mm | |
| 6 mm | 15 mm | |
| 6 mm | 16 mm | |
| 7 mm | 6 mm | Different medial and lateral spacer, trial, and/or insert height (7 mm medial spacer, trial, and/or insert height with various lateral spacer, trial, and/or insert heights) |
| 7 mm | 8 mm | |
| 7 mm | 9 mm | |
| 7 mm | 10 mm | |
| 7 mm | 11 mm | |
| 7 mm | 12 mm | |
| 7 mm | 13 mm | |
| 7 mm | 14 mm | |
| 7 mm | 15 mm | |
| 7 mm | 16 mm | |
| 8 mm | 6 mm | Different medial and lateral spacer, trial, and/or insert height (8 mm medial spacer, trial, and/or insert height with various lateral spacer, trial, and/or insert heights) |
| 8 mm | 7 mm | |
| 8 mm | 9 mm | |
| 8 mm | 10 mm | |
| 8 mm | 11 mm | |
| 8 mm | 12 mm | |
| 8 mm | 13 mm | |
| 8 mm | 14 mm | |
| 8 mm | 15 mm | |
| 8 mm | 16 mm | |
| 9 mm | 6 mm | Different medial and lateral spacer, trial and/or insert height (9 mm medial spacer, trial, and/or insert height with various lateral spacer, trial, and/or insert heights) |
| 9 mm | 7 mm | |
| 9 mm | 8 mm | |
| 9 mm | 10 mm | |
| 9 mm | 11 mm | |
| 9 mm | 12 mm | |
| 9 mm | 13 mm | |
| 9 mm | 14 mm | |
| 9 mm | 15 mm | |
| 9 mm | 16 mm | |
| 10 mm | 6 mm | Different medial and lateral spacer, trial, and/or insert height (10 mm medial spacer, trial, and/or insert height with various lateral spacer, trial, and/or insert heights) |
| 10 mm | 7 mm | |
| 10 mm | 8 mm | |
| 10 mm | 9 mm | |
| 10 mm | 11 mm | |
| 10 mm | 12 mm | |
| 10 mm | 13 mm | |
| 10 mm | 14 mm | |
| 10 mm | 15 mm | |
| 10 mm | 16 mm | |
| 11 mm | 6 mm | Different medial and lateral spacer, trial, and/or insert height (11 mm medial spacer, trial, and/or insert height with various lateral spacer, trial, and/or insert heights) |
| 11 mm | 7 mm | |
| 11 mm | 8 mm | |
| 11 mm | 9 mm | |
| 11 mm | 10 mm | |
| 11 mm | 12 mm | |
| 11 mm | 13 mm | |
| 11 mm | 14 mm | |
| 11 mm | 15 mm | |
| 11 mm | 16 mm | |
| 12 mm | 6 mm | Different medial and lateral spacer, trial, and/or insert height (12 mm medial spacer, trial, and/or insert height with various lateral spacer, trial, and/or insert heights) |
| 12 mm | 7 mm | |
| 12 mm | 8 mm | |
| 12 mm | 9 mm | |
| 12 mm | 10 mm | |
| 12 mm | 11 mm | |
| 12 mm | 13 mm | |
| 12 mm | 14 mm | |
| 12 mm | 15 mm | |
| 12 mm | 16 mm | |
| 13 mm | 6 mm | Different medial and lateral spacer, trial, and/or insert height (13 mm medial spacer, trial, and/or insert height with various lateral spacer, trial, and/or insert heights) |
| 13 mm | 7 mm | |
| 13 mm | 8 mm | |
| 13 mm | 9 mm | |
| 13 mm | 10 mm | |
| 13 mm | 11 mm | |
| 13 mm | 12 mm | |
| 13 mm | 14 mm | |
| 13 mm | 15 mm | |
| 13 mm | 16 mm | |
| 14 mm | 6 mm | Different medial and lateral spacer, trial, and/or insert height (14 mm medial spacer, trial, and/or insert height with various lateral spacer, trial, and/or insert heights) |
| 14 mm | 7 mm | |
| 14 mm | 8 mm | |
| 14 mm | 9 mm | |
| 14 mm | 10 mm | |
| 14 mm | 11 mm | |
| 14 mm | 12 mm | |
| 14 mm | 13 mm | |
| 14 mm | 15 mm | |
| 14 mm | 16 mm | |
| 15 mm | 6 mm | Different medial and lateral spacer, trial, and/or insert height (15 mm medial spacer, trial, and/or insert height with various lateral spacer, trial, and/or insert heights) |
| 15 mm | 7 mm | |
| 15 mm | 8 mm | |
| 15 mm | 9 mm | |
| 15 mm | 10 mm | |
| 15 mm | 11 mm | |
| 15 mm | 12 mm | |
| 15 mm | 13 mm | |
| 15 mm | 14 mm | |
| 15 mm | 16 mm | |
| 16 mm | 6 mm | Different medial and lateral spacer, trial, and/or insert height (16 mm medial spacer, trial, and/or insert height with various lateral spacer, trial, and/or insert heights) |
| 16 mm | 7 mm | |
| 16 mm | 8 mm | |
| 16 mm | 9 mm | |
| 16 mm | 10 mm | |
| 16 mm | 11 mm | |
| 16 mm | 12 mm | |
| 16 mm | 13 mm | |
| 16 mm | 14 mm | |
| 16 mm | 15 mm | |

In various exemplary embodiments for knee implantation procedures, a surgeon may employ separate (or a composite) medial and/or lateral measuring tools/spacers (or trials or inserts) to facilitate the determination of an optimized combination of medial or lateral tibial components, for example, with regard to medial and lateral composite thickness, insert thickness and/or medial and lateral implant or insert profile. Thus, medial and/or lateral tibial implant or component or insert thickness can be optimized for a desired soft-tissue or ligament tension or ligament balance for different flexion and extension angles and other joint poses. Such an arrangement can offer a unique benefit beyond traditional balancing using bone cuts and soft-tissue releases. In one embodiment, the surgeon can initially place desired tibial and femoral surgical bone cuts without preliminary measurement and/or balancing, and perform virtually all of the proper soft-tissue or ligament tensioning and/or kinematic balancing entirely via selection of a one or more desired medial and/or lateral tibial insert or composite thicknesses and/or profile. Of course, if desired, additional adaptation and optimization of bone cuts and soft-tissue releases is possible (as described herein).

Those of skill in the art should also appreciate that a combination of standard and customized components may be used in conjunction with each other. For example, a standard tray component may be used with an insert component that has been individually constructed for a specific patient based on the patient's anatomy and joint information. Various embodiments can incorporate a tray component with an insert component shaped so that once combined, they create a uniformly shaped implant matching the geometries of the patient's specific joint.

Figure 11A:
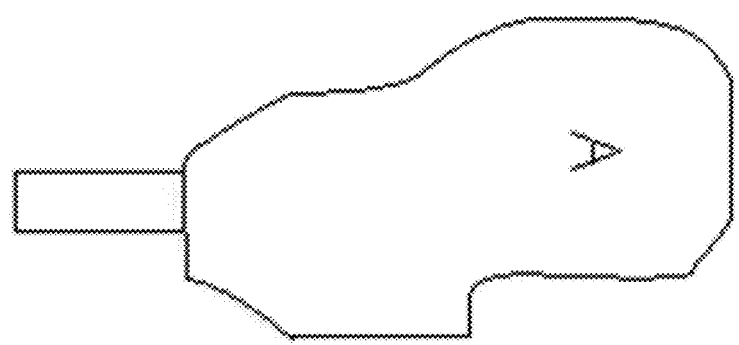
FIGS. 11A and 11B depict top and side views of a series of individual spacers used in knee arthroplasty procedures for adjusting and optimizing alignment, tension, balance, and position during a knee implant surgery.
Figure 11B:
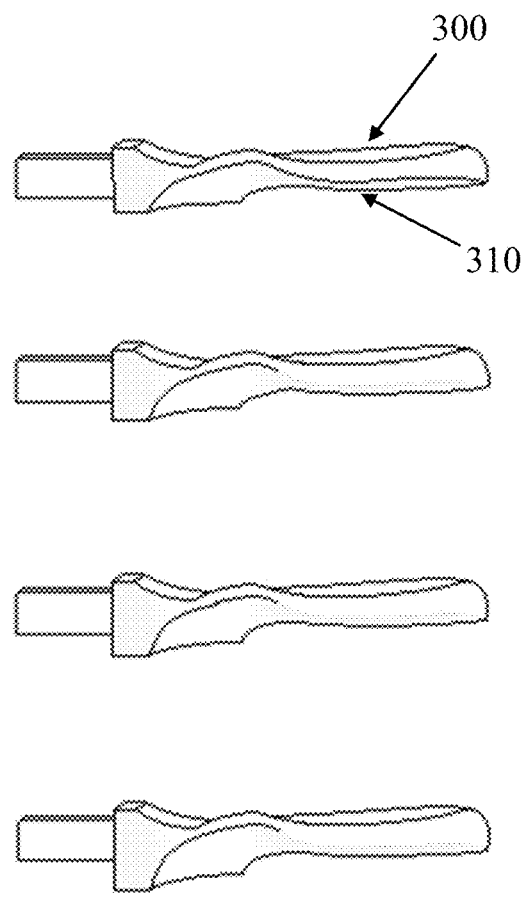

FIGS. 11A and 11B depict a series of spacers or trials or inserts that can be used in knee arthroplasty procedures for adjusting and optimizing alignment, tension, balance, and position (e.g., as described in Table 2 above) during a knee implant surgery. In particular, FIG. 11A depicts a medial balancer chip insert from top view to show the superior surface of the chip. FIG. 11B depicts a side view of a set of four medial balancer chip inserts that incrementally increase in thickness by 1 mm. A corresponding set of lateral balancing chip inserts (having a range of thicknesses) can be used in conjunction with a set of medial balancing chip inserts. Using such devices, the joint can be optimized using independent medial and lateral balancing chips inserts having different thicknesses. As indicated with the first chip in the figure, a superior surface 300 of the balancing chip insert is intended to engage a corresponding surface of the femur, and an inferior surface 310 desirably engages a corresponding surface on the tibia. In various embodiments, one or both of the superior surface 300 and/or the inferior surface 310 can be patient-adapted to fit the particular patient. In certain embodiments, a balancing chip can include a resection surface to guide a subsequent surgical bone cut.

Figure 12A:
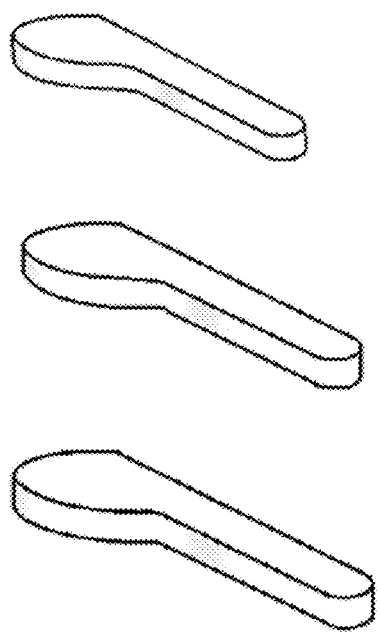
FIG. 12A depicts a set of three individual medial spacer block inserts having incrementally increasing thicknesses.

FIG. 12A depicts a set of three medial spacer block inserts having incrementally increasing thicknesses, for example, thicknesses that increase by 1 mm, by 1.5 mm, or by 2 mm. A corresponding set of lateral medial spacer block inserts (having a range of thicknesses, which can be the same or different thicknesses than those of the medial blocks) can be used in conjunction with a set of medial spacer block inserts. A spacer block insert can be used, for example, to provide the thickness of a tibial implant component (optionally with or without the additional thickness of a tibial implant component insert) during subsequent implantation steps and prior to placement of the tibial implant component. In certain embodiments, the spacer block insert can include a portion for attaching a trial a tibial implant component insert, so that the precise thicknesses of different combinations of tibial implant components and component inserts can be assessed. By using medial and lateral spacer block inserts of different thicknesses, the balancing, tensioning, alignment, and/or positioning of the joint can continue to be optimized throughout the implantation procedure. In certain embodiments, one or more features of a spacer block insert can be patient-adapted to fit the particular patient. In certain embodiments, a spacer block insert can include a feature for attaching or stabilizing a cutting guide and/or a feature for guiding a cutting tool.

Figure 12B:
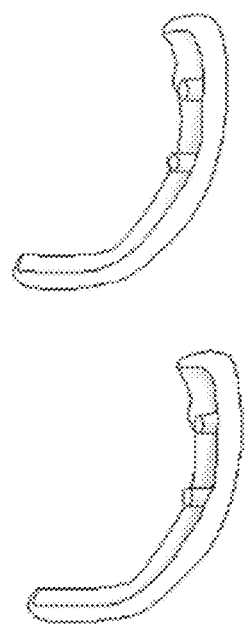
FIG. 12B depicts a set of two individual medial femoral trials having incrementally increasing thicknesses.

FIG. 12B depicts a set of two medial femoral trials having incrementally increasing thicknesses, for example, thicknesses that increase by 1 mm, by 1.5 mm, or by 2 mm. A corresponding set of lateral femoral trials (having a range of thicknesses) can be used in conjunction with the set of medial femoral trials. A femoral trial can be used, for example, to test variable thicknesses and/or features of a femoral implant component during implantation steps prior to placement of the tibial implant component. By using medial and lateral femoral trials of different thicknesses, the balancing, tensioning, alignment, and/or positioning of the joint can continue to be optimized throughout the implantation procedure. In certain embodiments, one or more features of a femoral trial can be patient-adapted to fit the particular patient. In certain embodiments, a femoral trial can include a feature for attaching or stabilizing a cutting guide and/or a feature for guiding a cutting tool. Furthermore, a spacer, such as a lateral spacer, can be used for balancing to equal distal asymmetry.

Figure 12C:
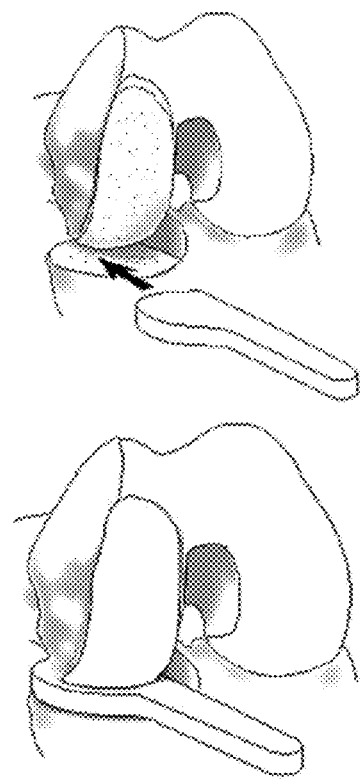
FIG. 12C depicts a medial femoral trial in place and a standard spacer block being inserted to evaluate the balance of the knee in flexion, extension or other orientation.

FIG. 12C depicts one embodiment of a medial femoral trial in place and a standard spacer block being inserted to evaluate the balance of the knee in flexion and extension. Spacer blocks having different thicknesses can be inserted and evaluated until an optimized thickness is identified. Optionally, a lateral femoral trial also can be placed between the lateral portions of the femur and tibia and a lateral spacer block inserted and evaluated along with the medial spacer block. Medial and lateral spacer blocks having different thicknesses can be placed and removed until a desired tension is observed medially and laterally throughout the patient's range of motion. Then, a tibial implant component and/or tibial implant component insert can be selected to have a thickness based on the thickness identified by evaluation using the femoral trial and spacer block. In this way, the selected medial tibial implant component (and/or tibial implant component insert) and the lateral tibial implant component (and/or tibial implant component insert) can have different thicknesses. As desired, medial and lateral balancing chips having different thicknesses can be placed in the joint space until a desired tension is observed medially and laterally throughout the patient's range of motion.

While the use of multiple spacers, trials, inserts and/or balancing chips is well known in the art, such systems typically employ a multiplicity of such spacers, including spacers for differing points in the surgical procedure (i.e., one set of spacers to balance the native joint, and another set to balance the joint after implant insertion), all of which can occupy significant space in the sterile surgical filed, and necessitate multiple tool exchanges between the surgeon and back-table personnel during the surgical procedure. In contrast, the various devices, procedures and methods disclosed herein significantly reduce the number of such measuring and balancing tools required during a given surgical procedure, significantly improving the surgical procedure.

Figure 13:
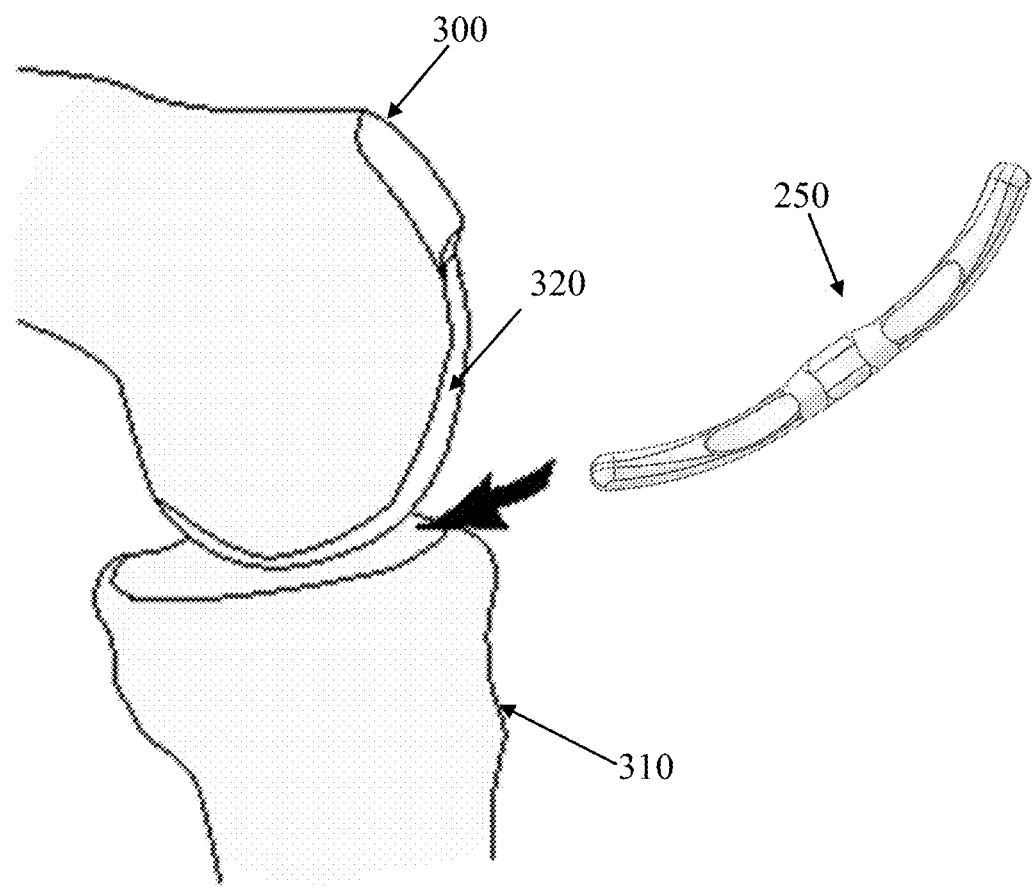
FIG. 13 depicts the probe/tool of FIG. 9 being inserted in flexion between a femur and a tibia.

FIG. 13 depicts the measuring tool 250 or spacer of FIGS. 9 and 10 being inserted in flexion between a femur 300 and a tibia 310. In this embodiment, a subchondral bone surface 320 of the femur has been exposed prior to the insertion of the measurement tool, although insertion of tools against existing articular surfaces are also contemplated by the present disclosure. Once the tool is inserted by the surgeon, if the distraction force (and related tension/laxity of the distracted joint) are deemed insufficient or unacceptable by the surgeon, the tool may be withdrawn, reversed, and the opposing measuring surface of the tool may be inserted in a similar manner. In this way, the surgeon need not exchange the spacer for another spacer of differing shape or size, but need merely use another measuring surface on the same tool.

Figure 14:
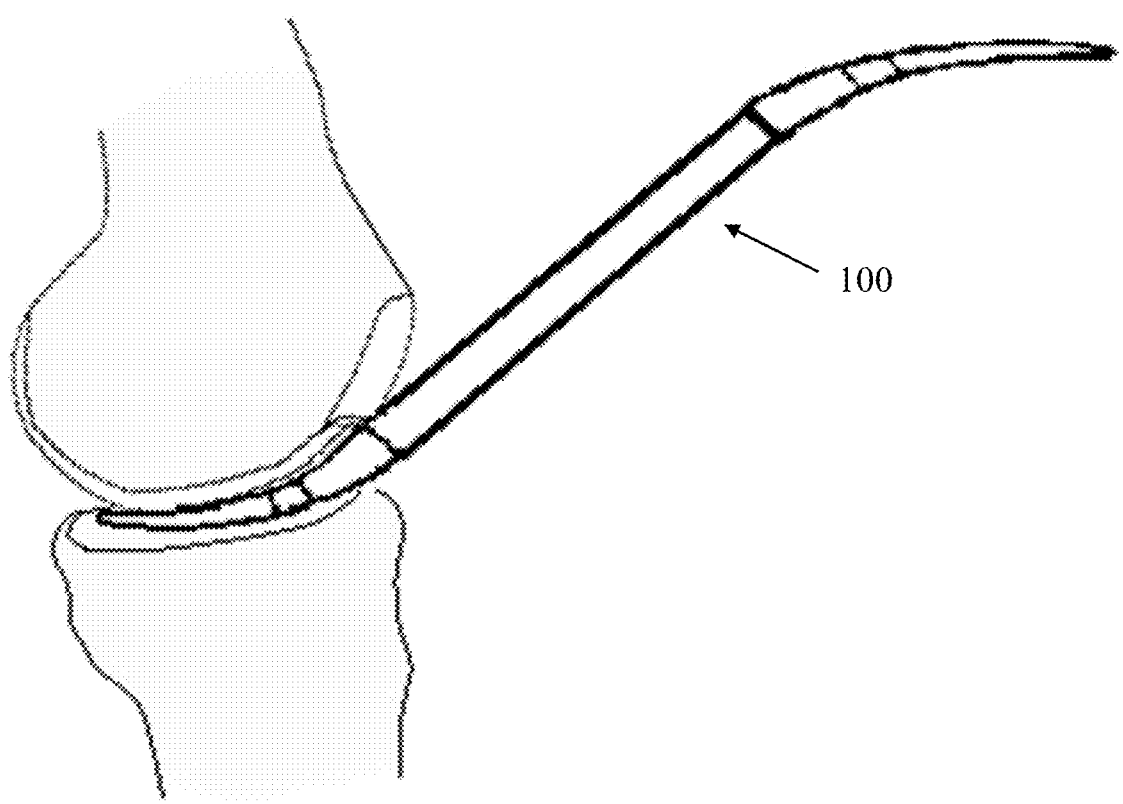
FIG. 14 depicts the probe/tool of FIG. 4 inserted in a desired position in a knee joint brought into extension.

FIG. 14 depicts the assessment probe or measuring tool 100 of FIG. 4 inserted in a desired position while a knee joint is brought into extension. Optionally, a lateral spacer (not shown) can be placed between the lateral portions of the femur and tibia, or a multi-pronged tool, such as shown in FIG. 5, can be inserted into both medial and lateral compartments simultaneously. The tool 100 can be advanced into and/or withdrawn from the knee joint, progressively increasing and/or decreasing the distraction between the femur and tibia until a desired distraction and/or balancing has been obtained. If the tool cannot obtain the desired distraction, the tool can be withdrawn, reversed, and the opposing measuring wedge on the other side of the tool can be inserted and/or manipulated in like fashion. In this way, the surgeon need not exchange the spacer for another spacer of differing shape or size, but can simply employ another measuring surface on the same tool.

In various embodiment, one or more measuring tools 100, 200 and 250 (of varying heights) similar to the various embodiments described herein can be placed between the surface of a tibia (cut or uncut) and the uncut posterior femoral condyles of a femur (with the femur in flexion) until proper alignment and orientation of the flexion gap is reached, and then a cut guide or other instrument (not shown) could be positioned relative to the measuring tool (at the surgeon's preference) and then the guide is pinned or otherwise secured in place and the measuring tool removed. The guide may include various alignment features which can be used by the surgeon to align the posterior femoral cuts. The cuts may be asymmetric, as desired, typically representing asymmetric posterior cut locations on the implant, and they allow fine-tuning of the external femoral rotation of the joint replacement. In various embodiments, the outer perimeters of the various measuring tool(s) or other instruments may match some or all of the perimeter (cut and/or uncut) of the adjacent bone or bones, or may otherwise incorporate indicia identifying the margins of such adjacent surfaces.

Using the various tools described herein, the knee joint can be flexed and the flexion gap can be evaluated. In addition, the knee can be extended and the extension gap can be evaluated. As desired, intermediate and/or other positions of the joint can be assessed. Ultimately, the surgeon can select an optimal combination of spacers or trials for a given joint, instrument, trial or mold. A surgical cut guide can be applied to the trial, instrument, or mold with the measuring tool optionally interposed between the trial, instrument or mold and the cut guide. In this manner, the exact position of the surgical cuts can be influenced and can be adjusted to achieve an optimal result. Someone skilled in the art will recognize other means for optimizing the position of the surgical cuts. For example, expandable or ratchet-like devices could be utilized that could be inserted into the joint or that can be attached or that can touch the trial, instrument or mold. Hinge-like mechanisms could be applicable. Similarly, jack-like mechanisms might be useful. The measuring tools and any instrumentation such as trials, other spacers and/or ratchets could be combined with a tensiometer to provide a better intraoperative assessment of the joint. The tensiometer can be utilized to further optimize the anatomic alignment and tightness or laxity of the joint and to improve post-operative function and outcomes. Optionally, local contact pressures or range of motion may be evaluated intraoperatively, for example using a sensor like the ones manufactured by Tekscan, South Boston, Mass.

Figure 15A:
FIG. 15A depicts an exemplary set of three individual medial tibial component inserts having incrementally increasing thicknesses.
Figure 15A:
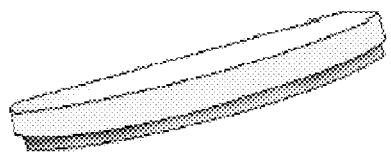
Figure 15A:
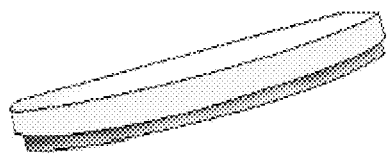
Figure 15B:
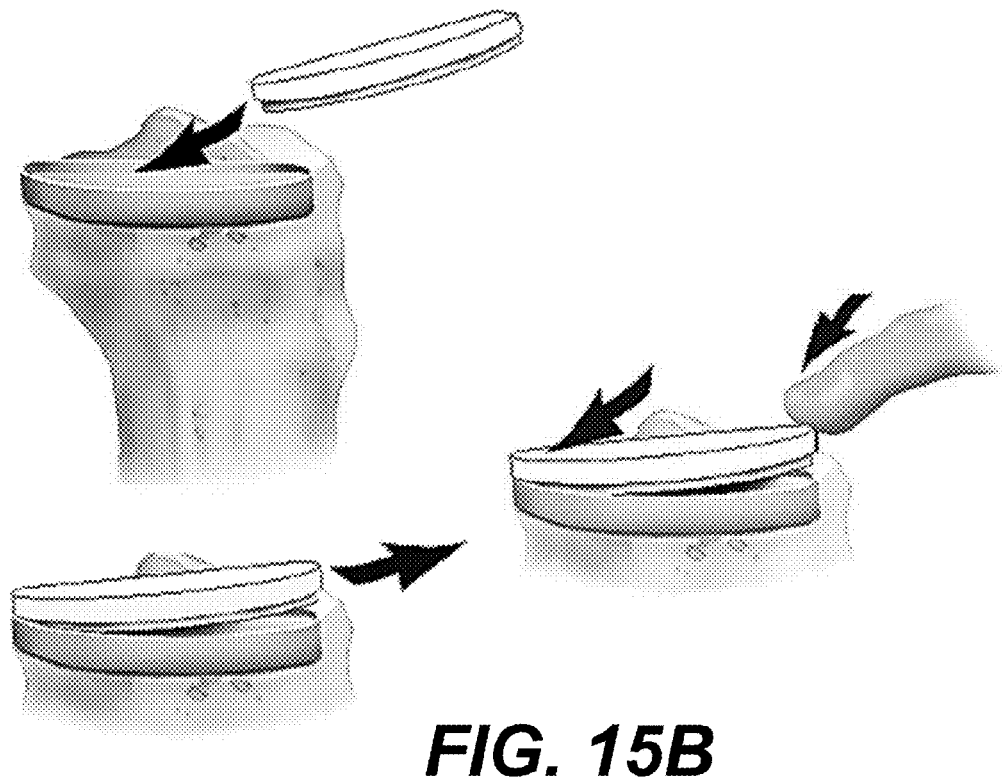
FIG. 15B depicts a process of placing and/or adding various tibial component inserts.

As previously noted, various embodiments described herein, including the measurement tools of FIGS. 4, 5, 7 and 9, can be utilized to replace and/or augment the various combinations of individual spacers and trials described herein for assessment and/or balancing of joint structures. FIG. 15A depicts an exemplary set of three individual medial tibial component inserts having incrementally increasing thicknesses, for example, thicknesses that increase by 0.5 mm, by 1 mm, by 1.5 mm, or by 2 mm. A corresponding set of individual lateral tibial component inserts (having a range of thicknesses) can be used in conjunction with the set of medial tibial component inserts. A measuring tool as described herein can be used, for example, to determine the best insert thickness and/or features of a tibial component insert during the final implantation steps. By using medial and lateral tibial component inserts of different thicknesses and/or configurations, the balancing, tensioning, alignment, and/or positioning of the joint can be optimized even in the final steps of the procedure. In certain embodiments, one or more features of a tibial component insert can be patient-adapted to fit the particular patient. FIG. 15B depicts the process of placing and/or adding (and possibly removing) various tibial component inserts, including the final placement of a selected tibial component insert.

In various embodiments, the balancing and optimization of kinematics techniques described herein will properly align a desired external rotation to the knee prosthesis prior to insertion of a tibial tray and tibial insert. Desirably, the first and/or second sides of a measuring tool or tools are positioned and aligned such that, when the replacement femoral condylar surfaces contact the tool, the implant "tilts" or externally rotates the femoral component a desired amount, which in one example can be approximately 5.77 degrees. Once the proper measurements are determined, the surgeon can choose a corresponding tibial spacer and tibial tray combination that achieves this same desired alignment for the femoral component.

Figure 16A:
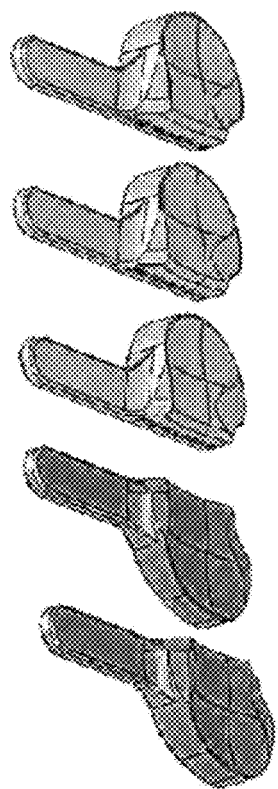
FIG. 16A depicts a series of individual tibial trial spacers designed for use in assessing a patient's joint structures.

In one exemplary embodiment of a knee joint replacement procedure, one or more measuring tools as described herein can be utilized in place of a set of standard tibial trial spacers, shown in FIG. 16A, that have been designed and included for use in assessing a patient's joint structures. Specifically, a standard set of two medial trial spacers in thicknesses of 6 mm and 8 mm, and three lateral trial spacers can be provided in thicknesses of 8 mm, 10 mm, and 11 mm, can be replaced by a single instrument, such as a measuring instrument similar to the one shown in FIG. 8. In such an embodiment, the measuring portions of the instrument can be utilized in a manner similar to the spacers to assess balance and fit, for example, to assess the tightness and balance of the joint with the spacer in place to represent tibial implant thickness between the cut tibia and femur (and optionally other components in place representing femoral thickness) during flexion and extension of the knee.

Figure 16B:
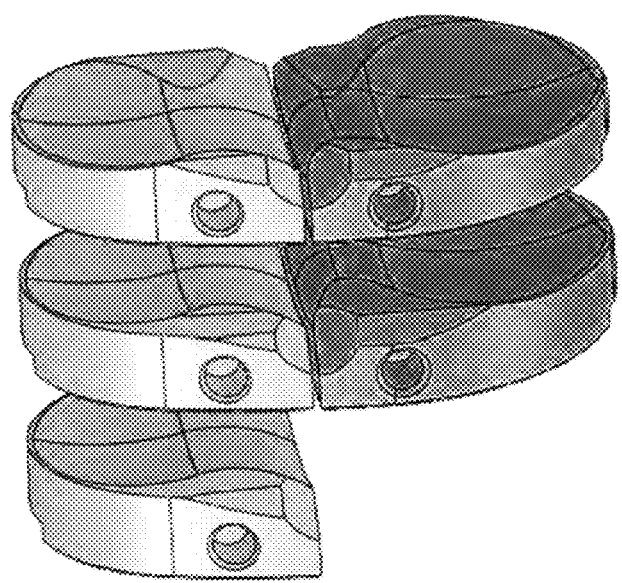
FIG. 16B depicts a set of individual tibial implant component trial inserts designed to assess the appropriate thicknesses of medial and lateral tibial implant component inserts for properly balancing the patient's knee joint.
Figure 17A:
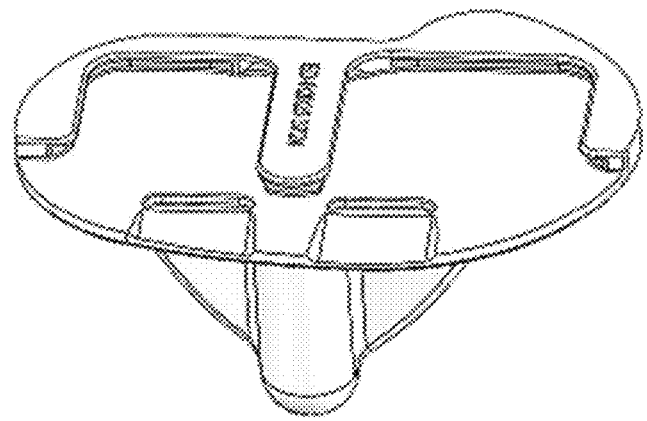
FIGS. 17A and 17B depict an exemplary tibial implant tray and associated tray inserts used in a knee joint balancing procedure.
Figure 17B:
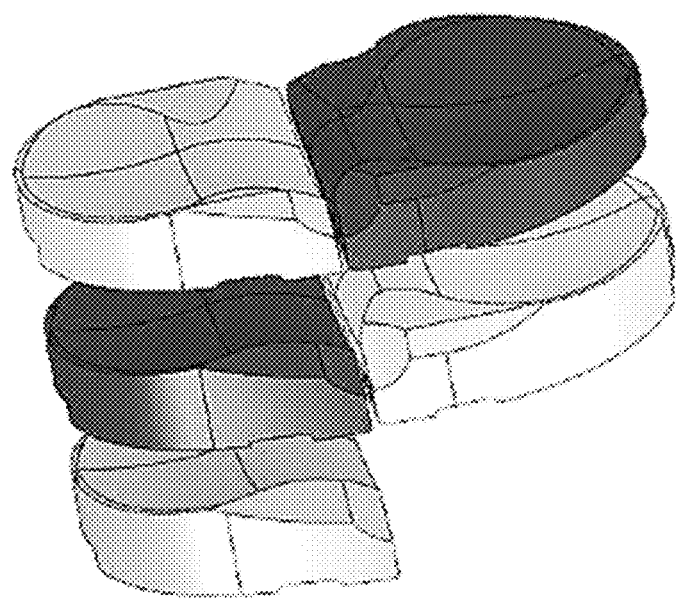

In another exemplary embodiment of a knee joint replacement procedure, one or more measuring tools as described herein can be utilized in place of a set of tibial implant component trial inserts, such as the ones shown in FIG. 16B, which have been designed and included for a patient in order for the surgeon to assess the appropriate thicknesses to use for medial and lateral tibial implant component inserts for properly balancing the patient's knee joint. Specifically, a set of two medial trial inserts and three lateral trial inserts can be replaced by a single instrument, such as a measuring instrument similar to the one shown in FIG. 14. Specifically, the measuring tool can duplicate the distraction of the two medial trial inserts with thicknesses of 6 mm and 8 mm, respectively, as well as the distraction of the lateral trial inserts with thicknesses of 8.5 mm, 9.5 and 10.5 mm (or, alternatively, thicknesses of 9 mm, 10 mm, and 11 mm, or 8 mm, 9 mm, and 10 mm, etc.). After assessing the trial inserts and deciding on an appropriate medial and lateral insert thickness for balancing, the surgeon can position a tibial implant tray (see FIG. 17A) and associated inserts (see FIG. 17B) having the appropriate thicknesses medially and laterally.

If trial components are used, the surgeon can assess alignment and stability of the trial components and the joint. During this assessment, the surgeon may conduct certain assessment processes depending upon the relevant joint structures, including flexion, extension, lateral stability external/internal rotation, rotary laxity testing, range of motion testing (external rotation, internal rotation and elevation) and stability testing (anterior, posterior and inferior translation). In many of these tests, the surgeon can position the joint in a first position and visualize the joint directly (i.e., visually and/or via endoscopic optics) and/or by utilizing non-invasive imaging system such as a fluoroscope (i.e., activated by depressing a foot pedal actuator). If desired, the surgeon can then position the joint in a second position and once again visualize the joint directly (i.e., visually and/or via endoscopic optics) and/or by utilizing non-invasive imaging system such as a fluoroscope (i.e., by depressing a foot pedal actuator). If desired, a computing system can register and/or store the respective location data for display and/or calculation of rotation/kinematics for the surgeon and/or automated system to determine whether the data is acceptable for the patient and the product involved. If not, the computer can apply rules in order to generate and display suggestions for releasing ligaments or other tissue, or using other component sizes or types. Once the proper tissue releases have been made, if necessary, and alignment and stability are acceptable as noted quantitatively on screen about all axes, the relevant trial components may be removed and actual components installed, and assessed in performance in a manner similar to that in which the trial components were installed, and assessed. At any point in such assessments, the use of measuring tools as described herein may optionally be included in the assessment process. In alternative embodiments, the above-described assessment process can be utilized with the actual implant components installed, as opposed to trial components, as desired.

Once a desired size and/or shape of insert or inserts have been determined, the insert(s) can be "docked," implanted or otherwise secured to any relevant supporting structure and/or implant components, and the relevant soft tissue structures and surgical incision repaired and/or closed, in a typical manner. At the end of a case, all relevant anatomical and alignment information can be saved for the patient file. This can be of great assistance to the surgeon in the future, including for use in planning of future surgeries, as well as to facilitate assessment of the joint during post-operative recovery, as the outcome of implant positioning can be seen and assessed before the formation of significant scar tissues and/or additional anatomical or implant structural degradation that may occur.

In one alternative embodiment, such as for replacement of a glenoid component of a shoulder joint, a metal backed glenoid tray component may be used with one or more polyethylene inserts. The polyethylene will typically have a curved portion designed to mate with an opposing humeral head (natural and/or artificial) in a low friction form. This mating can be optimized by selecting a polyethylene insert that is optimized or achieves an optimal fit with regard to one or more of: depth of the concavity, width of the concavity, length of the concavity and/or radius or radii of curvature of the concavity. A glenoid insert and opposing humeral head surface can have can have a single or a composite radius of curvature in one or more dimensions, e.g., the coronal plane. They can also have multiple radii of curvature. Using measuring devices similar to those described herein, and particularized for the native anatomy of shoulder joints, similar matching of polyethylene or other plastic shape to opposing metal or ceramic component shape (and appropriate balancing and kinematic performance) of the joint can be performed.

If desired, a measuring tool, jig or other measurement device can be employed or utilized to determine and/or measure the relationship between a bone anchor, glenoid plate or other anatomical feature and a humeral stem (either statically and/or dynamically), with the resulting measurements used to determine appropriate combinations of implant components that can be used to optimize the resulting surgical repair. For example, the measurement of the anchor/plate and stem may indicate a need for an increased depth of the glenoid socket component, which may be accommodated by a glenoid "insert" having increased thicknesses at its peripheral walls (and/or an increased depth in the center of the insert cavity). Similarly, differing measurements may indicate a desire and/or need for differing humeral head designs and/or stem interfaces, as well as differing designs, angulations and/or shapes of glenoid implant components and/or glenoid inserts, which may be provided in multiple sizes and/or shapes including some patient-specific and/or patient-adapted features and other standard feature variations. In various exemplary embodiments, a glenoid implant insert could include a variety of inserts of differing thicknesses, including eccentric thickness that may alter the orientation and/or angulation of the resulting glenoid articulating surface(s) relative to the scapula and/or humerus. Similarly, a variety of inserts could include differing diameters and/or depths of the joint-facing concave surface as well as alterations and/or variations to the implant/surface rotational alignment relative to the glenoid axis, the flexion/extension angle and the version/retroversion angle. In various embodiments, the glenoid tray could include a first insert that establishes a desired glenoid articulating surface, and a second insert that establishes a desired glenoid rim geometry and/or thickness (i.e., a labrum replacement insert), with the two inserts connecting to the tray and/or each other in various arrangements. Following implantation of desired implant components, the soft tissue balance and/or other kinematics of the shoulder joint can again be assessed, and then the split in the rotator interval can be closed. The deltoid can be repaired back to the acromion. Subcutaneous tissues and skin can then be closed per the surgeon's usual routine.

Surface Features

In various embodiments, an assessment probe or measuring tool can include a plurality of measuring portions, with each portion including one or more surfaces designed and/or selected using a variety of patient-specific, patient-adapted, patient-engineered and/or standard features. For example, sets of measuring tools can be designed and/or selected to have femoral and/or tibial-specific surface features, as well as different bone-facing and/or joint-facing surfaces on a single tool from which the surgeon can select the optimum available surface for further steps in the procedure.

The various surfaces of a measuring tool can have a standard geometry in one or more dimensions or can be completely standard. The various surfaces of the measuring tools can also include patient specific or patient derived shapes. For example, in a shoulder joint, one measuring tool surface can be derived using the curvature or shape of the cartilage or subchondral bone of the patient, on the glenoid or the humeral side, in one or more dimensions or directions. Alternatively, the measuring tool surface for use in contact with an adjacent humeral component can be derived using the curvature or shape of the cartilage or subchondral bone of the patient on the humerus or glenoid in one or more dimensions or directions, or the measuring tool surface can be selected or adapted or designed based on the humeral component implant shape. The selection, adaption or design can occur using a set of rules, e.g. desirable humeral to glenoid articular surface radius ratios, in one or more planes, e.g. superoinferior or mediolateral.

Depending upon the relevant surface and/or structure measured, as well as the measurement locations and/or techniques (i.e., static or dynamic measurements), the tool surface can include a variety of surface shapes, sizes and/or features. For example, where a measuring tool is used to determine the condition of a joint prior to modification of anatomical surfaces, the upper and lower surfaces (or other opposing surfaces) of a given measuring portion can comprise surfaces that mirror and/or otherwise accommodate the natural shape of the relevant anatomy. In the case of a knee joint, such a measuring portion may include an upper surface formed in a relatively concave shape in one or more directions (to accommodate the convex surface of the opposing femoral condyle) while a lower surface can have a relatively convex shape in one or more directions (to accommodate the relatively concave surface of the opposing tibial condyle). Various combinations of irregular, flat, curved, convex and/or convex shapes can be included in and/or on a single surface, if desired.

In contrast, where a measuring tool is used to determine the condition of a joint after modification of one or more anatomical structures, the upper and/or lower surfaces (or other opposing surfaces) of a given measuring portion can comprise surfaces that mirror and/or otherwise accommodate the modified anatomical structure, as well as accommodate any remaining natural anatomy (i.e., a planar cut on a tibial surface and a natural surface on the opposing femoral condyle) and or other features on one or both sides of the measuring element.

In a similar manner, various embodiments may include surface features corresponding to joint implant components, trials or other surgical tools, which can facilitate assessment of the joint within the presence of such objects. For example, in the case of a knee joint with an implanted tibial tray, the measuring tool may include a lower surface corresponding to the relative flat portion of the tray, while an upper surface can correspond to a natural anatomical surface, a modified anatomical surface and/or an implant component or trial (as desired).

Various combinations of surface features can be utilized with a given measurement tool, including curved, flat, convex, concave, planar, irregular and/or other features, including features corresponding to natural or modified anatomy and/or surface features of implant components, trial and/or other surgical tools.

In various embodiments, such as shown in FIG. 6, a single measurement tool or tools can include measuring elements having surfaces, surface features and characteristics for measuring and/or assessing joints at various stages of the surgical procedure. For example, a single measuring element may include a surface pair for measuring and/or assessing a natural anatomy between a femur and a tibia, and a rotated section of the same measuring element may include a surface pair for measuring and/or assessing a modified anatomy between a femur and a tibia (i.e., assessing a femoral and/or tibial resection). In this manner, a single measuring tool or reduced number of such measuring tools can be provided for use by the surgeon.

Access and/or Directionally Dependent Features

In various embodiments, a variety of features and/or attributes of a given measuring tool or tools may become more or less desirable (and potentially could be modified, designed and/or selected) based upon the size, directionality and/or type of surgical access technique used to access the anatomical joint structures. In such instances, the various measuring tools will desirably be designed/selected and/or modeled to accommodate and/or facilitate a specific type and/or orientation of surgical access procedure along a defined access path or paths.

Figure 19:
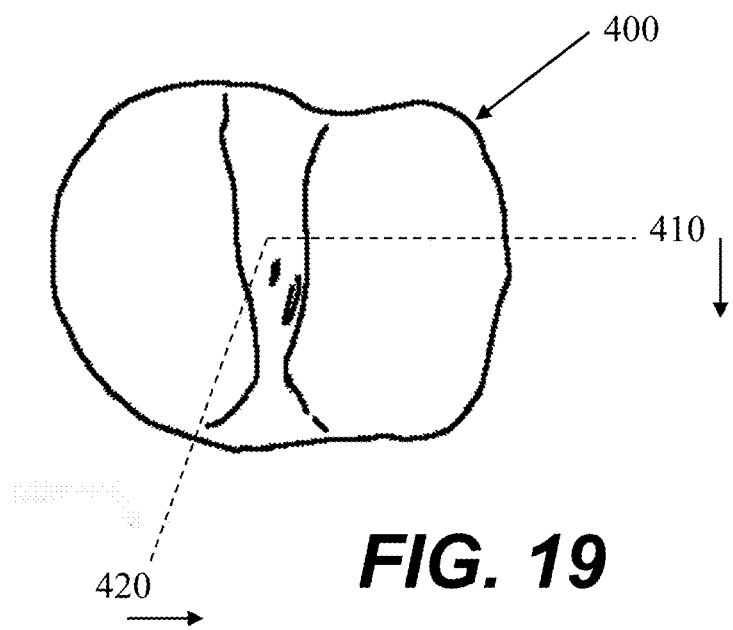
FIGS. 19 and 20 depict an exemplary tibial plateau and anterior surgical access path to a knee joint.
Figure 20:
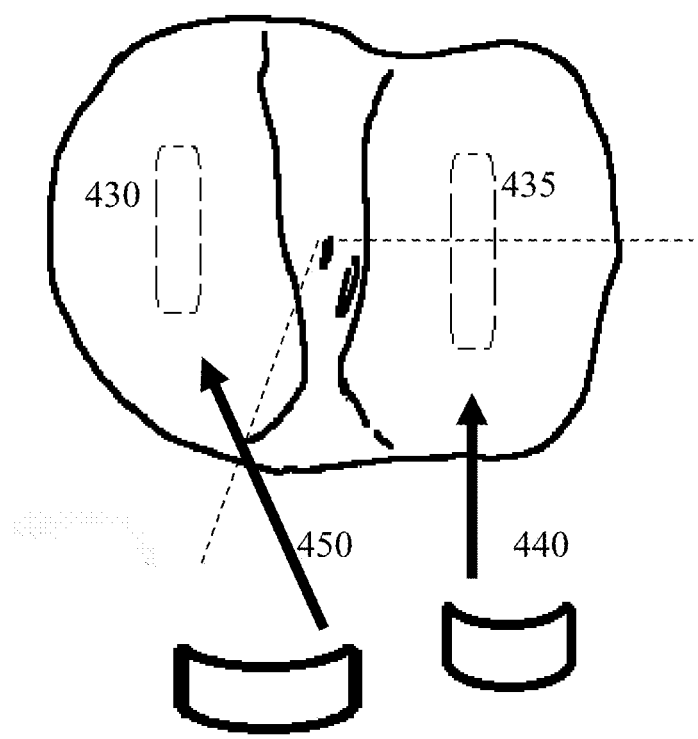

For example, where an anterior surgical access path to a knee joint is contemplated (see FIGS. 19 and 20), it may be desirous to design and/or select measuring tools to easily pass through the surgical incision(s), and be placed in the targeted anatomy along the access path and within the anticipated readily-available surgical volume. In one example, a measuring tool may include an upper surface that mirrors or otherwise replicates a general coronal curvature of a femoral condyle as seen along an anterior-posterior direction 440. However, where the access path to a tibial plateau 400 may be from a more medial direction (see 450), the upper surface of the measuring tool may have an expanded or otherwise altered curvature or other surface features to accommodate an "off-axis" approach to the femoral condyle. This is because the longitudinal axis of one condyle 430 may not be accessible in a parallel orientation via the access window (the surgical "window" is indicated by the arrows 420 and 410) as compared to the access to the other condyle 435.

In a similar manner, measuring tool design may be impacted by intervening anatomical features such as osteophytes, ligaments, incision borders and/or the presence of other surgical tools and/or implant components. In a similar manner, the handle or other feature of the measuring tool may be modified depending upon the intended surgical access path, with varying lengths, shapes, sizes and/or curvatures (including compound curvatures) of the handle and/or relevant measuring portions based on available access paths and/or "real estate" available within and adjacent to the surgical field. In various embodiments, measuring tools may align with various anatomical features that are directly exposed along a preferred access path, while other anatomical features may still be masked by overlying tissues. Depending upon surgeon preference and training, the incision through the skin may be shorter than the area opened in the muscle. The incision can be used to achieve access to the muscle that is around the various portions of the anatomy selected to be resected.

The use of fluoroscopic, MRI or other actual images of body parts can facilitate the modeling and/or construction of surgical instruments and/or the position and orientation of body parts. Various anatomical information can be derived and utilized in the assessment of the anatomical structures, as well as the planning of the surgical procedure and associated implants/tools. For example, resection planes, anatomical axes, mechanical axes, anterior/posterior reference planes, medial/lateral reference planes, rotational axes or any other navigational or kinematic references or information can be useful or desired in planning or executing surgery. Desirably, measuring tools will be designed and/or selected in connection with the design and/or selection of patient-specific and patient-adapted implant component and/or jigs. The various tool designs desirably guide the surgeon in performing one or more patient-specific cuts or other surgical steps to the bone or other tissues so that the cut bone surface(s) negatively-match or otherwise accommodate corresponding surfaces (such as patient-specific bone-cut-facing surfaces) of the implant component while obtaining a desired balancing and/or kinematic alignment of the joint. In addition to the design and/or selection of appropriate implant components, anatomical modeling (as well as other patient-specific data and/or patient-adapted models) can be utilized to design and/or select appropriate surgical procedural steps and surgical preparation of the various anatomical surfaces. The creation of patient-specific and/or patient-adapted surgical cutting and reaming tools, and associated assessment, measuring and/or guide tools, can significantly facilitate the accuracy and outcomes of a joint replacement/resurfacing procedure.

Alignment Indicators and Markings

In various embodiments, a visible or tactile mark, orientation or indication feature can be included or incorporated into one or more aspect of an assessment or measuring tool. For example, an etching or other marking 280 (see FIG. 9) can desirably align with an anatomical or other feature (including implant component and/or jig features) when a measuring tool is in a desired position. If desired, such a marking 280 could align with a relevant bone feature (i.e., a perimeter of a tibial plateau during a knee replacement procedure) to indicate to the surgeon that the measuring tool has been fully advanced and positioned in a desired location/orientation for joint measurement and/or assessment. In another example, an etching or other marking could be aligned to point to a bicipital groove in a shoulder joint procedure. In other embodiments, the visible or tactile orientation feature could be a small protuberance or tab extending from the tool towards an anatomical feature and/or axis which may be relevant to the surgical procedure, as well as to align and position the measuring tool quickly and correctly. If desired, a projection or tab could be sized and shaped to be fit into a corresponding portion or recess of an adjacent anatomical feature.

In various embodiments, the measuring tool could have one or more marks or other indicators on a visible surface (e.g. a mark on a lateral surface pointing superiorly) to aid in the rotational alignment of the measuring tool. During surgery, the surgeon could use an electrocautery instrument (or other instrument) to mark a surface of an anatomical structure, with the instrument's mark eventually aligned to another surface mark (on the same measuring tool or a different tool, jig or implant/trial), which could potentially be visualized through slots or other openings on a subsequent instrument and/or implant component to verify the seating and proper orientation of the instrument.

Modeling and the Use of Models

A wide variety of imaging techniques, including Computerized Axial Tomography and/or Computed Tomography (CAT/CT) scans, Magnetic Resonance Imaging (MRI), and other known imaging techniques, can be used to obtain patient-specific anatomical information. In various embodiments, the patient-specific data can be utilized directly to determine the desired dimensions of the various implant components for use in the joint replacement/resurfacing procedure for a particular patient. Various alternative embodiments contemplate the use of computerized modeling of patient-specific data, including the use of kinematic modeling and/or non-patient data sources, as well as general engineering techniques, to derive desired dimensions of the various prostheses, surgical tools and techniques.

In certain embodiments, imaging data collected from the patient, for example, imaging data from one or more of x-ray imaging, digital tomosynthesis, cone beam CT, non-spiral or spiral CT, non-isotropic or isotropic MRI, SPECT, PET, ultrasound, laser imaging, photo-acoustic imaging, is used to qualitatively and/or quantitatively measure one or more of a patient's biological features, one or more of normal cartilage, diseased cartilage, a cartilage defect, an area of denuded cartilage, subchondral bone, cortical bone, endosteal bone, bone marrow, a ligament, a ligament attachment or origin, menisci, labrum, a joint capsule, articular structures, and/or voids or spaces between or within any of these structures. The qualitatively and/or quantitatively measured biological features can include, but are not limited to, one or more of length, width, height, depth and/or thickness; curvature, for example, curvature in two dimensions (e.g., curvature in or projected onto a plane), curvature in three dimensions, and/or a radius or radii of curvature; shape, for example, two-dimensional shape or three-dimensional shape; area, for example, surface area and/or surface contour; perimeter shape; and/or volume of, for example, the patient's cartilage, bone (subchondral bone, cortical bone, endosteal bone, and/or other bone), ligament, and/or voids or spaces between them.

In certain embodiments, measurements of biological features can include any one or more of the illustrative measurements identified in Table 3.

TABLE 3

Exemplary patient-specific measurements of biological features that can be used in the creation of a model and/or in the selection and/or design of a measuring tool

| Anatomical feature | Exemplary measurement |
| --- | --- |
| Joint-line, joint gap | Location relative to proximal reference point |
| | Location relative to distal reference point |
| | Angle |
| | Gap distance between opposing surfaces in one or more locations |
| | Location, angle, and/or distance relative to contra-lateral joint |
| Soft tissue tension and/or balance | Joint gap distance |
| | Joint gap differential, e.g., medial to lateral |
| Medullary cavity | Shape in one or more dimensions |
| | Shape in one or more locations |
| | Diameter of cavity |
| | Volume of cavity |
| Subchondral bone | Shape in one or more dimensions |
| | Shape in one or more locations |
| | Thickness in one or more dimensions |
| | Thickness in one or more locations |
| | Angle, e.g., resection cut angle |
| Cortical bone | Shape in one or more dimensions |
| | Shape in one or more locations |

TABLE 3-continued

Exemplary patient-specific measurements of biological features that can be used in the creation of a model and/or in the selection and/or design of a measuring tool

| Anatomical feature | Exemplary measurement |
|---|---|
| Endosteal bone | Thickness in one or more dimensions<br>Thickness in one or more locations<br>Angle, e.g., resection cut angle<br>Portions or all of cortical bone perimeter at an intended resection level<br>Shape in one or more dimensions<br>Shape in one or more locations<br>Thickness in one or more dimensions<br>Thickness in one or more locations<br>Angle, e.g., resection cut angle |
| Cartilage | Shape in one or more dimensions<br>Shape in one or more locations<br>Thickness in one or more dimensions<br>Thickness in one or more locations<br>Angle, e.g., resection cut angle |

Depending on the clinical application, a single or any combination or all of the measurements described in Table 3 and/or known in the art can be used, and can be incorporated into various features of a measuring tool. Additional patient-specific measurements and information that be used in the evaluation can include, for example, joint kinematic measurements, bone density measurements, bone porosity measurements, identification of damaged or deformed tissues or structures, and patient information, such as patient age, weight, gender, ethnicity, activity level, and overall health status. Moreover, the patient-specific measurements may be compared, analyzed or otherwise modified based on one or more "normalized" patient model or models, or by reference to a desired database of anatomical features of interest. Any parameter mentioned in the specification and in the various Tables throughout the specification including anatomic, biomechanical and kinematic parameters can be utilized in various joints. Such analysis may include modification of one or more patient-specific features and/or design criteria for the measuring tool, jig and associated implant components to account for any underlying deformity reflected in the patient-specific measurements. If desired, the modified data may then be utilized to choose or design an appropriate measuring tool to accommodate the modified features, and a final verification operation may be accomplished to ensure the chosen measuring tool is acceptable and appropriate to the original unmodified patient-specific measurements (i.e., the chosen tool will ultimately "fit" the original patient anatomy). In alternative embodiments, the various anatomical features may be differently "weighted" during the comparison process (utilizing various formulaic weightings and/or mathematical algorithms), based on their relative importance or other criteria chosen by the designer/programmer and/or physician.

Optionally, other data including anthropometric data may be added for each patient. These data can include but are not limited to the patient's age, gender, weight, height, size, body mass index, and race. Desired limb alignment and/or deformity correction can be added into the model. The position of bone cuts on one or more articular or other surfaces as well as the intended location of implant bearing surfaces on one or more articular surfaces can be entered into the model.

In various embodiments, patient-specific surgical instruments can include, for example, measuring tools, alignment guides, drill guides, templates and/or cutting/resection guides for use in joint replacement and/or resurfacing procedures and other procedures related to the various bones of the relevant joint structures. The various measuring tools described herein can be used either with conventional implant components or with patient-specific implant components that are prepared using computer-assisted image methods. The patient-specific instruments and any associated patient-specific implants can be generally designed and formed using computer modeling based on the patient's 3-D anatomic image generated from image scans including, X-rays, MRI, CT, ultrasound or other scans. The patient-specific instruments can have a three-dimensional engagement surface that is complementary and made to conformingly contact and match at only one position a three-dimensional image of the patient's bone surface (which can be imaged selectively with associated soft tissues or without soft tissue, i.e., an actual bone surface), by various methods. The patient-specific instruments can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a pre-operative plan.

Electronic systems and processes according to various embodiments of the disclosure can utilize computing capacity, including stand-alone and/or networked capacities, to determine and/or store data regarding the spatial aspects of surgically related items and virtual constructs or references, including body parts, implements, instrumentation, trial components, prosthetic components and anatomical, mechanical and/or rotational axes of body parts. Any or all of these may be physically or virtually connected to or incorporate any desired form of mark, structure, component, or other fiducial or reference device or technique which allows position and/or orientation of the item to which it is attached to be visually and/or tactily determined, as well as possibly sensed and tracked, either virtually or in physical space (i.e., for computation and/or display during a surgical operation), preferably in three dimensions of translations and varying degrees of rotation as well as in time, if desired. Systems and processes according to some embodiments of the disclosure can employ computing means to calculate and store reference axes of body components such as in joint arthroplasty, for example the anatomical and/or mechanical axes of the femur and tibia in a knee joint replacement procedure.

If desired, various computing systems may employ patient-specific and/or patient-adapted data and computer models to track the position of instrumentation and osteotomy guides "real time" so that bone resections will locate the implant position optimally, which can include locations aligned with the anatomical axis. Furthermore, during trial reduction of the relevant joint, such tracking systems can provide feedback on the balancing of the soft tissues in a range of motion and under stresses and can suggest or at least provide more accurate information than in the past about which ligaments the surgeon should release (or avoid releasing) in order to obtain correct balancing, alignment and stability. Systems and processes according to some embodiments of the present disclosure can also suggest modifications to implant size, positioning, and other techniques to achieve optimal kinematics, either prior to surgery during the design and/or selection/modification process for implants, tools and/or procedural steps, or during the surgical procedure itself. Various systems can also include databases of information regarding tasks such as ligament balancing, in order to provide suggestions to the implant designer and/or surgeon based on performance of test results as automatically calculated by such systems and processes.

Reference points and/or data for obtaining measurements of a patient's joint, for example, relative-position measurements, length or distance measurements, curvature measurements, surface contour measurements, thickness measurements (in one location or across a surface), volume measurements (filled or empty volume), density measurements, and other measurements, can be obtained using any suitable technique. For example, one dimensional, two-dimensional, and/or three-dimensional measurements can be obtained using data collected from mechanical means, laser devices, electromagnetic or optical tracking systems, molds, materials applied to the articular surface that harden as a negative match of the surface contour, and/or one or more imaging techniques described above and/or known in the art. Data and measurements can be obtained non-invasively and/or preoperatively. Alternatively, measurements can be obtained intraoperatively, for example, using a probe or other surgical device during surgery.

In certain embodiments, reference points and/or measurements, such as those described above, can be processed using mathematical functions to derive virtual, corrected features, which may represent a restored, ideal or desired feature from which a patient-adapted implant component can be designed. For example, one or more features, such as surfaces or dimensions of a biological structure can be modeled, altered, added to, changed, deformed, eliminated, corrected and/or otherwise manipulated (collectively referred to herein as "variation" of an existing surface or structure within the joint). While it is described in the knee and shoulder, these embodiments can be applied to any joint or joint surface in the body, e.g. a hip, ankle, foot, toe, elbow, wrist, hand, and a spine or spinal joints.

Once one or more reference points, measurements, structures, surfaces, models, or combinations thereof have been selected or derived, the resultant shape can be varied, deformed or corrected. In certain embodiments, the variation can be used to select and/or design an implant component having an ideal or optimized feature or shape, e.g., corresponding to the deformed or corrected joint feature or shape. For example, in one application of this embodiment, the ideal or optimized implant shape reflects the shape of the patient's joint before he or she developed arthritis. For example, if a varus deformity of the knee is observed, virtual realignment can be addressed by including added thickness to the model (or taking away thickness, etc.) to the area or multiple areas (i.e., increase/decrease on a single side, or a combination of increase on a medial/lateral condylar side and decrease on the lateral/medial condylar side of the knee joint) that would produce a leg in neutral alignment. For a grossly mal-aligned contra-lateral leg, correction can be per a surgeon's order.

Variation of the joint or portions of the joint can include, without limitation, variation of one or more external surfaces, internal surfaces, joint-facing surfaces, uncut surfaces, cut surfaces, altered surfaces, and/or partial surfaces as well as osteophytes, subchondral cysts, geodes or areas of eburnation, joint flattening, contour irregularity, and loss of normal shape. The surface or structure can be or reflect any surface or structure in the joint, including, without limitation, bone surfaces, ridges, plateaus, cartilage surfaces, ligament surfaces, or other surfaces or structures. The surface or structure derived can be an approximation of a healthy joint surface or structure or can be another variation. The surface or structure can be made to include pathological alterations of the joint. The surface or structure also can be made whereby the pathological joint changes are virtually removed in whole or in part.

Alternatively or in addition, the variation can be used to select and/or design a patient-adapted surgical procedure to address the deformity or abnormality. For example, the variation can include surgical alterations to the joint, such as virtual resection cuts, virtual drill holes, virtual removal of osteophytes, and/or virtual building of structural support in the joint deemed necessary or beneficial to a desired final outcome for a patient. As part of the design and/or selection process, the various virtual models of the joint can be queried and appropriate surgical tools, including measuring tools as described herein, can be designed and/or selected and/or modified for use in the implantation procedure.

Exemplary Tool Design/Selection Process

Figure 18:
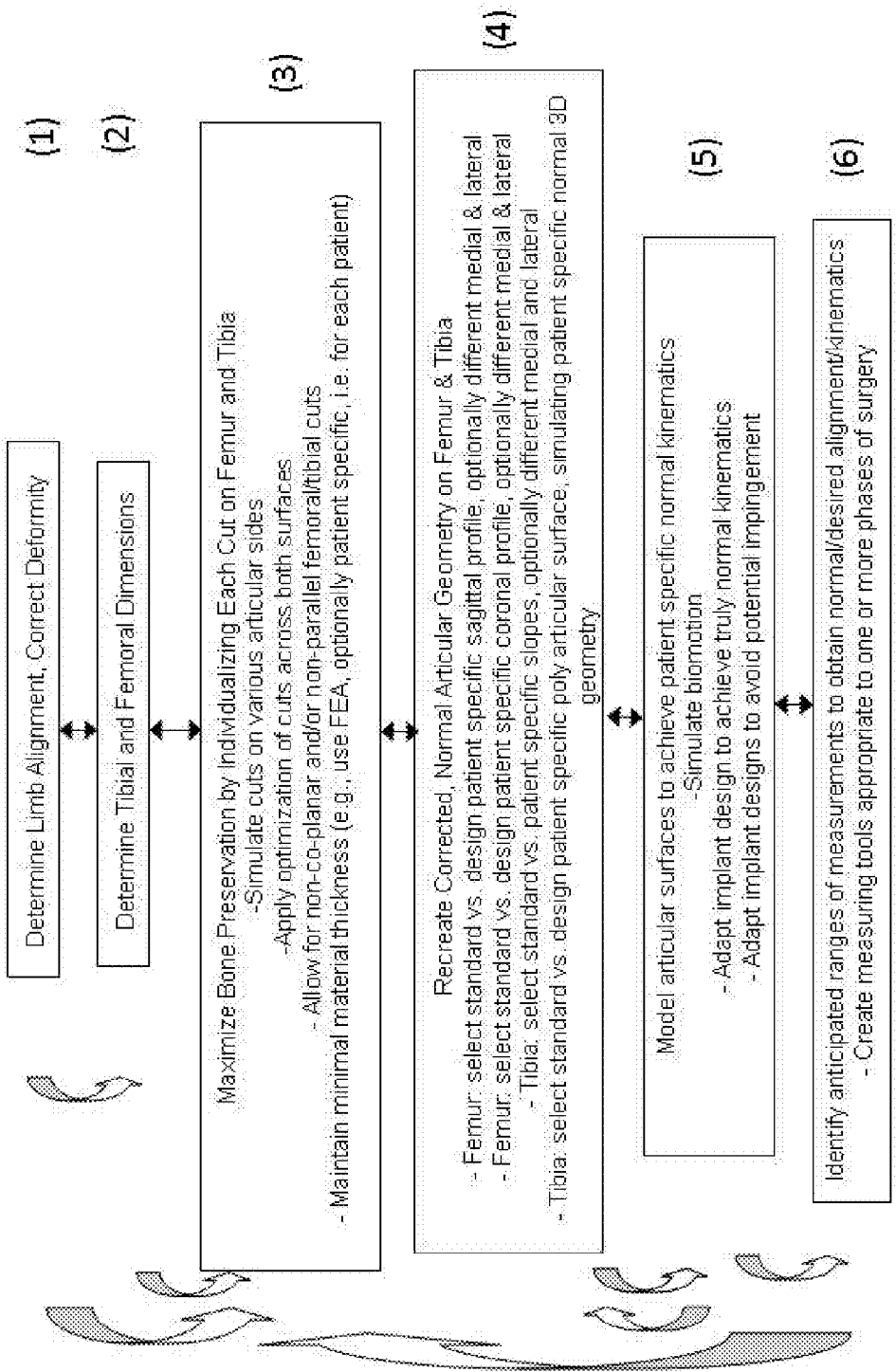
FIG. 18 shows one exemplary flowchart of a process for designing an assessment probe/measuring tool and associated procedures and methods.

FIG. 18 shows one exemplary flowchart of a process for designing a measuring tool and associated procedures and methods, beginning with the collection of patient data in process steps. This data is used by process to convert and display the native anatomy to a user. In various process steps, the image data can be used with implant specific data to design implants, guide tools, measuring tools and/or other instruments. The exemplary process includes various steps, many of which can be optional depending upon surgeon and/or designer preference, as well as the patient's anatomical and/or surgical needs. Many of the steps can be performed virtually, for example, by using one or more computers that have or can receive patient-specific data and specifically configured software or instructions to perform such steps.

In step (1), image data is obtained and limb alignment and deformity corrections are determined, to the extent that either is needed for a specific patient's situation.

In step (2), the requisite femoral and tibial dimensions of the implant components are determined based on patient-specific data obtained, for example, from image data of the patient's shoulder.

In step (3), various boundary conditions or constraints can be defined and utilized in designing appropriate cuts and other preparation of relevant anatomical structures for receiving implant components. One such exemplary constraint may be maximizing bone preservation by virtually determining a resection cut strategy for the patient's femur and tibia that provides minimal bone loss optionally while also meeting other user-defined parameters such as, for example, maintaining a minimum implant thickness, using certain resection cuts to help correct the patient's misalignment, removing diseased or undesired portions of the patient's bone or anatomy, and/or other parameters. This general step can include one or more of the steps of (i) simulating resection cuts on one or both articular sides (e.g., on the femur and/or tibia), (ii) applying optimized cuts across one or both articular sides, (iii) allowing for non-co-planar and/or non-parallel resection cuts and (iv) maintaining and/or determining minimal material thickness. The minimal material thickness for the implant selection and/or design can be an established threshold, for example, as previously determined by a finite element analysis ("FEA") of the implant's standard characteristics and features. Alternatively, the minimal material thickness can be determined for the specific implant, for example, as determined by an FEA of the implant's standard and patient-specific characteristics and features. If desired, FEA and/or other load-bearing/modeling analysis may be used to further optimize or otherwise modify the individual implant design, such as where the implant is under or over-engineered than required to accommodate the patient's biomechanical needs, or is otherwise undesirable in one or more aspects relative to such analysis. In such a case, the implant design may be further modified and/or redesigned to more accurately accommodate the patient's needs, which may have the side effect of increasing/reducing implant characteristics (i.e., size, shape or thickness) or otherwise modifying one or more of the various design "constraints" or limitations currently accommodated by the present design features of the implant. If desired, this step can also assist in identifying for a surgeon the bone resection design to perform in the surgical theater and it also identifies the design of the bone-facing surface(s) of the implant components, which substantially negatively-match the patient's resected bone surfaces, at least in part.

In step (4), a corrected, normal and/or optimized articular geometry on the femur and tibia can be recreated virtually. For the femur, this general step can include, for example, the step of: (i) selecting a standard sagittal profile, or selecting and/or designing a patient-engineered or patient-specific sagittal profile; and (ii) selecting a standard coronal profile, or selecting and/or designing a patient-specific or patient-engineered coronal profile. Optionally, the sagittal and/or coronal profiles of one or more corresponding medial and lateral portions (e.g., medial and lateral condyles) can include different curvatures. For the tibia, this general step includes one or both of the steps of: (iii) selecting a standard anterior-posterior slope, and/or selecting and/or designing a patient-specific or patient-engineered anterior-posterior slope, either of which optionally can vary from medial to lateral sides; and (iv) selecting a standard poly-articular surface or insert, or selecting and/or designing a patient-specific or patient-engineered poly-articular surface or insert. The patient-specific poly-articular surface can be selected and/or designed, for example, to simulate the normal or optimized three-dimensional geometry of the patient's tibial articular surface. The patient-engineered poly-articular surface can be selected and/or designed, for example, to optimize kinematics with the bearing surfaces of the femoral implant component. This step can be used to define the bearing portion of the outer, joint-facing surfaces (i.e., articular surfaces) of the implant components. In various embodiments for a knee joint, the insert(s) can include patient-specific poly-articular surface(s) selected and/or designed, for example, to simulate the normal or optimized three-dimensional geometry of the patient's tibial articular surface and/or surrounding periphery. For a shoulder implant, the patient-engineered poly-articular surface can be selected and/or designed, for example, to optimize kinematics with the bearing surfaces of the humeral implant component. This step can be used to define the bearing portion of the outer, joint-facing surfaces (i.e., articular surfaces) of the implant components.

In step (5), a virtual implant model (for example, generated and displayed using a computer specifically configured with software and/or instructions to assess and display such models) is assessed and can be altered to achieve normal or optimized kinematics for the patient. For example, the outer joint-facing or articular surface(s) of one or more implant components can be assessed and adapted to improve kinematics for the patient. This general step can include one or more of the steps of: (i) virtually simulating biomotion of the model, (ii) adapting the implant design to achieve normal or optimized kinematics for the patient, and (iii) adapting the implant design to avoid potential impingement.

In step (6), the various joint models and proposed modified/repaired models can be queried to determine a required or viable range of measuring tools necessary for proper assessment, evaluation, balancing and optimization of kinematics for the joint replacement procedure. Such queries can reveal a variety of measuring tool shapes, sizes and/or configurations for use in the various stages of the surgical procedure. Tool designs can also be discovered or developed that correspond to various combinations of modular components (i.e., poly insert and tray combinations) identified in previous steps. In various embodiments, one or more measuring tool sets can be created to facilitate the assessment, evaluation, measurement, alignment and kinematic balancing of the joint during the implantation procedure.

The various measuring tools described herein can be selected and/or designed to include one or more features that achieve an anatomic or near anatomic fit with the existing surface or with a resected surface of the joint. Moreover, the measuring tools can be selected and/or designed, for example, to replicate the patient's existing joint anatomy, to replicate the patient's healthy joint anatomy, to enhance the patient's joint anatomy, and/or to optimize fit with an opposing implant component. Accordingly, both the existing surface of the joint and the desired resulting surface of the joint can be assessed. This technique can be applicable both to implants secured to underlying anatomical structures (i.e., anchored to the bone), as well as implants that are not anchored into the bone.

Any of the methods described herein can be performed, at least in part, using a computer-readable medium having instructions stored thereon, which, when executed by one or more processors, causes the one or more processors to perform one or more operations corresponding to one or more steps in the method. Any of the methods can include the steps of receiving input from a device or user and producing an output for a user, for example, a physician, clinician, technician, or other user. Executed instructions on the computer-readable medium (i.e., a software program) can be used, for example, to receive as input patient-specific information (e.g., images of a patient's biological structure) and provide as output a virtual model of the patient's biological structure. Similarly, executed instructions on a computer-readable medium can be used to receive as input patient-specific information and user-selected and/or weighted parameters and then provide as output to a user values or ranges of values for those parameters and/or for resection cut features, guide tool features, and/or implant component features. For example, in certain embodiments, patient-specific information can be input into a computer software program for selecting and/or designing one or more resection cuts, measuring and guide tools, and/or implant components, and one or more of the following parameters can be optimization in the design process: (1) correction of joint deformity; (2) correction of a limb alignment deformity; (3) preservation of bone, cartilage, and/or ligaments at the joint; (4) preservation, restoration, or enhancement of one or more features of the patient's biology, for example, trochlea and trochlear shape; (5) preservation, restoration, or enhancement of joint kinematics, including, for example, ligament function and implant impingement; (6) preservation, restoration, or enhancement of the patient's joint-line location and/or joint gap width; and (7) preservation, restoration, or enhancement of other target features.

Optimization of multiple parameters may result in conflicting constraints; for example, optimizing one parameter may cause an undesired deviation to one or more other parameters. In cases where not all constraints can be achieved at the same time, parameters can be assigned a priority or weight in the software program. The priority or weighting can be automated (e.g., part of the computer program) and/or it can be selected by a user depending on the user's desired design goals, for example, minimization of number or type of measuring tools, minimization of bone loss, or retention of existing joint-line to preserve kinematics, or combination to accommodate both parameters in overall design. As an illustrative example, in certain embodiments, selection and/or design of a measuring tool for a knee implantation procedure can include obtaining patient-specific information (e.g., from radiographic images or CT images) of a patient's knee and inputting that information into the computer program to model features such as minimum thickness of femoral component (to minimize resected bone on femur), tibial resection cut height (to minimize resected bone on tibia), and joint-line position (preferably to preserve for natural kinematics). These features can be modeled and analyzed relative to a weighting of parameters such as preserving bone and preserving joint kinematics. As output, one or more resection cut features, measuring tool features, and/or implant component features that optimize the identified parameters relative to the selective weightings can be provided.

In any automated process or process step performed by the computer system, constraints pertaining to a specific implant model, to a group of patients or to the individual patient may be taken into account. For example, the maximum implant thickness or allowable positions of implant anchors can depend on the type of implant. The minimum allowable implant thickness can depend on the patient's bone quality.

Any one or more steps of the assessment, selection, and/or design may be partially or fully automated, for example, using a computer-run software program and/or one or more robotic procedures known in the art. For example, processing of the patient data, the assessment of biological features and/or feature measurements, the assessment of implant component features and/or feature measurements, the optional assessment of resection cut and/or measuring or guide tool features and/or feature measurements, the selection and/or design of one or more features of a patient-adapted implant component, and/or the implantation procedure(s) may be partially or wholly automated. For example, patient data, with optional user-defined parameters, may be inputted or transferred by a user and/or by electronic transfer into a software-directed computer system that can identify variable implant component features and/or feature measurements and perform operations to generate one or more virtual models and/or implant design specifications, for example, in accordance with one or more target or threshold parameters.

Biomotion Modeling

As part of the design and/or selection process, biomotion models for a particular patient can be supplemented with patient-specific finite element modeling or other biomechanical models known in the art. Resultant forces in the knee or shoulder joint can be calculated for each component for each specific patient. The implant can be engineered to the patient's load and force demands. For instance, a 125 lb. patient may not need a tibial insert as thick as a patient with 280 lbs. Alternatively, the articular tissues in the knee of a 250 lb. patient may appear quite thick on an x-ray image, but the actual tissue condition may actually be much more "compressed" or thinned, due to the patient's larger mass, than may be apparent from the images if they were taken of the patient in a sitting or supine position. In many cases, the polyethylene can be adjusted in shape, thickness and material properties for each patient. For example, a 3 mm polyethylene insert can be used in a light patient with low force and a heavier, stronger or more active patient may require a different implant size and/or design, such as an 8 mm thick polymer insert or similar device. In order to accommodate such changes, and estimate the various ranges of thickness tools as described herein, such modeling may be advantageous.

In various embodiments, the thickness of one or more implant components or portions of one or more implant components can be selected or adapted or designed based on one or more geometric features of a patient or patient weight or height or BMI or other patient specific characteristics, e.g. gender, lifestyle, activity level etc. This selection or adaptation or design can be performed for any implant component and/or surgical tool, including measurement tools. The metal, ceramic or plastic thickness, as well as the thickness of one or more optional portions thereof, can be selected, adapted or designed using this or similar information.

The biomotion model can then be individualized with use of patient-specific information including at least one of, but not limited to the patient's age, gender, weight, height, body mass index, and race, the desired limb alignment or deformity correction, and the patient's imaging data, for example, a series of two-dimensional images or a three-dimensional representation of the joint for which surgery is contemplated.

By optimizing implant shape and associated procedures and surgical tools, including measuring tools, in this manner, it is possible to establish normal or near normal kinematics. Moreover, it is possible to avoid implant related complications, including, but not limited to tissue or component impingement in high flexion or rotation, and other complications associated with existing implant designs. Since traditional implants follow a one-size-fits-all approach, they are generally limited to altering only one or two aspects of an implant design. However, with the design approaches described herein, various features of an implant component and measuring tools can be designed for an individual to address multiple issues, including issues associated with various particularized motion. For example, designs as described herein can alter an implant component's bone-facing surface (for example, number, angle, and orientation of bone cuts), joint-facing surface (for example, surface contour and curvatures) and other features (for example, implant height, width, and other features) to address patient-specific issues.

Cartilage Coring Models

While non-invasive imaging techniques such as CT-scans and x-rays (and other non-invasive imaging modalities described herein, to varying extent) are quite useful in differentiating denser or harder structures such as bones, it is often difficult to differentiate the margins of softer tissues such as articular cartilage, especially where opposing articulating cartilage surfaces interact. For example, where an image has been taken of a patient's knee, it may be relatively easy to identify the outer cortical bone margins of the femur (femoral condyles) and the tibia (tibial plateau structures), but the margins of the articular cartilage surrounding such structures will generally be unclear or indistinct. Thus, while a bone's subchondral bone surface may be readily apparent (and derivable) from such an image, in many cases the shape of the subchondral bone and surrounding articular cartilage may not be readily ascertained until it is directly visualized by the surgeon during the surgical procedure.

In one exemplary embodiment, a measuring tool can include one or more features to accommodate or facilitate the assessment and balancing of a joint using subchondral bone data. The measuring tool will desirably engage with subchondral bone of a joint structure, using MRI or CT data and a model of the anatomical image data which could be created using a Boolean subtraction operation or other techniques known in the art. If desired, the model can include a desired gap to simulate the existing articulating cartilage tissues on one or both adjacent structures, or can use an estimated gap derived from a database of anatomical data of healthy individuals of a given population. In various embodiments, this gap may be as little as approximately 1 mm, approximately 3 mm or 5 mm or larger, to accommodate cartilage and/or slight errors in the reconstruction, which can then be included in the estimated range to be accommodated by the measuring tool or tools.

During the surgical operation, a cartilage "coring" or removal operation can be accomplished on the relevant anatomical surface (i.e., removal of a strip of cartilage on a femoral condyle, such as shown in FIG. 13), and the measuring tool can desirably engage with the subchondral bone revealed therein, facilitating a highly accurate assessment and measurement of the associated joint structures using various techniques described herein.

If desired, a measuring tool could include one or more holes or slots, passing through the instrument body, which desirably extend from a lower surface to an upper surface. Such holes or slots or other features could be useful for a variety of reasons, including to direct and/or align cutting instruments, drilling instrument, reaming instruments, to visualize native surfaces through the holes and/or to be used for the placement of alignment and/or securement pins. Holes can also be useful for aligning of coring or debriding instruments for removal of specific locations of articular cartilage on the relevant anatomical structures, exposing one or more subchondral bone surfaces that can subsequently be used to align further guide tool instruments. As previously noted, the use of subchondral bone alignment in this manner facilitates the alignment of subsequent tools, as subchondral bone is generally easier to visualize than articular cartilage and/or other soft tissues, thus providing a more reliable reference surface for the surgical procedure.

Avoiding Anatomy/Ligaments

The various techniques described herein can include evaluation of the "fit" of various surgical tools, including measuring instruments, within a given anatomical space, including within an articulating space between adjacent bony structures. In many cases, various models and anatomical image information of a patient may be useful during the design/selection of the implant, measuring and surgical tools, cut guides and surgical procedures, as well as before during or after bone preparation is performed, to insure that "breakthrough" or other unintended damage to adjacent anatomical structures does not occur.

Moreover, surgical tools that exit bones or other areas of a joint in an unintended manner during surgery (such as through a fracture) can cause significant damage to many important anatomical structures adjacent the joint, including major blood vessels and/or nerve complexes. By utilizing patient-specific image data (and modeling thereof), and creating implants, tools and surgical techniques appropriate to the imaged/modeled anatomy, the surgical procedure, and the ultimate fixation of the implant components, can be significantly improved.

Various features described herein can also include the use of patient-specific and/or patient-adapted image data and models to determine the opportunity, incidence, likelihood and/or danger of unintended and/or accidental damage to adjacent anatomical structures. Depending upon the surgical repair and the physician's preference, various anatomical structures such as tendons, ligaments, nerves and/or major blood vessels may be preferably avoided, which may alter the ultimate surgical procedure and/or guide tools, instruments and/or implant components designed, selected and used to accomplish a desired surgical correction. The use of such data to ensure clearance spaces, accommodate blocking structures (i.e., reamers or shields to protect various areas from cutting instruments) and/or to modify measuring tool alignment and/or structure is contemplated herein. For example, a measuring tool could include a clearance space or blunt surface that avoids or shields an ACL or PCL of a knee joint, muscle and other tissue, thereby minimizing opportunity for inadvertent injury.

Measuring tool design and modeling also can be used to achieve ligament sparing in a shoulder joint, for example, with regard to the subscapularis tendon or a biceps tendon. An imaging test can be utilized to identify, for example, the origin and/or the insertion of the subscapularis tendon or a biceps tendon on the glenoid/scapula. The origin and the insertion can be identified by visualizing, for example, the ligaments directly, as is possible with MRI or spiral CT arthrography, or by visualizing bony landmarks known to be the origin or insertion of the ligament such as the medial and lateral tibial spines and inferring the soft tissue location(s). An implant system and associated measuring tools (and other surgical tools) can then be selected or designed based on the direct or inferred image and location data so that, for example, the glenoid component preserves the subscapularis tendon or a biceps tendon origin. The implant can be selected or designed so that bone cuts adjacent to the subscapularis tendon or a biceps tendon attachment or origin do not weaken the bone to induce a potential fracture.

Any implant component can be selected and/or adapted in shape so that it stays clear of important ligament structures, but such modification to the implant may affect the surgical procedure and surgical tools (including the size and/or shape of measuring tools) utilized therewith. Imaging data can help identify or derive shape or location information on such ligamentous structures. For example, an implant system can include a concavity or divot to avoid the tendon or other soft tissue structure. Imaging data can be used to design a component or tool (all polyethylene or other plastic material or metal backed) that avoids the attachment of the various tendons/ligaments; specifically, the contour of the implant can be shaped so that it will stay clear of such structures. A safety margin, e.g. 2 mm or 3 mm or 5 mm or 7 mm or 10 mm can be applied to the design of the edge of the component or tool to allow the surgeon more intraoperative flexibility.

Where a multi-part implant component includes one or more insert components, such as a tibial tray, the margin of the implant component, e.g. a polyethylene- or metal-backed tray with polyethylene inserts, can be selected and/or designed using the imaging data or shapes derived from the imaging data so that the implant component will not interfere with and stay clear of tendons, ligaments or other important structures. In a similar manner, measuring tools can be designed and/or selected to desirably avoid such structures.

Manufacturing

The various steps of designing a measuring tool as described herein can include both configuring one or more features, measurements, and/or dimensions of the tool (e.g., derived from patient-specific data from a particular patient and adapted for the particular patient) and manufacturing the tool. In certain embodiments, manufacturing can include making the measuring tool from starting materials, for example, metals and/or polymers or other materials in solid (e.g., powders or blocks) or liquid form. In addition or alternatively, in certain embodiments, manufacturing can include altering (e.g., machining) an existing tool, for example, a standard tool blank component and/or an existing tool (e.g., selected from a library). The manufacturing techniques to making or altering a tool can include any techniques known in the art today and in the future. Such techniques include, but are not limited to additive as well as subtractive methods, i.e., methods that add material, for example to a standard blank, and methods that remove material, for example from a standard blank.

Various technologies appropriate for this purpose are known in the art, for example, as described in Wohlers Report 2009, State of the Industry Annual Worldwide Progress Report on Additive Manufacturing, Wohlers Associates, 2009 (ISBN 0-9754429-5-3), available from the web www.wohlersassociates.com; Pham and Dimov, *Rapid manufacturing*, Springer-Verlag, 2001 (ISBN 1-85233-360-X); Grenda, *Printing the Future, The 3D Printing and Rapid Prototyping Source Book*, Castle Island Co., 2009; *Virtual Prototyping & Bio Manufacturing in Medical Applications*, Bidanda and Bartolo (Eds.), Springer, Dec. 17, 2007 (ISBN: 10: 0387334297; 13: 978-0387334295); *Bio-Materials and Prototyping Applications in Medicine*, Bártolo and Bidanda (Eds.), Springer, Dec. 10, 2007 (ISBN: 10: 0387476822; 13: 978-0387476827); Liou, *Rapid Prototyping and Engineering Applications: A Toolbox for Prototype Development*, CRC, Sep. 26, 2007 (ISBN: 10: 0849334098; 13: 978-0849334092); *Advanced Manufacturing Technology for Medical Applications: Reverse Engineering, Software Conversion and Rapid Prototyping*, Gibson (Ed.), Wiley, January 2006 (ISBN: 10: 0470016884; 13: 978-0470016886); and Branner et al., "Coupled Field Simulation in Additive Layer Manufacturing," 3rd International Conference PMI, 2008 (10 pages).

Exemplary techniques for adapting a measuring tool to a patient's anatomy include, but are not limited to those shown in Table 4.

TABLE 4

Exemplary techniques for forming or altering a surgical tool, including a patient-specific and/or patient-engineered component for use with a patient's anatomy

| Technique | Brief description of technique and related notes |
| --- | --- |
| CNC | CNC refers to computer numerically controlled (CNC) machine tools, a computer-driven technique, e.g., computer-code instructions, in which machine tools are driven by one or more computers. Embodiments of this method can interface with CAD software to streamline the automated design and manufacturing process. |
| CAM | CAM refers to computer-aided manufacturing (CAM) and can be used to describe the use of software programming tools to efficiently manage manufacturing and production of products and prototypes. CAM can be used with CAD to generate CNC code for manufacturing three-dimensional objects. |
| Casting, including casting using rapid prototyped casting patterns | Casting is a manufacturing technique that employs a mold. Typically, a mold includes the negative of the desired shape of a product. A liquid material is poured into the mold and allowed to cure, for example, with time, cooling, and/or with the addition of a solidifying agent. The resulting solid material or casting can be worked subsequently, for example, by sanding or bonding to another casting to generate a final product. |
| Welding | Welding is a manufacturing technique in which two components are fused together at one or more locations. In certain embodiments, the component joining surfaces include metal or thermoplastic and heat is administered as part of the fusion technique. |
| Forging | Forging is a manufacturing technique in which a product or component, typically a metal, is shaped, typically by heating and applying force. |
| Rapid prototyping | Rapid prototyping refers generally to automated construction of a prototype or product, typically using an additive manufacturing technology, such as EBM, SLS, SLM, SLA, DMLS, 3DP, FDM and other technologies |
| EBM ® | EBM ® refers to electron beam melting (EBM ®), which is a powder-based additive manufacturing technology. Typically, successive layers of metal powder are deposited and melted with an electron beam in a vacuum. |
| SLS | SLS refers to selective laser sintering (SLS), which is a powder-based additive manufacturing technology. Typically, successive layers of a powder (e.g., polymer, metal, sand, or other material) are deposited and melted with a scanning laser, for example, a carbon dioxide laser. |
| SLM | SLM refers to selective laser melting ™ (SLM), which is a technology similar to SLS; however, with SLM the powder material is fully melted to form a fully-dense product. |
| SLA or SL | SLA or SL refers to stereolithography (SLA or SL), which is a liquid-based additive manufacturing technology. Typically, successive layers of a liquid resin are exposed to a curing, for example, with UV laser light, to solidify each layer and bond it to the layer below. This technology typically requires the additional and removal of support structures when creating particular geometries. |
| DMLS | DMLS refers to direct metal laser sintering (DMLS), which is a powder-based additive manufacturing technology. Typically, metal powder is deposited and melted locally using a fiber optic laser. |

TABLE 4-continued

Exemplary techniques for forming or altering a surgical tool, including a patient-specific and/or patient-engineered component for use with a patient's anatomy

| Technique | Brief description of technique and related notes |
| --- | --- |
|  | Complex and highly accurate geometries can be produced with this technology. This technology supports net-shaping, which means that the product generated from the technology requires little or no subsequent surface finishing. |
| LC | LC refers to LaserCusing ®(LC), which is a powder-based additive manufacturing technology. LC is similar to DMLS; however, with LC a high-energy laser is used to completely melt the powder, thereby creating a fully-dense product. |
| 3DP | 3DP refers to three-dimensional printing (3DP), which is a high-speed additive manufacturing technology that can deposit various types of materials in powder, liquid, or granular form in a printer-like fashion. Deposited layers can be cured layer by layer or, alternatively, for granular deposition, an intervening adhesive step can be used to secure layered granules together in bed of granules and the multiple layers subsequently can be cured together, for example, with laser or light curing. |
| LENS | LENS ® refers to Laser Engineered Net Shaping ™ (LENS ®), which is a powder-based additive manufacturing technology. Typically, a metal powder is supplied to the focus of the laser beam at a deposition head. The laser beam melts the powder as it is applied, in raster fashion. The process continues layer by and layer and requires no subsequent curing. This technology supports net-shaping, which means that the product generated from the technology requires little or no subsequent surface finishing. |
| FDM | FDM refers to fused deposition modeling ™ (FDM) is an extrusion-based additive manufacturing technology. Typically, beads of heated extruded polymers are deposited row by row and layer by layer. The beads harden as the extruded polymer cools. |

Any assessment probe or measuring tool components, or portions thereof, can be formed or adapted based on a pre-existing blank. For example, in a joint or a spine, an imaging test, e.g., a CT or MRI, can be obtained to generate information, for example, about the shape or dimensions of the relevant anatomical features, i.e., bones, cartilage and/or connective or soft tissues, as well as any other portions of the joint. Various dimensions or shapes of the joint can be determined and a pre-existing blank can then be selected. The shape of the pre-existing blank component can then be adapted to the patient's shape, for example, by selectively removing material, e.g. with a machining or cutting or abrasion or other process, or by adding material. The shape of the blank will generally be selected to be smaller than that required for the target anatomy when material is added to achieve the patient adapted or patient specific implant features or surfaces. The shape of the blank will generally be selected to be larger than that required for the target anatomy when material is removed to achieve the patient adapted or patient specific implant features or surfaces. Any manufacturing process known in the art or developed in the future can be used to add or remove material, including for metals, ceramics, plastics and other materials.

The various measuring instruments described herein can be defined and manufactured from any biocompatible material, including, sterilizable plastic, polymers, ceramics, metals or combinations thereof, using various manufacturing processes. The tools can be disposable and can be combined or used with reusable and non patient-specific cutting and guiding components. The instruments will desirably be steam sterilizable and biocompatible. In various embodiments, the tools will desirably include a minimal profile and/or volume, and simulation of passage of these instruments through the chosen incision should be performed prior to manufacture, as the surgical exposure for these types of procedures can be quite small. In various embodiments, the design and/or selection of the various instruments and/or implants may be particularized for an intended resection type and/or direction, such as particularized to allow handle extension through and/or out of a less-invasive incision of a knee joint and/or designing a measuring tool to conform to surfaces directly accessible through an anterior and/or superior incision in the shoulder.

In various embodiments, the assessment probes and/or measurement tools described herein may include various indicia that identifies a corresponding individual patient or group of patients, procedures and/or corresponding implant components for use with the tool, as well as uses for which the tool was designed or intended (i.e., for use in assessing natural surfaces, modified surfaces and/or surfaces having implants, etc).

FEA and Optimization of Designs/Selections

In various embodiments, the design, selection and/or optimization of surgical measuring tools can include an automated analysis of the strength, durability and fatigue resistance of the tool and/or portions thereof as well as of the bones or other structures against which they are to be used. The thickness and/or other design features of a measuring tool can be included as part of the surgical procedure design to ensure a threshold strength for the tool in the face of the stresses and forces associated with insertion/removal of the tool as well possible joint motion, such as lifting, hanging and pushing/pulling, during the measuring/assessment process. In various embodiments, a Finite Element Analysis (FEA) assessment may be conducted for tool components of various sizes and with various surgical procedural steps, including bone cut numbers and orientations. Such analyses may indicate maximum principal stresses observed in FEA analysis that can be used to establish an acceptable minimum tool or component thickness for an implant component having a particular size and, optionally, for a particular patient (e.g., having a particular weight, age, activity level, etc). These results may indicate suboptimal designs for surgical tools, which may necessitate alterations to the intended tool design as well as potentially impact the intended procedure and/or implant component design in various manners. In this way, the threshold thickness, surface features design and/or any tool component feature can be adapted to a particular patient based on a combination of patient-specific geometric data and on patient-specific anthropometric data.

In various alternative embodiments, the design, selection and/or optimization of surgical measuring tools can include an assessment of the various measuring tools and tool sizes/shapes required during the surgical procedure for differing types of assessments, including assessments of (1) native anatomical structures, (2) resected or prepared anatomical structures, and/or (3) implanted components or trials and associated inserts. If desired, a multiplicity of surgical procedures and implant/tool designs can be assessed and compared, and similar measuring tool features can be identified for differing measurements. Desirably, a single tool or reduced number of tools can be identified that is suitable for multiple measurements during a given surgical procedure, such as a tool that is suitable for assessing both the natural anatomical condition (prior to bone modification) as well as balancing and optimizing kinematics for selection if an appropriate insert after implantation of implant components. Such selection and optimization may indicate suboptimal designs for measuring tools, which may necessitate design or selection of other measuring tools, as well as potentially impact the intended procedure and/or implant component designs in various manners (i.e., the procedure or implant components may be modified to accommodate a reduced number of measuring tools).

Kitting

Various portions and embodiments described herein can be provided in a kit, which can include various combinations of patient-specific and/or patient-adapted implant and/or tools, including implant components, guide tools, jigs, and surgical instruments such as saws, drills and broaches. Various components, tools and/or procedural steps can include standard features alone and/or in combination with patient-specific and/or patient-adapted features. If desired, various portions of the kit can be used for a plurality of procedures and need not be customized for a particular procedure or patient. Further, the kit can include a plurality of portions that allow it to be used in several procedures for many differing anatomies, sizes, and the like. Further, various other portions, such as the reamers and/or other tools can be appropriate for a plurality of different patients.

Remote Transmission and Processing of Image Data

The various techniques and devices described herein, as well as the image and modeling information provided by systems and processes of the present disclosure, facilitate telemedical techniques, because they provide useful images for distribution to distant geographic locations where expert surgical or medical specialists may collaborate during surgery. Thus, systems and processes according to various embodiments of the present disclosure can be used in connection with computing functionality which is networked or otherwise in communication with computing functionality in other locations, whether by PSTN, information exchange infrastructures such as packet switched networks including the Internet, or as otherwise desire. Such remote imaging may occur on computers, wireless devices, videoconferencing devices or in any other mode or on any other platform which is now or may in the future be capable of rending images or parts of them produced in accordance with various embodiments of the present disclosure. Parallel communication links such as switched or unswitched telephone call connections may also accompany or form part of such telemedical techniques. Distant databases such as online catalogs of implant suppliers or prosthetics buyers or distributors may form part of or be networked with computing functionality to give the surgeon in real time access to additional options for implants which could be procured and used during the surgical operation.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

The various descriptions contained herein are merely exemplary in nature and, thus, variations that do not depart from the gist of the teachings are intended to be within the scope of the teachings. Such variations are not to be regarded as a departure from the spirit and scope of the teachings, and the mixing and matching of various features, elements and/or functions between various embodiments is expressly contemplated herein. One of ordinary skill in the art would appreciate from this disclosure that features, elements and/or functions of one embodiment may be incorporated into another embodiment as appropriate, unless described otherwise above. Many additional changes in the details, materials, and arrangement of parts, herein described and illustrated, can be made by those skilled in the art. Accordingly, it will be understood that the following claims are not to be limited to the embodiments disclosed herein, can include practices otherwise than specifically described, and are to be interpreted as broadly as allowed under the law.

What is claimed is:

1. A system for treating a joint of a patient, the system comprising:
    an assessment probe, the assessment probe including first and second prongs connected at a common hub,
    the first prong extending from the common hub in a first direction and
    the second prong extending from the common hub in a direction substantially the same as the first direction,
    the first prong having a first predetermined thickness and the second prong having a second predetermined thickness, the first thickness being different from the second thickness; and
    a patient-specific mold, the patient-specific mold including at least one patient-specific surface having a shape based, at least in part, on a shape of a corresponding surface of the joint of the patient, wherein the at least one patient-specific surface is configured to mate with the corresponding surface of the joint of the patient, wherein the joint of the patient is a hip or shoulder joint of the patient.

2. The system of claim 1, wherein the joint of the patient is a hip joint of the patient.

3. The system of claim 2, wherein the assessment probe is configured to measure distraction of two portions of a femoral head of the hip joint of the patient simultaneously.

4. The system of claim 1, wherein the joint of the patient is a shoulder joint of the patient.

5. The system of claim 4, wherein the assessment probe is configured to measure distraction of two portions of a humeral head of the shoulder joint of the patient simultaneously.

\* \* \* \* \*